United States Patent
Silver et al.

(10) Patent No.: US 7,181,261 B2
(45) Date of Patent: Feb. 20, 2007

(54) IMPLANTABLE, RETRIEVABLE, THROMBUS MINIMIZING SENSORS

(76) Inventors: James H. Silver, 45 Roosevelt Cir., Palo Alto, CA (US) 94306; Darius Fredrick Mostowfi, 248 Beverly Dr., San Carlos, CA (US) 94070

( * ) Notice: Subject to any disclaimer, the term of this patent is extended or adjusted under 35 U.S.C. 154(b) by 5 days.

(21) Appl. No.: 10/758,495

(22) Filed: Jan. 15, 2004

(65) Prior Publication Data

US 2004/0176672 A1    Sep. 9, 2004

Related U.S. Application Data

(63) Continuation-in-part of application No. 10/217,202, filed on Aug. 9, 2002, now Pat. No. 7,006,858, which is a continuation-in-part of application No. 10/041,036, filed on Nov. 8, 2001, now Pat. No. 7,033,322, which is a continuation-in-part of application No. 09/571,702, filed on May 15, 2000, now Pat. No. 6,442,413.

(51) Int. Cl.
*A61B 5/05* (2006.01)
*C12N 9/00* (2006.01)
*C12N 11/00* (2006.01)
*C12M 1/00* (2006.01)
*C25B 9/00* (2006.01)
*G01N 1/00* (2006.01)

(52) U.S. Cl. ................... 600/345; 204/403.01

(58) Field of Classification Search ............... None
See application file for complete search history.

(56) References Cited

U.S. PATENT DOCUMENTS

| | | | |
|---|---|---|---|
| 4,580,568 | A | 4/1986 | Gianturco |
| 4,655,771 | A | 4/1987 | Wallsten |
| 4,739,762 | A | 4/1988 | Palmaz |
| 4,886,062 | A | 12/1989 | Wiktor |
| 4,890,620 | A | 1/1990 | Gough |

(Continued)

FOREIGN PATENT DOCUMENTS

WO    WO 99/26530    6/1999

(Continued)

OTHER PUBLICATIONS

Measurement of Acetylcholine-induced Endothelium-derived Nitric Oxide in Aorta Using a Newly Developed Catheter-type Nitric Oxide Sensor, Science Direct (www.sciencedirect.com), May 14, 2003.

(Continued)

*Primary Examiner*—Robert L. Nasser
(74) *Attorney, Agent, or Firm*—Knobbe Martens Olson & Bear LLP

(57) ABSTRACT

A sensor is disclosed, for implantation within a blood vessel to monitor a substance in or property of blood. In one embodiment, the sensor is retrievable. In another embodiment, the sensor has a layer that minimizes the formation of thrombus. A signal representative of the substance in or property of blood is transmitted to an external receiver. In another embodiment, the sensor detects nitric oxide or a nitric oxide metabolite and can be implanted for a period of hours, days, weeks or years. Methods are also disclosed.

26 Claims, 22 Drawing Sheets

U.S. PATENT DOCUMENTS

| | | | |
|---|---|---|---|
| 5,102,417 | A | 4/1992 | Palmaz |
| 5,183,740 | A | 2/1993 | Ligler et al. |
| 5,195,984 | A | 3/1993 | Schatz |
| 5,284,138 | A | 2/1994 | Kujawski |
| 5,411,551 | A | 5/1995 | Winston et al. |
| 5,421,955 | A | 6/1995 | Lau et al. |
| 5,431,160 | A | 7/1995 | Wilkins |
| 5,433,197 | A | 7/1995 | Stark |
| 5,433,500 | A | 7/1995 | Brorson et al. |
| 5,443,500 | A | 8/1995 | Sigwart |
| 5,873,906 | A | 2/1999 | Lau et al. |
| 5,876,432 | A | 3/1999 | Lau et al. |
| 5,945,676 | A | 8/1999 | Khalil et al. |
| 6,015,387 | A * | 1/2000 | Schwartz et al. ............ 600/504 |
| 6,024,763 | A | 2/2000 | Lenker et al. |
| 6,053,873 | A | 4/2000 | Govari et al. |
| 6,119,028 | A * | 9/2000 | Schulman et al. ........... 600/345 |
| 6,206,835 | B1 * | 3/2001 | Spillman, Jr. et al. ....... 600/485 |
| 6,212,416 | B1 | 4/2001 | Ward et al. |
| 6,231,516 | B1 * | 5/2001 | Keilman et al. ............. 600/485 |
| 6,245,296 | B1 | 6/2001 | Ligler et al. |
| 6,258,026 | B1 | 7/2001 | Ravenscroft et al. |
| 6,280,604 | B1 * | 8/2001 | Allen et al. ............... 205/777.5 |
| 6,285,897 | B1 | 9/2001 | Kilcoyne et al. |
| 6,331,163 | B1 | 12/2001 | Kaplan |
| 6,442,413 | B1 * | 8/2002 | Silver ......................... 600/345 |
| 6,475,235 | B1 | 11/2002 | Jayaraman |
| 6,477,395 | B2 | 11/2002 | Schulman et al. |
| 6,516,808 | B2 | 2/2003 | Schulman |
| 6,638,231 | B2 | 10/2003 | Govari et al. |
| 6,741,877 | B1 | 5/2004 | Shults et al. |
| 6,915,147 | B2 * | 7/2005 | Lebel et al. ................. 600/322 |
| 2002/0042562 | A1 | 4/2002 | Meron et al. |
| 2002/0103424 | A1 | 8/2002 | Swoyer et al. |
| 2004/0210298 | A1 | 10/2004 | Rabkin et al. |
| 2005/0101841 | A9 * | 5/2005 | Kaylor et al. ............... 600/300 |

FOREIGN PATENT DOCUMENTS

| | | |
|---|---|---|
| WO | WO 99/34731 | 7/1999 |
| WO | WO 00/74557 A1 | 12/2000 |

OTHER PUBLICATIONS

Rabbany, S.Y. et al., "*Optical Immunosensors,*" Critical Reviews in Biomedical Engineering, 22(5/6): 307-346 (1994).

Stefan, R.I. et al., "*Immunosensors in Clinical Analysis,*" Fresenius J Anal Chem 366: 659-668 (2000).

Hanbury, C.M. et al., "*Antibody Characteristics for a Continuous Response Fiber Optic Immunosensor for Theophylline,*" Biosensors & Nioelectronics, vol. II (Issue 11): 1129-1138 (1996).

Olukoga, A. et al., "*An Overview of Biochemical Markers In Acute Coronary Syndromes,*" The Journal of The Royal Society for the Promotion of Health, vol. 121 (2): 102-106 (2001).

Gauger, P. et al., "*Explosives Detection In Soil Using a Field-Portable Continuous Flow Immunosensor,*" Journal of Hazardous Materials, 83: 51-63 (2001).

Vianello, F. et al., "*Continuous Flow Immunosensor For Atrazine Detection,*"Biosensors & Bioelectronics, vol. 13 (Issue 1): 45-53 (1998).

Narang, U. et al., "*Multianalyte Detection Using a Capillary-Based Flow Immunosensor,*" Analytical Biochemistry, 255: 13-19 (1998).

Kusterbeck, A.W. et al., "*A Continuous Flow Immunoassay for Rapid and Sensitive Detection of Small Molecules,*" Journal of Immunological Methods, 135: 191-197 (1990).

Charles, P., et al., "*Synthesis of a Fluorescent Analog of Polychlorinated Biphenyls for Use in a Continuous Flow Immunosensor Assay,*" Bioconjugate Chem., vol. 6 (No. 6): 691-694 (1995).

Ma, J. et al., "*Antitumor Effect of the Idiotypic Cascade Induced by an Antibody Encapsulated in Poly(d,l-lactide-co-glycolide) Microspheres,*" Jpn. J. Cancer Res., 92: 1110-1115 (2001).

Torche, A. et al., "*PLGA Microspheres Phagocytosis by Pig Alveolar Macrophages: Influences of poly (vinyl alcohol) Concentration, Nature of Loaded-Protein and Copolymer Nature,*" Journal of Drug Targeting, vol. 7 (No. %): 343-354 (2000).

Mordenti, J. et al., "*Intraocular Pharmacokinetics and Safety of a Humanized Monoclonal Antibody in Rabbits after Intravitreal Administration of a Solution or a PLGA Microsphere Formulation,*"Toxicological Sciences, 52: 101-106 (1999).

Zhu, G. et al., "*Stabilization of Proteins Encapsulated in Sylindrical Poly(lactide-co-glycolide) Implants: Mechanism of Stabilization in Basic Additives,*" Pharmaceutical Research, vol. 17 (No. 3): 351-357 (2000).

Jiang, W. et al., "*Stabilization and Controlled Release of Bovine Serum Albumin Encapsulated in Poly (D, L-lactide) and Poly(ethylene glycol) Microsphere Blends,*" Pharmaceutical Research, vol. 18 (No. 6): 878-885 (2001).

Neuerburg, J. et al., "*New Retrievable Percutaneous Vena Cava Filter: Experimental In Vitro and In Vivo Evaluation,*" Cardiovasc Intervent Radiol, 16:224-229 (1993).

Neuerburg, J. et al., "*Results of a Multicenter Study of the Retrievable Tulip Vena Cava Filter: Early Clinical Experience,*" Cardiovasc Intervent Radiol, 20:10-16 (1997).

Millward, S. et al., "*Gunther Tulip Retrievable Vena Cava Filter: Results from the Registry of the Canadian Interventional Radiology Association,*" J Vasc Interv Radiol, 12:1053-1058 (2001).

Jonsson, B., "The Economic Impact of Diabetes," *Diabetes Care 21* (Suppl. 3): C7-C10 (1998).

"*The Effect of Intensive Treatment of Diabetes on the Development and Progression of Long-Germ Complications in Insulin-Dependent Diabetes Mellitus,*" The Diabetes Control and Complications Trial Research Group, New Eng. J. Med. 329: 977-86 (1993).

Wilkins, E., et al. "*Glucose Monitoring: State of the Art and Future Possibilities,*" Med. Engl.Phys. , 18(4):273-88 (1996).

Jaffari, S.A et al., "*Recent Advances in Amperometric Glucose Biosensors for in vivo Monitoring,*"Physiol. Meas. 16; 1-15 (1995).

Hall, E., "*Biosensors,*" Prentice-Hall, Englewood, NJ ((1991).

Armour, J. et al., "*Application of Chronic Intravascular Blood Glucose Sensor in Dogs,*" Diabetes 39: 1519-26 (1990).

Wilson, G.S. et al., "*Progress Towards the Developments of an Implantable Sensor for Glucose,*" Clin. Chem. 1992 38:1613-7.

Kerner, W. et al., "*A Potentially Implantable Enzyme Electrode for Amperometric Measurement of Glucose,*" Horm. Metab. Res. Suppl. Ther. 20: 8-13 (1988).

Updike, S.J. et al., "*Enzymatic Glucose Sensors: Improved Long-Term Performance in Vitro and In Vivo,*" ASAIO j., 40:157-163 (1994).

Jaremko, J. et al., "*Advances Towards the Implantable Artificial Pancreas for Treatment of Diabetes,*" Diabetes Care, 21(3):444-450 (1998).

Scavani, M. et al., "*Long-Term Implantation of a New Programmable Implantable Insulin Pump,*" Artif. Organs, 16: 518-22 (1992).

Waxman, K. et al., "*Implantable Programmable Insulin Pumps for the Treatment of Diabetes,*" Arch. Surg., 127: 1032-37 (1992).

Irsigler, K. et al.; "*Controlled Drug Delivery in the Treatment of Diabetes Mellitus,*" Crit. Rev. Ther. Drug Carrier Syst., 1(3): 189-280 (1985).

Colombo, A. et al., "*Intracoronary Stenting Without Anticoagulation Accomplished with Intravascular Ultrasound Guidance,*" Circulation 91: 1676-88 (1995).

Goldberg, S. et al.; "*Benefit of Intracoronary Ultrasound in the Development of Plamaz-Schatz Stents*", J. Am. Coll. Card. 24: 996-1003 (1994).

Virmani, R. et al., "*Histopathologic Evaluation of an Expanded Polytetrafluoroethylene Nitinol Stent Endoprosthesis in Canine Iliofemoral Arteries,*" JVIR, 10: 445-456 (1999).

Bates, J. B. et al., "*Thin Film Rechargeable Lithium Batteries for Implantable Devices,*" ASAIO J., 43: M644-M647 (1997).

Erickson, K. A. et al., "*Evaluation of a Novel Point-of-care System, the I-Stat Portable Clinical Analyzer,*" Clin. Chem. 39(2): 283-287 (1993).

Updike, S.J. et al., "*The Enzyme Electrode,*" Nature, 214: 986-8 (1967).

Clark, L.C. et al., "*Electrode Systems for Continuous Monitoring in Cardiovascular*," Ann. NY Acad. Sci., 102: 29-45 (1962).

Bindra, D. S. et al., "*Design and in vitro studies of a needle type glucose sensor for subcutaneous monitoring*," Anal. Chem., 63: 1692-6 (1991).

Moussy, F. et al., "*Performance of Subcutaneously Implanted needle-type glucose sensors employing a novel trilayer coating*," Anal. Chem., 65: 2072-7 (1993).

Davies, M.L., et al., "*Polymer membranes in clinical sensor application, Part 1: an overview of membrane function*," Biomaterials, 13: 971-89 (1992).

Pan, M., et al. "*Simple and Complex Stent Strategies for Bifurcated Coronary Arterial Stenosis Involving the Side Branch Origin*," Am. J. Cardiol., 83: 1320-25 (1999).

* cited by examiner

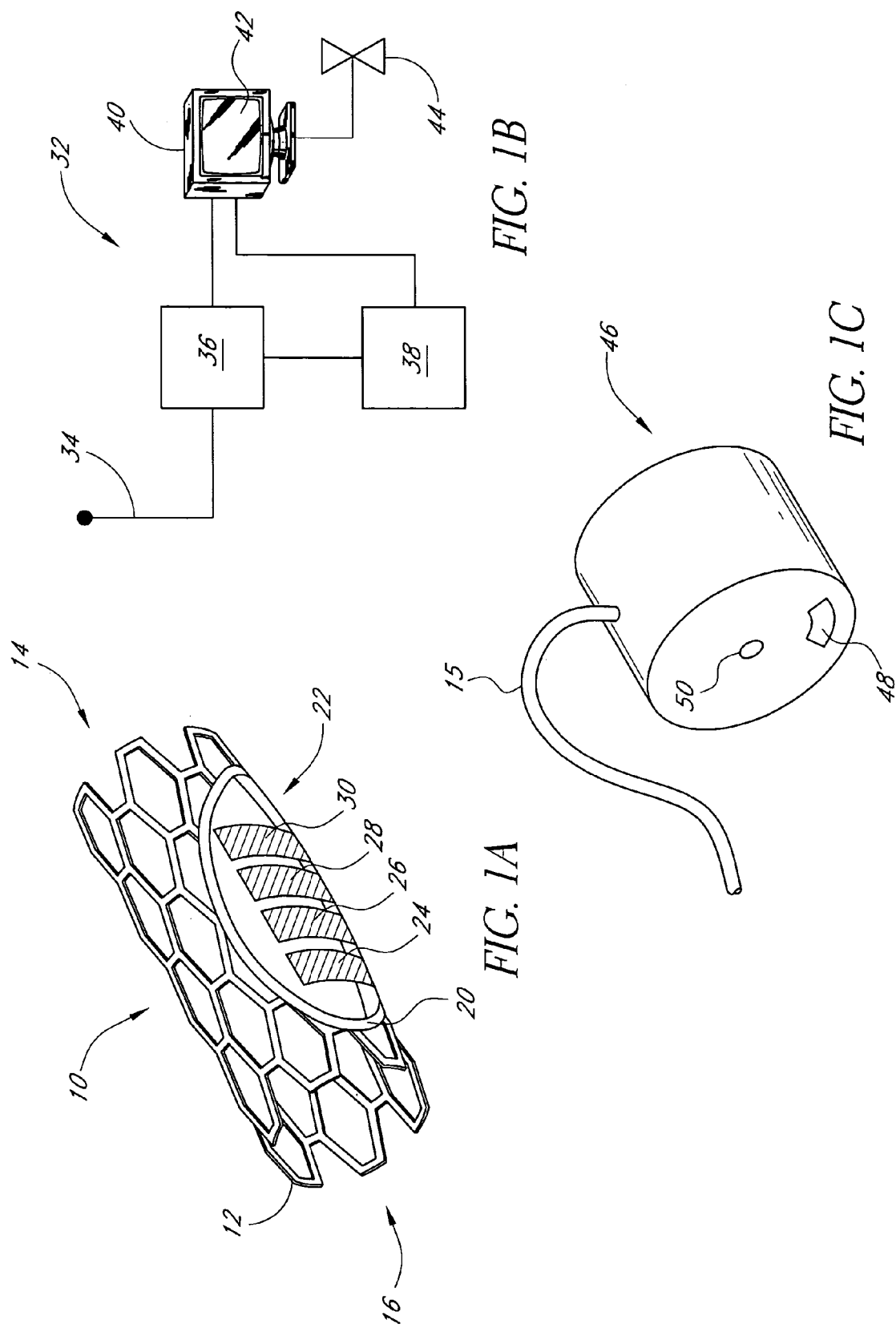

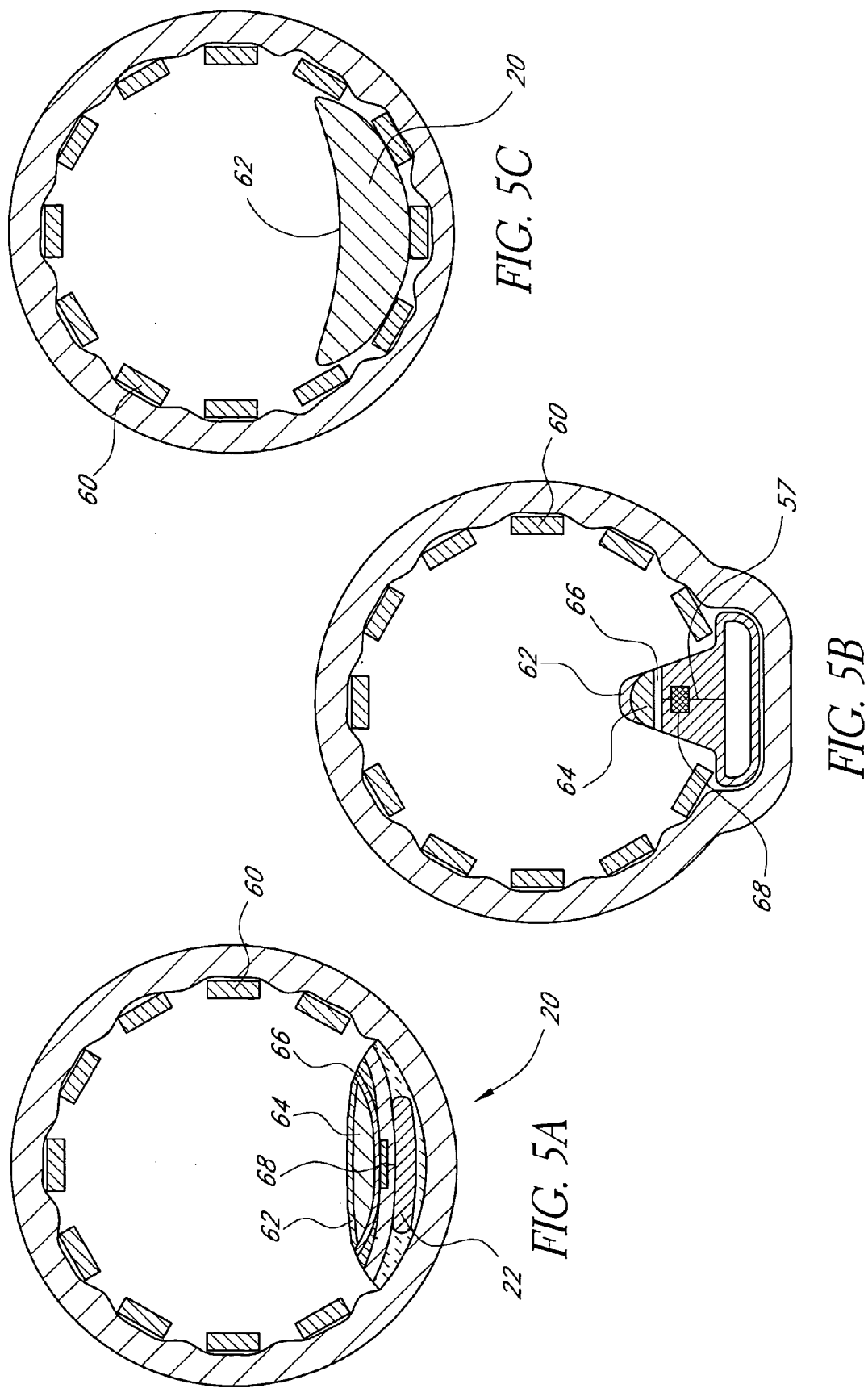

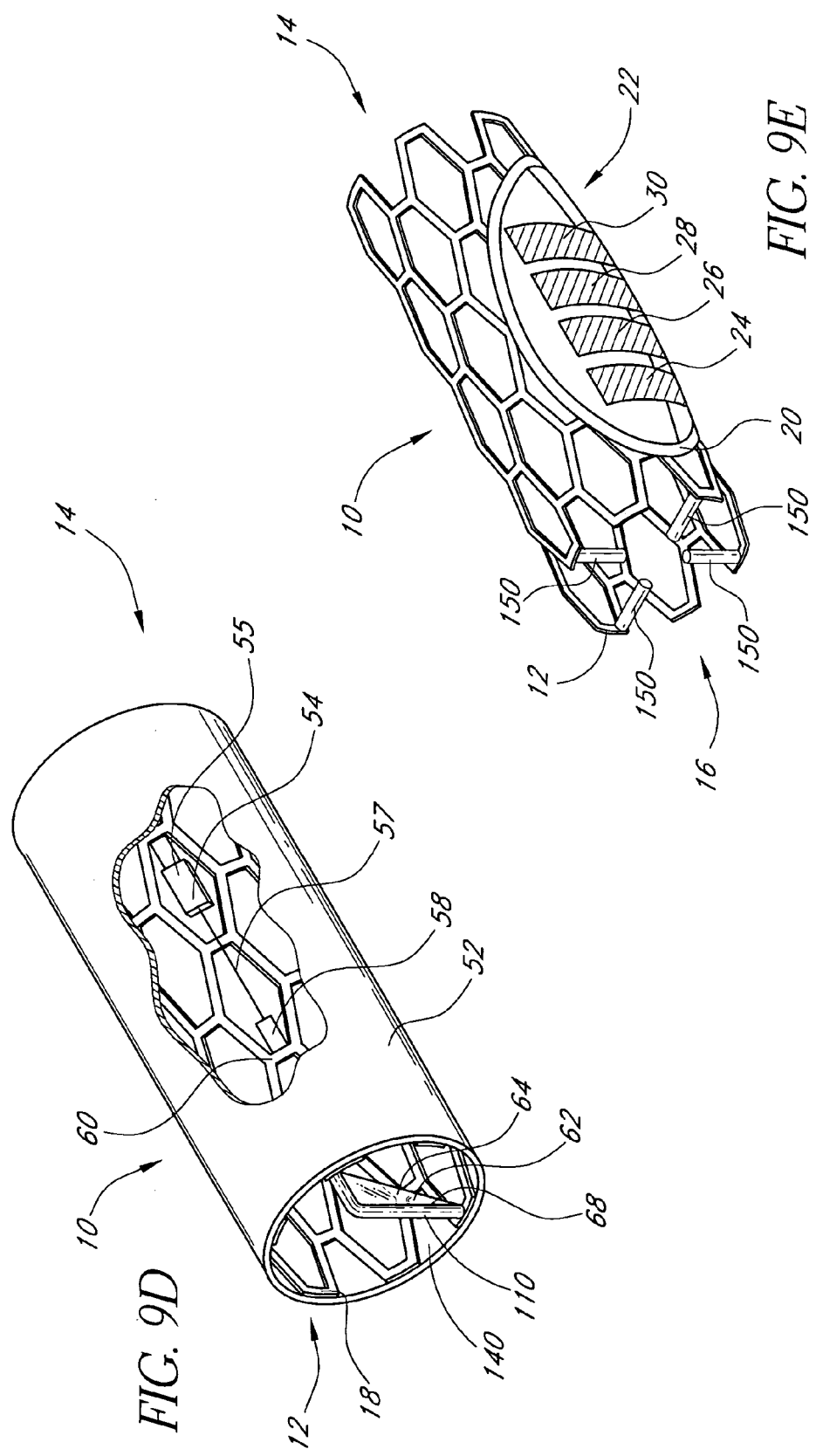

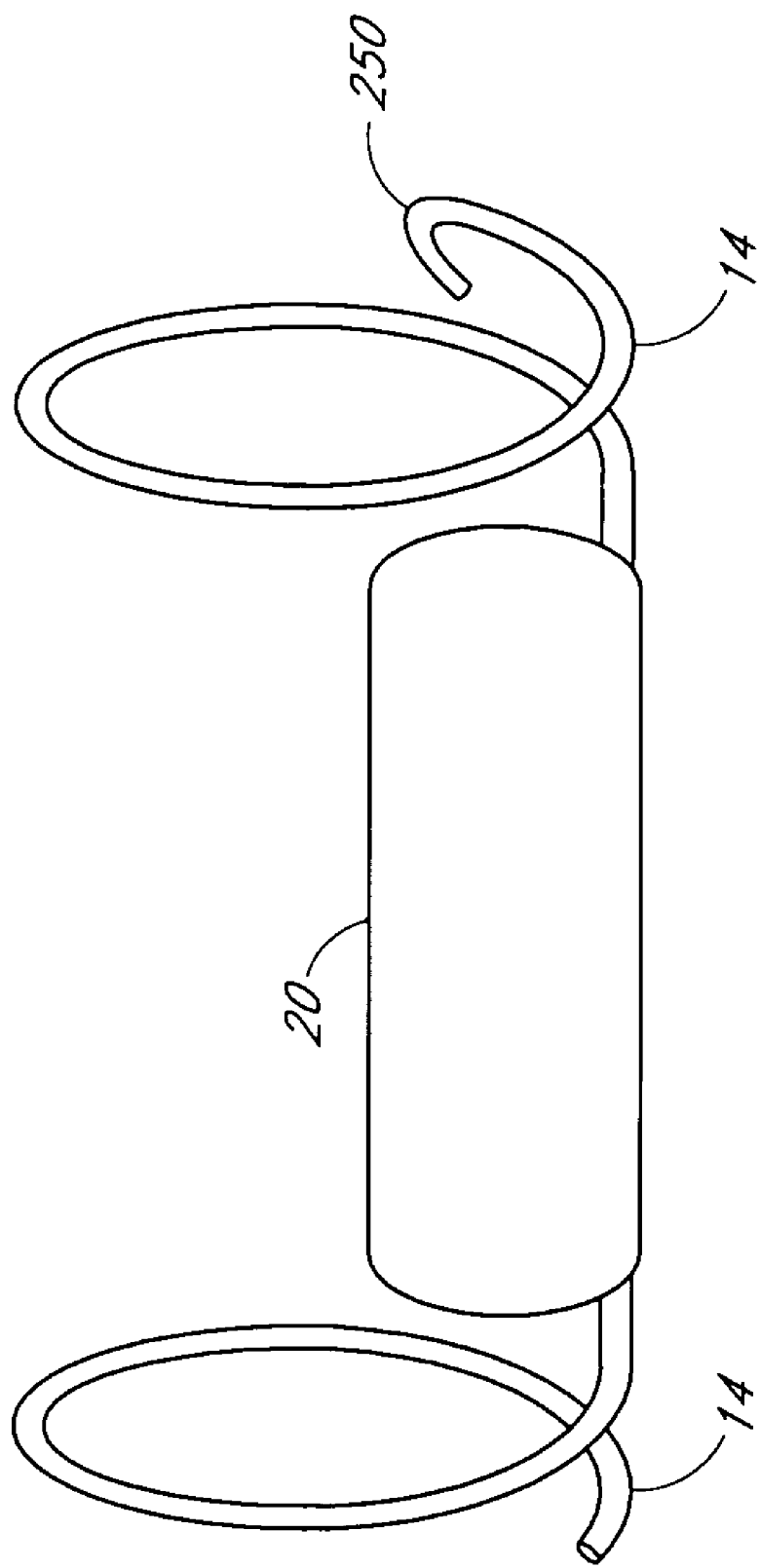

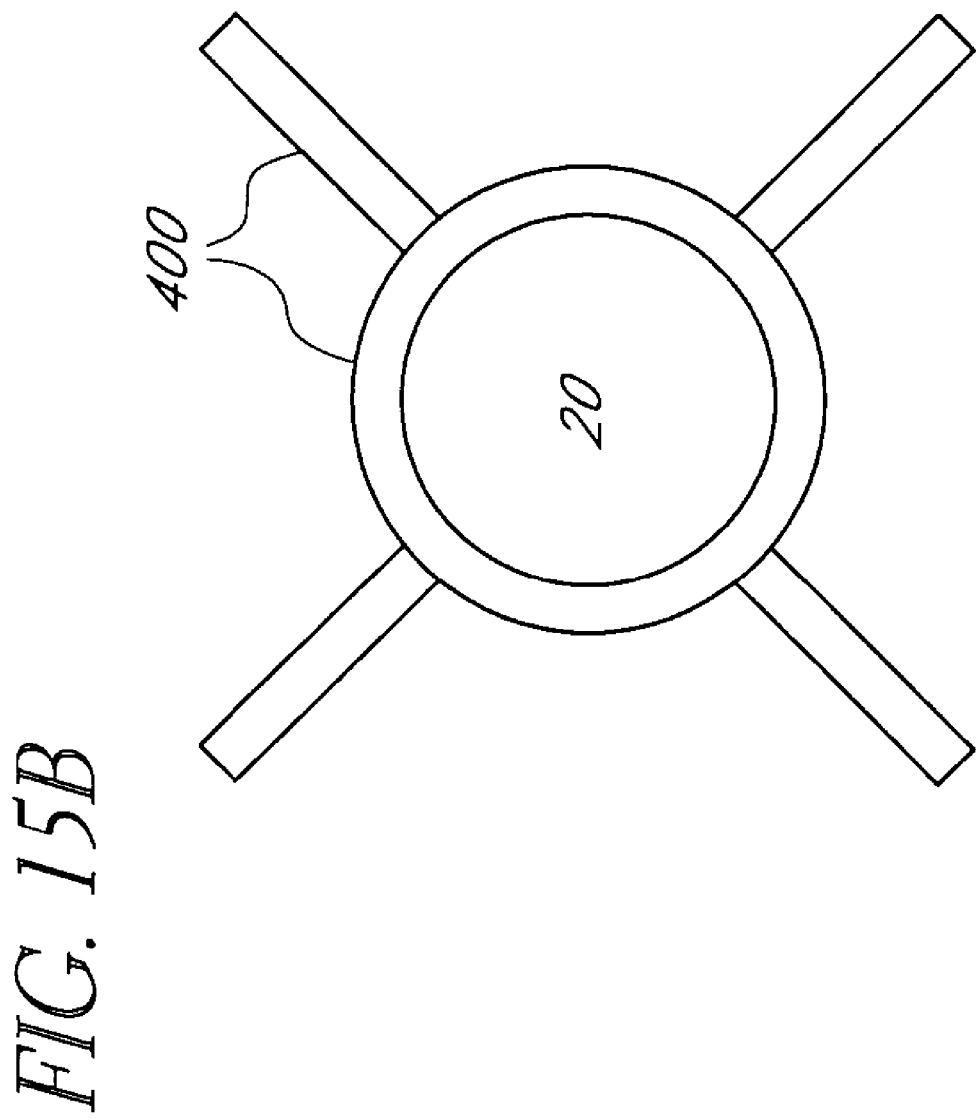

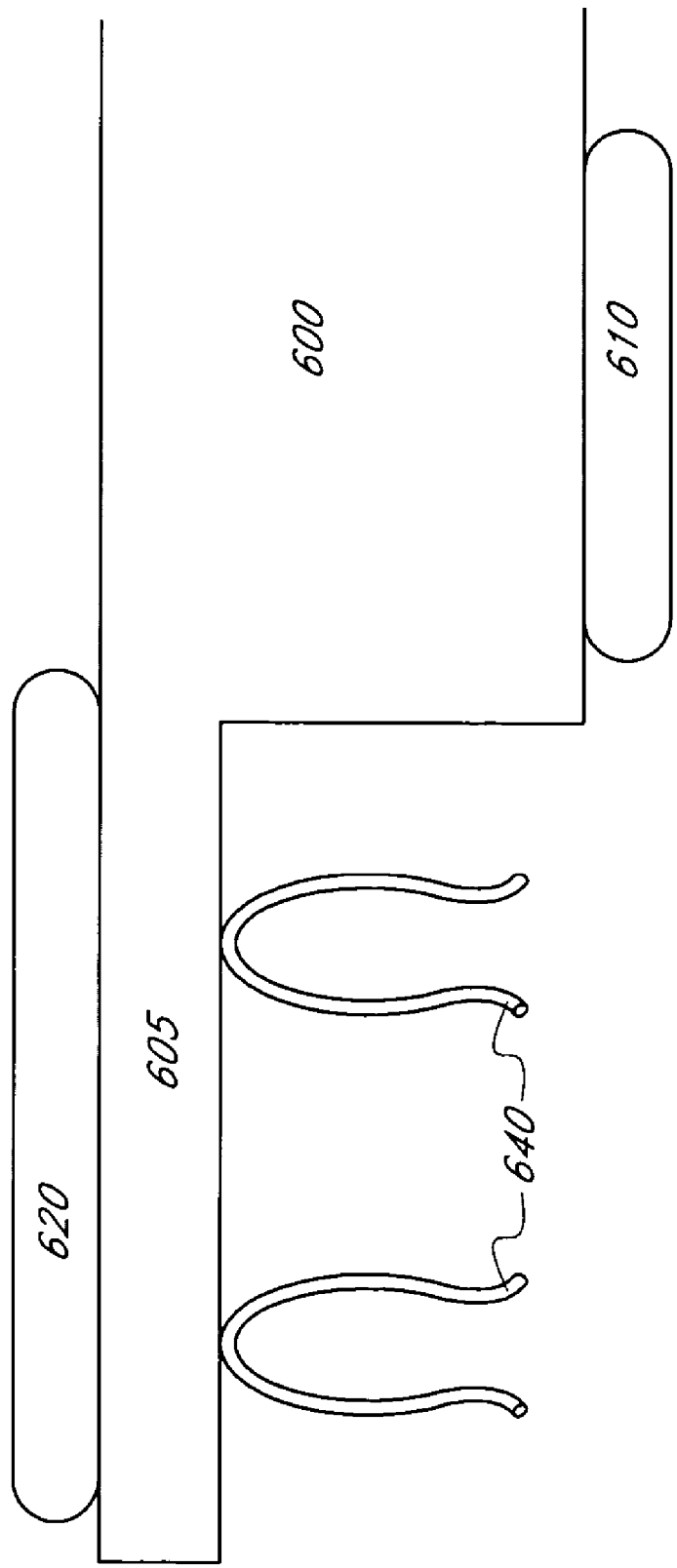

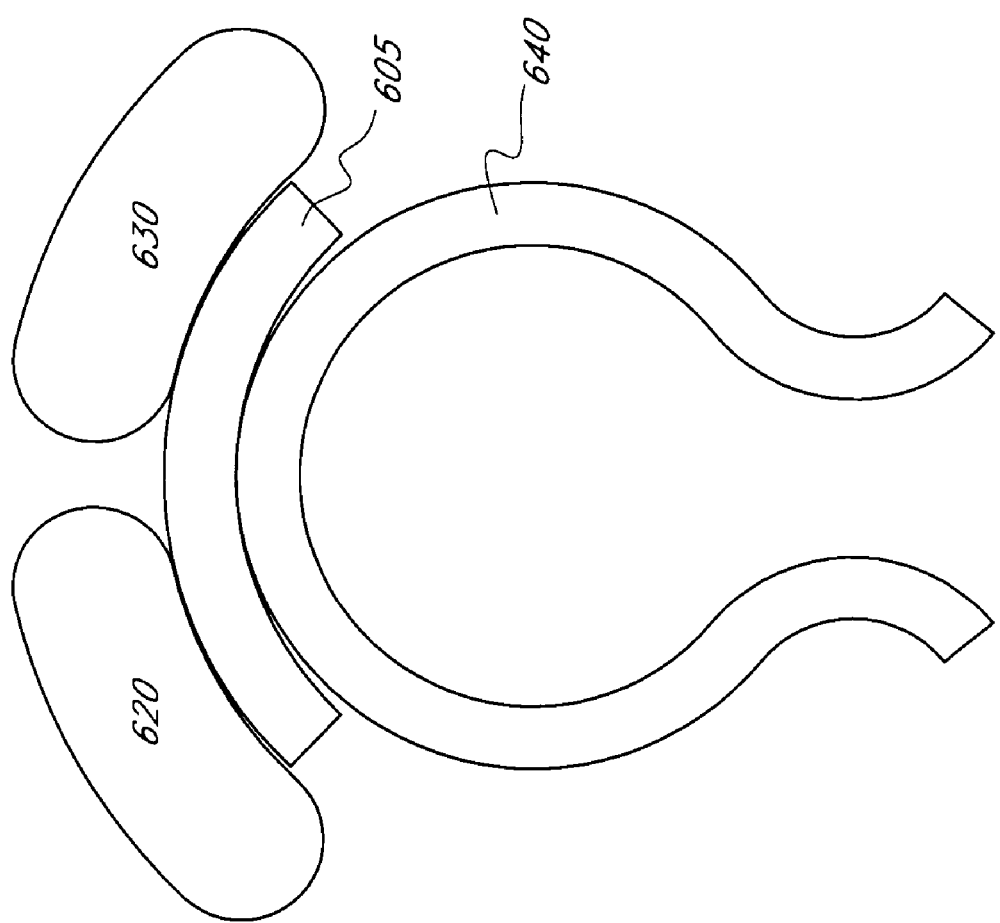

IMPLANTABLE, RETRIEVABLE, THROMBUS MINIMIZING SENSORS

BACKGROUND OF THE INVENTION

Field of the Invention

This is a continuation-in-part of U.S. patent application Ser. No. 10/217,202, filed Aug. 9, 2002 now U.S. Pat. No. 7,006,858, which is a continuation-in-part of U.S. patent application Ser. No. 10/041,036, filed Nov. 8, 2001 now U.S. Pat. No. 7,033,322, which is a continuation-in-part of U.S. patent application Ser. No. 09/571,702, filed May 15, 2000, now U.S. Pat. No. 6,442,413 issued on Aug. 27, 2002.

DESCRIPTION OF THE RELATED ART

The present invention generally relates to the use of sensors to monitor the concentration of a chemical species in bodily fluids. More specifically, the present invention relates to the use of sensors to monitor glucose levels, and/or other parameters in a fluid, including pressure or flow rate within a lumen of an endoluminal implant such as a stent or other type of endovascular conduit.

Diabetes mellitus is a serious medical condition affecting approximately 10.5 million Americans, in which the patient is not able to maintain blood glucose levels within the normal range (normoglycemia). Approximately 10% of these patients have insulin-dependent diabetes mellitus (Type I diabetes, IDDM), and the remaining 90% have non-insulin-dependent diabetes mellitus (Type II diabetes, NIDDM). The long-term consequences of diabetes include increased risk of heart disease, blindness, end-stage renal disease, and non-healing ulcers in the extremities. The economic impact of diabetes to society has been estimated by the American Diabetes Association at approximately $45.2 billion annually (Jonsson, B., *The Economic Impact of Diabetes*, Diabetes Care 21(Suppl 3): C7–C10, (1998)).

A major long-term clinical study, the Diabetes Control and Complications Trial, involving 1,441 patients with insulin-dependent diabetes mellitus (Type I diabetes) over a 10-year period from 1984–1993, demonstrated that by intensive therapy (frequent administration of either short- or long-acting insulin), these long-term consequences (retinopathy, nephropathy, and neuropathy) could be reduced ("*The Effect of Intensive Treatment of Diabetes on the Development and Progression of Long-Term Complications in Insulin-Dependent Diabetes Mellitus*," The Diabetes Control and Complications Trial Research Group, New Eng. J. Med., 329: 977–86 (1993)). Unfortunately, a major difficulty encountered during the trial was that intensive treatment also resulted in a higher incidence of low blood glucose levels (hypoglycemia), which was severe enough to result in coma or death, as compared to patients under conventional medical management.

Currently, diabetics must monitor their condition by repeatedly pricking their fingers in order to obtain blood samples for evaluation. The major drawback to self-monitoring of glucose is that it is discontinuous and therefore the number of glucose measurements performed is dependent on the motivation of the patient.

Existing analytical techniques and devices for in vitro glucose measurements have a high level of accuracy (the error can be <1%). Many of these routine methods are accepted as standards of comparison with new devices. Management of diabetes currently relies on these methods to control the disease and minimize complications.

There are two main disadvantages to these existing options. First, sampling even a minimal amount of blood multiple times per day is associated with risks of infection, nerve and tissue damage, and discomfort to the patients. Second, in the case of dynamic changes in glucose concentration, very frequent or even continuous measurements of blood glucose levels are required (Wilkins, E., et al., "*Glucose Monitoring: State of the Art and Future Possibilities*", Med. Eng. Phys. 18(4):273–88, (19916).

There are two main approaches to the development of a continuous blood glucose monitor. The first category is non-invasive sensors, which obtain information from physico-chemical characteristics of glucose (spectral, optical, thermal, electromagnetic, or other). The second category is invasive sensors. In this group, there is intimate mechanical contact of the sensor with biological tissues or fluids, because the device is placed within the body. (Wilkins, 1996).

Non-invasive sensor technology has focused on the absorption of the near-infrared (NIR) spectra by the analyte, in this case, glucose (See U.S. Pat. No. 5,945,676 to Khalil, et al., and U.S. Pat. No. 5,433,197 to Stark). Absorptions which occur in the NIR region are most often associated with overtone and combination bands of the fundamental vibrations of —OH, —NH, and —CH functional groups. As a result, most biochemical species will exhibit some absorption in the region of interest. Glucose measurements are usually performed in the spectra region from 4250 to 660 $cm^{-1}$. These highly overlapping, weakly absorbing bands were initially thought to be too complex for interpretation and too weak for practical application. Improvements in instrumentation and advances in multivariate chemometric data analysis techniques may allow meaningful results to be obtained from these complex spectra.

However, to date these devices are not particularly accurate even in the normal physiological range. A subject-dependent concentration bias has been reported. The temperature sensitivity of water absorption bands in the glucose-measuring region can be a significant source of error in clinical assays. In addition, the devices can also be affected by individual variations between patients at the measurement site. Skin location, temperature and tissue structure may affect the results, and decrease the accuracy of the reading.

Other investigators have looked into measurement of glucose from body fluids other than blood, such as sweat; saliva, urine, or tears. However, factors relating to diet and exercise can affect glucose levels in these fluids. In general, there is no strong correlation established between glucose concentration in the blood and in excreted fluids. The lag time between blood and excreted fluid glucose concentrations can be large enough to render such measurements inaccurate.

The continuous in vivo monitoring of glucose in diabetic subjects should greatly improve the treatment and management of diabetes by reducing the onus on the patient to perform frequent glucose measurements. Implanted glucose sensors could be used to provide information on continuously changing glucose levels in the patient, enabling swift and appropriate action to be taken. In addition, daily glucose concentration measurements could be evaluated by a physician. An implantable sensor could also provide an alarm for hypoglycemia, for example, overnight, which is a particular need for diabetics. Failure to respond can result in loss of consciousness and in extreme cases convulsive seizures. Similarly, a hyperglycemic alarm would provide an early warning of elevated blood glucose levels, thus allowing the patient to check blood or urine for ketone bodies, and to avert further metabolic complications. (Jaffari, S. A. et al., "Recent Advances In Amperometric Glucose Biosensors For In Vivo Monitoring", Physiol. Meas. 16:1–15 (1995)).

Invasive glucose sensors may be categorized based on the physical principle of the transducer being incorporated. Current transducer technology includes electrochemical, piezoelectric, thermoelectric, acoustic, and optical transducers.

In piezoelectric, thermoelectric, and acoustic (surface acoustic wave, SAW) sensors used for glucose measurement, an enzyme-catalyzed reaction is used to create a measurable change in a physical parameter detected by the transducer. The development of these sensors is at an early laboratory stage (Hall, E., *Biosensors*, Oxford University Press. Oxford, 1990). Optical sensors are based on changes in some optical parameter due to enzyme reactions or antibody-antigen reactions at the transducer interface. Based on the nature of the monitoring process, they are densitometric, refractometric, or colorimetric devices. At present, none of them meets the selectivity requirements to sense and accurately measure glucose in real physiological fluids.

There is a significant body of literature regarding the development of electrochemical glucose sensors. These generally incorporate an enzyme, which selectively reacts with glucose. Examples of enzymes, which selectively react with glucose, are glucose oxidase (GOD), hexokinase, glucose-6-phosphate dehydrogenase (G-6-PD), or glucose dehydrogenase. Hexokinase is an enzyme that catalyzes the phosphorylation of glucose by ATP to form glucose-6-phosphate and ADP.

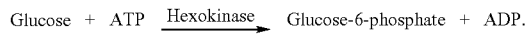

Monitoring the reaction requires a second enzyme, glucose-6-phosphate dehydrogenase, in the following reaction:

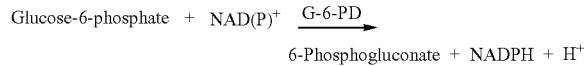

The formation of NADPH may be measured by absorbance at 340 nm or by fluorescence at 456 nm (Jaffari, 1995).

Glucose dehydrogenase is another enzyme, which may be used for monitoring glucose in the following reaction:

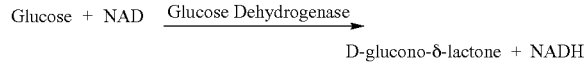

The NADH generated is proportional to the glucose concentration.

Glucose oxidase is the most commonly used enzyme reported in the literature. Its reaction is relatively simple, inexpensive, and may be monitored using a variety of techniques.

These advantages have led to the extensive use of this enzyme in clinical analysis as well as its incorporation in the majority of prototype biosensor configurations. The reaction of glucose with this enzyme is a two-stage reaction:

$$\text{-D-glucose} + \text{GOD(FAD)} \rightarrow \text{glucono-}\delta\text{-lactone} + \text{GOD(FADH}_2\text{)} \quad 1)$$

$$\text{GOD(FADH}_2\text{)} + \text{O}_2 \rightarrow \text{GOD(FAD)} + \text{H}_2\text{O}_2 \quad 2)$$

$$\text{glucono-}\delta\text{-lactone} + \text{H}_2\text{O} \rightarrow \text{gluconic acid} \quad 3)$$

The overall reaction is usually expressed as:

$$\beta\text{-D-glucose} + \text{O}_2 + \text{H}_2\text{O} \rightarrow \text{gluconic acid} + \text{H}_2\text{O}_2 \quad 4)$$

The reaction can therefore be monitored by the consumption of oxygen, the production of hydrogen peroxide, or the change in acidity due to the increase of gluconic acid.

One of the key reasons for using these types of sensor in an intravascular environment, rather than subcutaneously or in other bodily environments, is the need to provide closed-loop control for diabetic patients. This would provide insulin delivery based on the patient's actual glucose measurements, as opposed to providing insulin based on some inexact approximation of the patient's glucose levels. This would of great benefit to diabetic patients. There is a widely recognized time delay between glucose changes in venous blood, and subcutaneous glucose changes. This time delay can range from just a few minutes, to up to 30 min. However, the mathematical algorithm used to couple the glucose signal to the insulin delivery system cannot tolerate a very long time delay. In fact, two authors have presented data which suggested that 10 minutes is the maximum delay which can be tolerated in closed-loop insulin delivery systems (Parker R S, Doyle F, et al., "A Model-Based Algorithm for Blood Glucose Control in Type I Diabetic Patients" IEEE Trans. Biomed. Engr. 46(2):148–157 (1999), and Gough D et al, "Frequency Characterization of Blood Glucose Dynamics" Ann Biomed Engr 31:91–97 (2003).) Longer time delays can cause the controller to become unstable, potentially creating life-threatening issues for the patient, such as delivery of extra insulin when blood glucose levels are falling rapidly.

Despite the foregoing and other efforts in the art, a suitable continuous in dwelling glucose sensor has not yet been developed.

A critical factor in the design of an implanted sensor is the anatomical site in which it is implanted. A few investigators have developed monitoring systems, which can be placed within the vascular system. Armour et al. ("*Application of Chronic Intravascular Blood Glucose Sensor in Dogs*", Diabetes 39:1519–26 (1990)) implanted a sensor into the superior vena cava of six dogs for a period of up to 15 weeks with relative success. However, due to the risks of thrombosis and embolization, the majority of investigators have focused on subcutaneous implantation.

A major drawback to subcutaneous implantation is the body's defense against foreign objects: the "foreign-body response". In this host response, if an object cannot be removed by the inflammatory response, foreign-body giant cells will form a "wall" around the object, which is subsequently followed by the formation of a fibrous capsule. If the object is a blood glucose sensor, it will no longer be in intimate contact with body fluids, and the signal will drift and stability will be lost. There are numerous reports of sensor stability being lost in about a week (Wilson, G. S., et al., "*Progress Towards The Development Of An Implantable Sensor For Glucose*", Clin. Chem. 1992 38:1613–7, and Kerner, et al., "*A Potentially Implantable Enzyme Electrode For Amperometric Measurement Of Glucose*", Horm.

Metab. Res. Suppl. Ser. 20: 8–13 (1988)). Updike et al. (Updike, Stuart J., et al., "*Enzymatic Glucose Sensors: Improved Long-Term Performance In Vitro And In, Vivo*", ASAIO J., 40: 157–163 (1994)) reported on the subcutaneous implantation of a sensor which was stable for up to 12 weeks, however, this evaluation was only performed in three animals.

Recent clinical studies have also demonstrated that implantable insulin pumps are feasible for implantation for over one year (Jaremko, J. et al., "*Advances Towards the Implantable Artificial Pancreas for Treatment of Diabetes*," Diabetes Care, 21(3): 444–450 (1998)). The research was inspired by the goal of the development of the artificial pancreas, and promising initial clinical trials using implantable insulin pumps. At this point in time, development of implantable insulin pumps is at a very advanced stage, with units being implanted for over 2 years in canines (Scavani et al., "*Long-Term Implantation Of A New Programmable Implantable Insulin Pump*," Artif. Organs, 16: 518–22 (1992)) and in 25 patients for up to 3 years (Waxman, et al., "*Implantable Programmable Insulin Pumps For The Treatment Of Diabetes*", Arch. Surg., 127: 1032–37 (1992)).

A number of wearable insulin pumps are described by Irsigler et al. ("*Controlled Drug Delivery In The Treatment Of Diabetes Mellitus*," Crit. Rev. Ther. Drug Carrier Syst., 1(3): 189–280 (1985)). Thus, it should be relatively straightforward to couple a long-term implantable glucose sensor as described in this disclosure, to an insulin pump to optimize glycemic control for the patient.

In another aspect of this invention, it is possible to apply the principles discussed above to the direct, continuous monitoring of arterial blood gases (ABG). Arterial blood gas values such as $pO_2$, $pCO_2$, and pH are the most frequently ordered laboratory examinations in the intensive care setting and the operating room (C. K. Mahutte, "Continuous intra-arterial blood gas monitoring," Intensive Care Med (1994) 20:85–86). In the intensive care unit (ICU), ABG is typically monitored once a day, and additional measurements are only made once the patient has experienced a deleterious event. Limited additional sampling is performed at the discretion of a physician or nurse. There can be a significant time delay between the time the tests are ordered, and the results are returned (E. E. Roupie, "Equipment Review: Continuous assessment of arterial blood gases," Crit Care 1997 1(1): 11–14).

In the case of continuous monitoring, significant changes in ABG values or trends would cause a rapid, therapeutic response on the part of the physician, so potentially catastrophic events could be avoided. Continuous, non-invasive monitoring techniques such as pulse oximetry and continuous capnography have been introduced for this reason. Unfortunately, these devices are not always accurate in cases such as shock, hypothermia, or during the use of vasopressors. Further, pulse-oximetry does not measure oxygen tension.

A number of attempts have been made to develop improved arterial blood gas monitors. There are two basic types of arterial blood gas monitors. In the first type, termed extra-arterial blood gas (EABG) monitors, the patient's blood gas values are measured from a sample in the arterial catheter. This can significantly reduce the time delay in obtaining results, as compared to sending the sample to a laboratory. However, it is an on-demand system, not a continuous one, so the frequency of sampling is once again dependent upon the physician or nurse.

The second type of device, known as an intra-arterial blood gas (IABG) monitor, is inserted directly into the arterial blood. However, the consistency and reliability of these LABG monitors have not been clinically acceptable because of problems associated with the intra-arterial environment. (C. K. Mahutte, "On-line Arterial Blood Gas Analysis with Optodes: Current Status," Clin. Biochem 1998; 31:119–130).

In another aspect of this invention, implantable sensors capable of monitoring hemodynamic conditions over extended periods of time may be useful in patients with heart failure. Such measurements have traditionally been restricted to cardiac catheterization laboratories and intensive care units (ICU's). Measurements cannot be made easily in an ambulatory setting, or under conditions of cardiac loading, such as exercise. Ohlsson et al (Ohlsson A, et al., "Continuous ambulatory monitoring of absolute right ventricular pressure and mixed venous oxygen saturation in patients with heart failure using an implantable hemodynamic monitor: Results of a one year multicentre feasibility study," Eur Heart J 22:942–954 (2001)) describe implantation of a pressure sensor and an oxygen sensor, the IHM-1, Model 10040 (Medtronic, Inc.). However, in this study, 12 out of 21 oxygen sensors failed within the first 6 months of implantation. A fibrinous coating covered one of the sensors, and it was believed that this was responsible for sensor failure. In addition, surgical implantation of this pacemaker-style device requires a 2–3 hour procedure in the operating room, which is more costly than a catheterization procedure to insert a pressure sensor. Data from this study, however, points to the importance of long-term, continuous pressure monitoring, as opposed to one-time measurements using standard cardiac catheterization techniques.

In another aspect of this invention, the sensor may be used for measuring flow rates within a vessel. Congestive heart failure affects more than 5 million persons in the United States, and the rate is increasing as people age and more of them survive heart attacks. Finding the right treatment often involves a trial-and-error process, with the physician trying different combinations of drugs and different dosages to produce the best results. That means repeated blood pressure and flow measurements and invasive cardiac catheterization procedures to measure the effects on the heart.

In U.S. Pat. No. 6,053,873 issued Apr. 25, 2000 to Govari et al, a method of monitoring flow rates within a stent is described. In particular, the use of ultrasonic sensors to monitor blood flowrates is described. However, due to the change in composition and thickness of the biological material present on the sensor surface, the boundary conditions at the sensor may change over time. Initially, the sensor surface, which may be calibrated against blood, may become covered with a layer of thrombus over time. Subsequently, the thrombus will transform into fibrous tissue, affecting the absorption of the ultrasound signal. Blood may have an ultrasound absorption level similar to water, of around 0.002 dB/MHz cm, while the fibrous tissue layer may have an absorption level similar to muscle, of around 2 dB/MHz cm. Thus, such a sensor may require periodic re-calibration. Unfortunately, the re-calibration process requires an invasive cardiac catheterization procedure, in which flow rates are determined using ultrasound, thermodilution, or the Fick method. In order to avoid additional interventional procedures, the fouling-resistant approach described herein may be valuable.

In U.S. Pat. No. 6,309,350 to VanTassel, et al., issued Oct. 30, 2001, a sensor is described which is anchored in the wall of the heart, or in a blood vessel. However, no mention is made of the difficulty with sensor fouling due to thrombus formation, or how to compensate for that. Pressure sensors would require recalibration as the softer thrombus transforms into neointimal tissue, or as the thickness of the encapsulating tissue layer changes. While the device could be initially calibrated during implantation, it would need to be recalibrated over time. Because recalibration requires an invasive cardiac catheterization procedure, it would be desirable to avoid this if at all possible.

In addition, VanTassel et al. suggest the use of standard thermodilution methods to determine flow rates. Thermodilution is normally performed by injection of either room temperature or iced saline through a catheter. However, it is desirable to avoid re-interventions if possible. Therefore, standard thermodilution methods are less desirable than the current invention. In addition, it is impractical to use the sensor in the standard method, i.e., by locally cooling the blood, because chilling units are impractically large for implantation as a sensor. Further, thermodilution methods would be inaccurate if the thermocouple or sensing element was covered by a relatively thick layer of cells. This would be especially true if only a small temperature rise were introduced into a large volume of flowing blood, such as in the pulmonary artery. Larger temperature rises (>2.5° C.) would cause local tissue damage.

Stroke is the third most common cause of death in the US and Europe. There are approximately 1 million acute ischemic strokes in Europe annually. Stroke survivors are often significantly disabled, and must undergo extensive rehabilitation. The estimated short term costs of a stroke are $13,649 per patient, and the long term costs are $45,893 for a minor stroke and $124,564 for a major stroke (Caro, J J, et al., "Stroke Treatment Economic Model (STEM): Predicting Long-term Costs from Functional Status", Stroke 1999; 30:2574–2579). The direct and indirect economic impact of stroke in the US is estimated to be $43.3 billion. (US). According to the National Institutes of Health recombinant tissue-type plasminogen activator trial, if stroke could be treated in the first hours after the stroke occurs, the damage can be minimized (National Institute of Neurological Disorders and Stroke. rt-PA Stroke Study Group. "Tissue Plasminogen Activator for acute ischemic stroke." N Engl J Med 1995; 333:1581–1587). However, if treatment is delayed, then the damage becomes worse. Unfortunately, symptoms of stroke are not widely recognized, and significant delays in treatment are introduced by the failure to recognize the problem.

Risk factors such as high blood pressure, cholesterol, smoking, obesity; and diabetes increase the chances that an individual will suffer a stroke. Patients with significantly increased risks of stroke include patients with atrial fibrillation, coronary heart disease, asymptomatic carotid stenosis, previous stroke, or transient ischemic attack (TIA). In the latter subsets, approximately 25% of stroke survivors experience a recurrent stroke within five years, and among patients with TIA, the risk for stroke is 5% within 48 hours, 12% within 1 year, and up to 30% within 5 years.

In the acute phase of cerebral infarction, a great deal of experimental data suggests that free radicals, including superoxide, hydroxy radical, and nitric oxide (NO) are one of the most important factors causing brain damage. J. Rodrigo, D, et al (Histol. Histopathol. 17, 973–1003 (2002)) have observed that most of the morphological and molecular changes associated with ischemic damage were prevented by treatment with inhibitors of NO production. In addition, there is a significant increase in the concentration of NO following cerebral ischemia. There is also significant NO release in hemorrhagic stroke. (Chen H H, et al, "Low cholesterol in erythrocyte membranes and high lipoperoxides in erythrocytes are the potential risk factors for cerebral hemorrhagic stroke in human" Biomed Environ Sci. 2001 September; 14(3):189–98). Therefore, the detection of NO in the acute phase of ischemic or hemorrhagic stroke would provide an early detection method for stroke, allowing treatment to be performed as promptly as possible by the physician or health-care provider.

While animal studies have demonstrated an increase in nitric oxide shortly after ligation of the middle cerebral artery (Lin, S Z, et al., "Ketamine Antagonizes Nitric Oxide Release From Cerebral Cortex after Middle Cerebral Artery Ligation in Rats", Stroke 1996; 27:747–752) it is possible that the nitric oxide may be converted to metabolites such as nitrites and nitrates by the time it reaches monitoring sites which are distant from the site of the stroke. It has also been demonstrated that the level of these metabolites are significantly higher in cerebrospinal fluid (CSF) at the time stroke patients are admitted to the hospital, which is often many hours after the stroke (Castillo, J. et al., "Nitric Oxide-Related Brain Damage in Acute Ischemic Stroke", Stroke 2000; 31:852–857). It has further been demonstrated that there is a significant increase in levels of nitric oxide, nitrite, and nitrate ions in the jugular vein of a rat, immediately following induction of ischemic stroke (Suzuki, M, et al., Brain Research 951 (2002) 113–120).

Notwithstanding the extensive efforts in the prior art, however, there remains a need for an implantable blood glucose sensor for implantation in a blood vessel, which can provide useful blood glucose readings for an extended period of time, without material interference from thrombus formation, embolization, or other foreign body response. Preferably, the sensor is capable of continuous or near continuous monitoring, and driving an implantable insulin pump and/or making blood glucose data available to the patient or medical personnel.

SUMMARY OF THE INVENTION

The present invention generally relates to the use of sensors to monitor the concentration of a chemical species in bodily fluids, and more specifically, to a novel sensor configuration to monitor glucose levels in a body vessel. The device is an implantable sensor, which is delivered to the patient's vascular system preferably transluminally via a catheter, using a stent or stent-graft as a platform. One feature of the device is that the sensor surface is placed at the apex of the luminal surface of a streamlined housing, so that the shear rate at the sensor/blood interface is sufficient to minimize the thickness of the formed thrombus layer. In this manner, significant tissue deposition or encapsulation due to potential fibrotic reactions is minimized, and transport of glucose to the sensor is not altered over time.

Thus, there is provided in accordance with one aspect of the present invention a blood glucose detector for implantation within a blood vessel. The blood glucose detector comprises a support, having a first side for contacting the wall of the vessel and a second side for facing radially inwardly towards the center of the vessel. A sensor is carried by the support, and the sensor has a sensing surface thereon. The sensing surface is spaced radially inwardly from the first side by a distance of at least about 0.2 to 2.5 mm, such that the velocity of blood in the vessel inhibits obstruction of the sensing surface. Preferably, the distance is at least about 0.5 mm. The blood glucose detector further comprises a transmitter on the support, for transmitting information from the sensor to an external receiver. In one embodiment, the support comprises an expandable tubular body. The tubular body may be either a balloon expandable or a self-expandable component such as a stent. The tubular body may be further provided with a tubular sheath on the radially inwardly directed surface and/or the radially outwardly directed surface. In one embodiment, the sensor comprises an analyte permeable membrane and an enzyme gel layer.

In accordance with another aspect of the present invention, there is provided a method of prolonging the useful life of a sensor in a blood vessel. The method comprises the steps of providing a sensor having an analyte sensing surface thereon, and positioning the sensor at a site in a blood vessel such that the sensing surface is positioned radially inwardly from the vessel wall by a sufficient distance that the blood flow shear rate at the sensing surface substantially delays obstruction of the sensing surface. Preferably, the positioning step comprises carrying the sensor on a catheter and transluminally advancing the catheter to the site.

In accordance with a further aspect of the present invention, there is provided an implantable sensor for sensing the presence of an analyte in a vessel. The sensor comprises a tubular support structure for anchoring the sensor in a vessel. The support has a sidewall with a luminal side facing towards the center of the vessel and an abluminal side facing towards the wall of the vessel. A sensor housing is carried by the support structure, the housing having a streamlined exterior configuration to minimize blood flow turbulence. A power supply and electrical circuitry are provided in the housing, and a sensing surface carried by the housing is exposed to the exterior of the housing. The sensing surface is positioned on the radially inwardly most portion of the luminal side of the housing.

In accordance with a further aspect of the present invention, there is provided an implantable sensor for sensing the presence of an analyte in a vessel that can be retrieved. The sensor comprises a support structure for anchoring the sensor in a vessel. The sensor further comprises a snareable member connected to the sensor that allows allow for removal of the sensor in a catherization procedure. In one embodiment, the snareable member is a hook.

In accordance with a further aspect of the present invention, a method for retrieving an implanted sensor is provided. Under fluoroscopic guidance, a guiding catheter of sufficient diameter so as to be able to accommodate the retrieved sensor and its anchoring platform is inserted. A snare is inserted through the guiding catheter and is guided to a sensor hook. The snare grasps the sensor hook and the sensor collapses into a retrieval catheter. The sensor and guiding catheter are simultaneously withdrawn from the patient's body.

In accordance with a further aspect of the present invention, another method for retrieving an implantable sensor on a support is provided. Under fluoroscopic guidance, a catheter with a clip is positioned so that the clip is adjacent to an sensor attached to a stent. A balloon attached to the catheter is inflated so that the clip is forced around the sensor. After deflating that balloon, another balloon is inflated so that the clip pulls the sensor away from the stent, thus separating the sensor therefrom.

In accordance with a further aspect of the present invention, there is provided an implantable immunosensor. The immunosensor comprises a support structure. The immunosensor produces an electrical signal representative of a reaction between an analyte and an antigen.

In another aspect of this invention, the sensor may be an infrared sensor placed either intraluminally or extraluminally in a blood vessel. The infrared sensor produces an electrical signal indicative of the concentration of chemical compounds in blood.

In accordance with a further aspect of the present invention, there is provided an implantable blood gas monitor. The blood gas monitor produces an electrical signal indicative of the partial pressure of dissolved blood gases or pH.

In accordance with a further aspect of the present invention, there is provided an implantable ion-selective electrode. The ion selective electrode produces an electrical signal indicative of the concentration of electrolytes in blood.

In accordance with a further aspect of the present invention, there is provided an implantable pressure sensor. The pressure sensor produces an electrical signal indicative of the pressure in the vessel.

In accordance with a further aspect of the present invention, there is provided an implantable flow sensor. The flow sensor produces an electrical signal indicative of the flowrate in the vessel.

In accordance with a further aspect of the present invention, sensor for implantation within a blood vessel that minimizes the formation of thrombus. The sensor comprises a support, having a first side for contacting the wall of the vessel and a second side for facing radially inwardly toward the center of the vessel and a sensor carried by the support and having a sensing surface thereon. The sensing surface of the sensor is spaced radially inwardly from the first side and includes a layer that minimizes the formation of thrombus. The sensor can include a transmitter on the support, for transmitting information from the sensor to an external receiver. The layer can be an anticoagulant (such as heparin), a hydrogel (such as poly(ethylene glycol), poly(N-vinyl pyrrolidone), or poly(hydroxyethylmethacrylate), or can release a pharmacological agent that inhibits cell proliferation or migration.

In accordance with a further aspect of the present invention, there is provided an implantable sensor for sensing the presence of nitric oxide or a nitric oxide metabolite in a vessel. The sensor comprising a support structure, a sensor housing carried by the support structure, and a sensing surface exposed to the surrounding environment. The sensor can detect nitric oxide or a nitric oxide metabolite and can be implanted for a period of at least one week. The support structure can be a stent or a catheter.

Further features and advantages of the present invention will become apparent to those of skill in the art in view of the detailed description of preferred embodiments which follows, when considered together with the attached drawings and claims.

BRIEF DESCRIPTIONS OF THE DRAWINGS

FIG. 1A is a perspective view of an expanded stent with an embedded sensor housing on its abluminal side.

FIG. 1B is a block diagram of remote circuitry for an external monitoring device.

FIG. 1C is a diagram of a wearable or implantable insulin pump.

FIG. 5A is a cross-sectional view through a stent showing one mounting configuration of an embedded sensor in accordance with one embodiment of the present invention.

FIG. 5B is a cross-sectional view as in FIG. 5A of a stent with an alternate configuration for the embedded sensor.

FIG. 5C is a cross-sectional view as in FIG. 5A of a stent with an embedded sensor mounted completely on the luminal side of the stent.

FIG. 9D is a perspective partial cut away view of a stent sensor device surrounded by a sheath with a transducer partially across the cross-section of the stent.

FIG. 9E is a perspective view of an expanded stent with an embedded sensor housing on its abluminal side and four perpendicular transducers placed partially across the cross-section of the stent.

FIG. 14A is a diagram of an expanded anchoring platform or stent with an embedded sensor housing on its luminal side, and containing a hook with which the device can be retrieved.

FIG. 15B is an end view diagram of an expanded anchoring platform with an embedded sensor, which is placed centrally in a vessel, and containing a hook on the sensor housing with which the device can be retrieved.

FIG. 17A shows a side view of a retrieval catheter designed for removing a sensor at the end of its life.

FIG. 17B shows an end view of a retrieval catheter designed for removing a sensor at the end of its life.

DETAILED DESCRIPTION OF THE PREFERRED EMBODIMENT

Figure 1E:
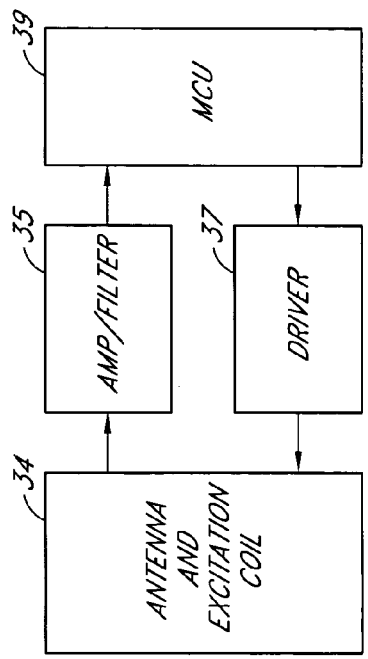
FIG. 1E is a block diagram of the remote measurement unit.

In accordance with the present invention, an intraluminal blood glucose sensor is provided on a support structure such as a modified stent of the type implanted following percutaneous transluminal coronary angioplasty (PTCA) for the treatment of atherosclerosis. Atherosclerosis is the build-up of fatty deposits or plaque on the inner walls of a patient's arteries. These lesions decrease the effective size of the artery lumen and limit blood flow through the artery, prospectively causing a myocardial infarction or heart attack if the lesions occur in coronary arteries that supply oxygenated blood to the heart muscles. In the angioplasty procedure, a guide wire is inserted into the femoral artery and is passed through the aorta into the diseased coronary artery. A catheter having a balloon attached to its distal end is advanced along the guide wire to a point where the stenotic lesions limit blood flow through the coronary artery. The balloon is then inflated, compressing the lesions radially outward against the wall of the artery and substantially increasing the size of the arterial lumen, to improve blood circulation.

Increasingly, stents are being used in place of or in addition to PTCA for treatment of atherosclerosis, with the intent of minimizing the need to repeatedly open a stenosed artery. Although a number of different designs for stents exist in the prior art, all are generally configured as elongate cylindrical structures that can assume two different states, one having a substantially greater diameter than the other. A stent is implanted in a patient's vascular system using an appropriate delivery system. There are two basic types of stents. The first type is termed "balloon expandable", and refers to sterits that are expanded radially outward due to the force from an inflated angioplasty balloon, such as the Palmaz-Schatz stent, the Gianturco-Roubin stent, and the Strecker stent. The second type is termed "self-expandable", and refers to and those that are self-expanding, such as the Hemobahn™ and SMART Stent™ (made of nickel titanium memory alloy), and the Wallstent (made of Elgiloy).

Typically, a stent carried by a delivery catheter is advanced through a guide catheter to a site within the patient's artery. For the balloon expanded type, after the introducer sheath is retracted, a balloon disposed inside the stent is inflated to a pressure ranging from about six to ten atmospheres. The force produced by the inflated balloon expands the stent radially outward beyond its elastic limit, stretching the vessel and compressing the lesion to the inner wall of the vessel. A self-expanding stent expands due to spring force following its positioning within the artery, after a restraining sheath is retracted from the compressed stent. Following the expansion process, if the balloon expandable type is used, the balloon is deflated and removed from inside the stent and the catheter and other delivery apparatus is withdrawn. The lumen through the vessel should be substantially increased, improving blood flow.

After a stent or other endoluminal device is implanted, a clinical examination and either an angiographic or ultrasonographic morphological procedure is performed to evaluate the success of the procedure in opening the diseased artery or vessel. These tests are typically repeated periodically, e.g., at six-month intervals, because restenosis of the artery may occur.

Although the sensor of the present invention may be carried by any of a wide variety of intraluminal support structures, balloon expandable or self-expandable stents are preferred by the present inventor. In general, the stent may be modified from those intended for supporting a treatment site following angioplasty, in view of the preferred placement in a healthy section of the vessel as is discussed in greater detail below. In addition, the wall of the stent may be modified to support the sensor, as is also discussed in greater detail below. As well as providing a useful support structure with known deployment characteristics, a stent provides a useful platform for a variety of additional reasons. For example, it is impractical to pass an electronic conductor through the wall of an artery or vessel to monitor the condition of an implanted sensor for long periods of time. Also, any active glucose sensor would likely be energized with electrical power. Again, it is less practical to supply power to such a sensor through any conductor that perforates the vessel wall or that passes outside the patient's body.

In addition to stents, the generic term endoluminal implant encompasses stent-grafts, which are also sometime referred to as "covered stents." A stent-graft is a combination of one or more stents and a synthetic graft that is typically implanted at a desired point in a vessel using an endoscopic approach. The stent is attached either to the ends or throughout the body of the synthetic graft, and is used to hold the graft in position. Sometimes, hooks are provided on the stent to ensure that the graft remains in the desired position within the vessel. Clearly, it would also be desirable to monitor the status of glucose and other parameters through a stent graft, just as noted above in regard to a stent.

Endoluminal implants are used in other body passages in addition to blood vessels. For example, they are sometimes used to maintain an open lumen through the urethra, or through the cervix. A stent placed adjacent to an enlarged prostate gland can prevent the prostate from blocking the flow of urine through the urinary tract. Tracheal and esophageal implants are further examples of endoluminal implants. In these and other uses of an endoluminal implant, provision for monitoring parameters related to the status of flow and other conditions in the patient's body would be desirable. Information provided by monitoring such parameters can enable more effective medical treatment of a patient.

A number of factors will affect the function of a glucose sensor implanted within a blood vessel. As with stents, the device should be designed to minimize the risk of thrombosis and embolization. Thus, slowing or stoppage of blood flow at any point within the lumen should be minimized. Colombo et al. ("*Intracoronary Stenting Without Anticoagulation Accomplished With Intravascular Ultrasound Guidance*," Circulation 91:1676–88, (1995)) and Goldberg et al. ("*Benefit Of Intracoronary Ultrasound In The Deployment Of Palmaz-Schatz Stents*", J. Am. Coll. Card. 24: 996–1003, (1994)) demonstrated that a factor resulting in subacute stent thrombosis in coronary arteries was inadequate expansion of the stent. This was done using intravascular ultrasonography (IVUS). Another factor, and related, is that the stents should be placed in close apposition to the vessel wall, so that the only flow obstructions are at the luminal surface of the stent struts. They later demonstrated that by using non-compliant balloons at high pressure (18 atm), that even the final assessment using IVUS is not required; an important consideration for centers lacking such equipment. Thus, it is preferable to minimize flow disturbances which may be created by stent implantation. This is more preferable in the smaller coronary arteries, which range from about 2.5–4 mm in diameter, than it is in other, larger arteries, where small amount of mural thrombus will have less effect on the volumetric flowrate.

Another factor is that the stent platform is not a solid piece of impermeable material, such as a rolled sheet, or a "jelly-roll", as described by Winston et al. (U.S. Pat. No. 5,411,551 issued May 2, 1995). In in vivo studies, Virmani, et al. ("*Histopathologic Evaluation Of An Expanded Polytetrafluoroethylene Nitinol Stent Endoprosthesis In Canine Iliofemoral Arteries*," JVIR, 10:445–456 (1999)) demonstrated that when endovascular stent-grafts are covered with porous graft material, it is possible for the graft material, in this case ePTFE, to become covered with a nearly intact layer of endothelial cells. However, when the same graft material was rendered impermeable to the underlying host vessel by wrapping it in FEP, the graft material was instead covered with a thick layer of thrombus. This demonstrates the desirability of using porous stents as anchors for the sensor.

Usually, a layer of fibrin clot deposits on the luminal surface of the implanted stent. After 3–4 weeks, the fibrin layer is typically remodeled into fibro-collagenous tissue, with a layer of endothelial cells present on the flow surface. However, if a relatively thick layer of fibro-collagenous tissue forms on the surface of an endovascular sensor, it may experience the same loss of signal that has been reported for subcutaneously implanted sensors. That is, a modified type of "foreign-body response" may occur, and glucose may not be able to freely and rapidly diffuse to the sensor. Evaluation of an ePTFE (expanded polytetrafluoroethylene) covered stent graft (Virmani, et al., 1999) showed that in areas where the graft surface was further from the center of the flow channel, it became covered with a relatively thick layer of thrombus, which eventually converted to fibro-collagenous tissue. In areas where the graft surface was closer to the center of the flow channel, it became covered with a relatively thin layer of tissue, and in some cases remained uncovered for periods of up to one year in a canine. Thus, there is a balance between minimizing disruption of blood flow, and excessive thrombus deposition.

Unlike a stent or stent-graft, which is used in the treatment of occlusive or aneurysmal vascular disease, however, the stent-sensor combination of the present invention should be placed in a relatively healthy portion of the artery. If it is placed in a stenotic or calcified area, it may be difficult for the device to expand completely, so the device may be more narrowed than is intended, resulting in thrombotic fouling of the sensor, or distal embolization may occur. If the device is placed in an aneurysmal vessel, it may expand more than intended, and again, fail to function as designed.

In addition, some types of sensors require that the actual sensing component be covered with a semi-permeable membrane in order to allow certain components such as glucose to pass through, while excluding cells, enzymes, or other factors which could damage the sensor. Thus, a stent-graft-sensor combination might be more suitable than a stent-sensor combination without the graft material. Further considerations will become apparent from the illustrated embodiments of the present invention which are discussed below.

FIG. 1A shows a perspective view of an expanded implantable sensor device 10 having a proximal end 12, a distal end 5 and a central lumen 16 extending therethrough. The expanded implantable sensor device 10 is comprised of a stent 14 and a sensor 20. Although the stent 14 illustrated in FIG. 1A resembles a Palmaz-Schatz stent, it is understood that any of a wide variety of stent configurations can be utilized such as those identified below. Whether the stent is a balloon expandable or self-expandable variety, the stent 14 comprises a tubul sidewall 18, which may be compressed to a relatively small diameter for delivery using a catheter, and which may be expandable to the approximate diameter of the vessel or to a diameter approximately 5–25% greater than the diameter of the vessel lumen.

In general, a self-expanding variety of stent or stent-graft such as the S.M.A.R.T. Stent (Cordis Corp., Miami, Fla.) or Hemobahn (W.L. Gore & Associates, Flagstaff, Ariz.) is preferred, because the presence of the sensor body may impede proper expansion of the stent platform using a balloon. The sensor housing can preferably be attached to the stent by use of adhesives, by tying (suturing) the two components together, or by use of thermal bonding, soldering, welding or brazing, or mechanical interfit or the like. The sensor and sensor housing should be attached to the stent along a single row of stent struts, so that the struts may fully expand without needing to stretch the sensor housing, or being constrained by the sensor housing.

An example of the type of stent which could be used in certain embodiments of the present invention is described by Lau et al. in U.S. Pat. No. 5,876,432, issued Mar. 2, 1999 which is herein incorporated by reference. Other stents which are suitable for use in the present invention are described by U.S. Pat. No. 4,739,762 to Palmaz, issued Apr. 26, 1988; U.S. Pat. No. 5,102,417 to Palmaz, issued Apr. 7, 1992; U.S. Pat. No. 5,421,955 to Lau et al., issued Jun. 6, 1995; U.S. Pat. No. 5,195,984 to Schatz, issued on Mar. 23, 1993; U.S. Pat. No. 4,886,062 to Wiktor, issued Dec. 12, 1989; U.S. Pat. No. 4,655,771 to Wallsten, issued Apr. 7, 1987; U.S. Pat. No. 5443,500 to Sigwart, issued Aug. 22, 1995; and U.S. Pat. No. 4,580,568 to Gianturco, issued Apr. 8, 1986; which are all incorporated in their entireties herein by reference. The expanded inside diameter of the device may range from 3 to 20 mm, and the length of the device may range from 1 to 30 cm. The radially inwardly facing or radially outwardly facing sidewall of the stent may also be covered by a sheath as is known in the art. The sheath can be bonded to the surface of the stent so that the sheath remains in close apposition to the vessel wall.

Attached to the stent 14, a sensor 20 contains the sensing circuitry within its housing. Depending upon the stent 14 design and sensor 20 design, the attachment between the sensor 20 and the stent can take any of a variety of forms as will be apparent to those of skill in the art in view of the disclosure herein. For example, adjacent axially extending parallel struts of the stent design illustrated in FIG. 1A spread circumferentially apart upon expansion. Thus, the sensor 20 should be mounted to only colinear axial struts along the length of the stent unless the mounting is designed to accommodate circumferential separation of parallel struts. Alternatively, the sensor 20 may be positioned in an aperture which is cut in the sidewall of the stent 14, and attached to the strut portions adjacent to the edge of the aperture. Attachment may be accomplished in any of a variety of ways, such as by the use of adhesives, thermal bonding, soldering, welding or brazing, or mechanical interfit, depending upon the construction materials of the stent 14 and the sensor 20. Alternatively, the sensor 20 may be solvent bonded, adhesively bonded or otherwise attached to an expandable tubular sleeve which is positioned concentrically about the stent 14. Other attachment configurations can be devised by those of skill in the art in view of the disclosure herein.

In the illustrated embodiment, all or a portion of the sensor 20 is positioned on the radially outwardly facing surface of the tubular sidewall 18. Positioning the sensor 20 on the radially outwardly facing surface (sometimes referred to herein as the abluminal surface) may advantageously optimize blood flow through the central lumen 16 and/or reduce turbulence in the central lumen 16. Alternatively, the sensor 20 may be positioned on the radially inwardly facing surface (sometimes referred to herein as the luminal surface) of the stent. In addition, the stent struts or other elements which make up the sidewall 18 may be removed or modified at the portion of the sidewall corresponding to the sensor 20 such that the sensor 20 may be mounted within the resulting opening in the sidewall. Because the implantable sensor device 10, in accordance with the present invention, is preferably positioned within a healthy section of the vessel, the radial strength normally required for a stent in a post-angioplasty application is unnecessary. Thus, the present inventor believes that any reduction in radial support which may result from reasonably dimensioned apertures or other modifications to the sidewall to attach sensor 20 will not adversely affect the role of the stent as a sensor support structure in the context of the present invention. Additional details concerning the position of the sensor 20 with respect to the tubular wall 18 will be discussed below in connection with FIGS. 5A–5C.

The sensor circuitry 22 includes a sensing circuit 24, which is connected to a signal processing circuit 26, which is connected to a power source 28, a radio transmitter 30, and an antenna (not shown) to transmit signals about the glucose concentration to a remote device. The antenna (not shown) may be a thin wire wound around the stent 10, or preferably, may be wound around a small ferrite core, as commonly used for such applications. This provides certain advantages, such as increased signal strength or increased transmission distance for the same amount of power required. In Keilman et al. (U.S. Pat. No. 6,231,516, issued May 15, 2001), for example, the implied requirement to minimize protrusion of the sensor and transmitter into the vessel lumen requires that the stent be constructed using unwieldy manufacturing processes, and the signal strength is weakened by the inability to use a ferrite core.

The power source 28 may be inductively coupled to an external device, or it may be a thin film rechargeable battery, as in Bates, J. B. et al., "*Thin Film Rechargeable Lithium Batteries for Implantable Devices*", ASAIO J., 1997

43:M644–M647, which is incorporated herein by reference. Alternatively, the power source may be a battery, such as lithium iodide, lithium silver vanadium oxide, lithium carbon monofluoride, or lithium ion rechargeable battery, as commercially available from Wilson Greatbatch Technologies, Inc. (Clarence, N.Y.).

Figure 1D:
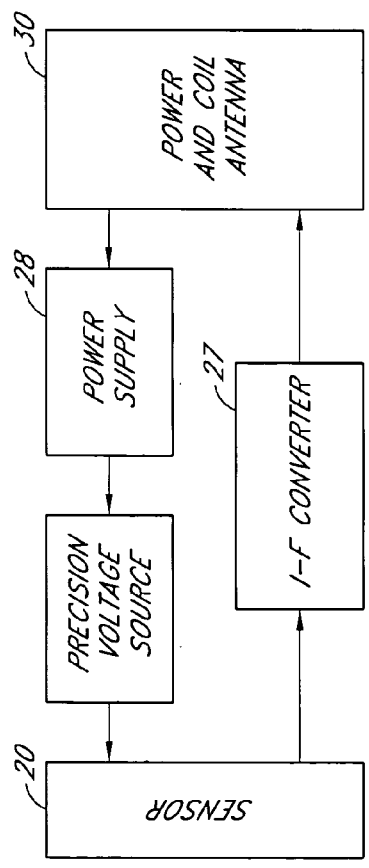
FIG. 1D is a block diagram of the sensor circuitry for measuring analyte concentration.

The glucose sensor monitoring circuit and the remote measurement unit circuit are shown in FIGS. 1D and 1E. The glucose sensor monitoring circuit consists of a voltage source (25) to drive the sensor (20), and a current-to-frequency converter (27). The circuit is powered by an external field produced by the remote measurement device. In normal operation, the remote measurement device (FIG. 1E) is placed over the area where the sensor is implanted. This produces a voltage across the Power Coil and Antenna (30) that is then regulated by the power supply (28) to provide a source of power for the sensor electronics (voltage source and current-to-frequency converter). Once powered, the circuit will produce an output frequency that is directly proportional to the concentration of glucose.

FIG. 1E shows a block diagram of the electronics for the remote measuring unit. The remote monitoring unit provides the drive to power the sensor electronics and also receives and processes the signal from the V-F converter. A high current drive circuit (37), running at a frequency much lower than the V-F converter, is used to excite the antenna/excitation coil (34). Because the signal received from the sensor is much higher than the excitation signal, the former is filtered and amplified in amplifer/filter (35). The microcontroller (39) measures the frequency and then uses a calibrated look-up table to provide translation to the proper units and also to compensate for any non-linearities in the device response curves. The final result is displayed on an LCD (not shown) for the user.

The sensing circuit 24 is in electrical communication with a sensing surface (not illustrated in FIG. 1A) for sensing the analyte of interest in the fluid stream. In the embodiment illustrated in FIG. 1A, the sensor surface is preferably positioned radially inwardly from the radially inwardly facing surface of the tubular sidewall 18, to improve the useful life of the device as is discussed elsewhere herein. Thus, in an embodiment such as that illustrated in FIG. 1A in which the sensor 20 is positioned on the abluminal side of the tubular sidewall 18, the sensor surface is displaced radially inwardly such as by a radially inwardly extending portion of the housing or other support (not illustrated) to achieve the desired radial position of the sensor surface. Alternatively, in an embodiment in which the sensor 20 is positioned on the luminal side of the tubular side wall 18, or within or through an opening in the tubular sidewall 18, the sensor surface may be positioned directly on a radially inwardly-most extending portion of the sensor 20 as is discussed elsewhere herein.

The sensor surface is preferably covered by a semi-permeable membrane (not shown), which contacts passing blood when the stent 14 is placed in a blood vessel. The permeability of the membrane is selected to allow blood glucose, or the analyte of interest to freely contact the sensor, while restricting the passage of other blood components. The semi-permeable membrane may comprise ePTFE, Dacron®, polyurethane, silicone rubber, poly(lactide-co-glycolide) (PLGA), poly(caprolactone) (PCL), poly(ethylene glycol) (PEG), collagen, polypropylene, cellulose acetate, poly(vinylidene fluoride) (PVDF), nafion or other biocompatible material. These membrane materials may also be used for the tubular sheath which can be used to surround either the luminal or abluminal surfaces of the stent. The membrane of the sheath may be bonded to the stent by adhesives or by tying (suturing) the two components together or by use of thermal bonding, soldering, welding or brazing, or mechanical interfit. The pore size of the lumenal membrane may be large enough to allow cells to come through if it covers the sensor surface, but the sensor membrane should have a pore size (MW cutoff of about 1000) which will allow glucose to pass, while restricting the passage of larger molecules. The entire tube surface does not have to be composed of the same membrane material. The part of the device near the sensing element can be composed of a different material or have a different porosity than the material in the rest of the device.

Referring to FIG. 1B, a remote circuit 32 is equipped with an antenna 34 and a signal processing unit 36, which converts the electronic signal from the embedded sensor into a concentration level or other indicium of the analyte. Preferably, an alarm circuit 38 and a display 40 are also provided. Information regarding the level of the analyte of interest can be displayed on the display 40 such as a monitor 42. The signal processing unit 36 may be provided with a lookup table or other baseline of normal or expected values for the analyte of interest. If the concentration of the analyte goes outside of the prescribed range, or if an electronic failure is detected, a warning audible, visible, or tactile signal is preferably produced from the alarm system 38. A transmitter 44 may also be included in the remote circuitry 32 in order to transmit data about the level of the analyte of interest to an implantable infusion pump, or the like.

The remote circuitry 32 can be provided in any of a variety of physical forms, depending upon the intended use of the device. For example, in a hospital or other immobilized patient setting, the remote circuitry 32 can be provided in a desktop or bedside housing and coupled directly to a display 40 such as a monitor 42. Alternatively, ambulatory patient devices may be provided by deleting a permanent coupling to the monitor 42 and packaging the remaining components of remote circuit 32 in a wearable form, such as a compact self-contained unit adapted for attachment to the wearer's clothing or including straps so that it can be strapped to the patient's body. In an ambulatory device, the signal processing unit 36 includes sufficient memory to record the glucose values over a predetermined period of time. The patient can couple the wearable device to an external monitor 42 or other electronics periodically, such as one or more times per day. Analyte data may thereafter be displayed in readable form, such as on a monitor 42 in table form or in graph form with a time unit on the X axis and a glucose value or derivative data on the Y axis.

The wearable unit (not illustrated) may additionally be provided with a data export coupling, such as a telephone connector, for connecting the signal processing unit 36 via internal or external modem into the telephone system. In this manner, the patient can transmit condensed analyte data to the healthcare provider for further monitoring and/or analysis. The wearable unit may additionally be provided with one or more manual data inputting elements ranging from a simple push button to a keypad, to allow manual data entry relating to significant dietary or other events. For example, meal times, significant fluid intake, manual insulin injection or other administration, or any of a variety of other significant events can be marked in the data, so that the patient or reviewing medical personnel can correlate the event with the blood glucose data.

Referring to FIG. 1C, there is schematically illustrated an implantable or externally wearable infusion pump 46. The infusion pump 46 may be controlled by the remote circuit 32 via a receiver 48 in the pump, or may be manually controlled using sensor information only as a guideline. The infusion pump 46 may be refilled through an appropriately designed port 50 such as a pierceable septum using a hypodermic needle or other appropriate delivery system. The infusion pump 46 may be implantable, as described by Irsigler et al., ("*Controlled Drug Delivery in the Treatment of Diabetes Mellitus*", Crit. Rev. Ther. Drug Carrier Syst. 1(3): 189–280 (1985)), which is incorporated herein by reference. Alternatively, it may be worn externally by the patient, and infuse insulin or other drugs as appropriate through a catheter 15 which is inserted into the patient's body. External insulin infusion pumps are currently marketed by suppliers like Medtronic, or Siemens. However, these pumps are not designed to receive a continuous signal from an implanted sensor, but instead are pre-programmed to approximate the patient's baseline insulin requirements. Such pumps can be modified with an with appropriate circuitry to receive and respond to output from the glucose sensor by those of skill in the art in view of the disclosure herein.

Figure 2:
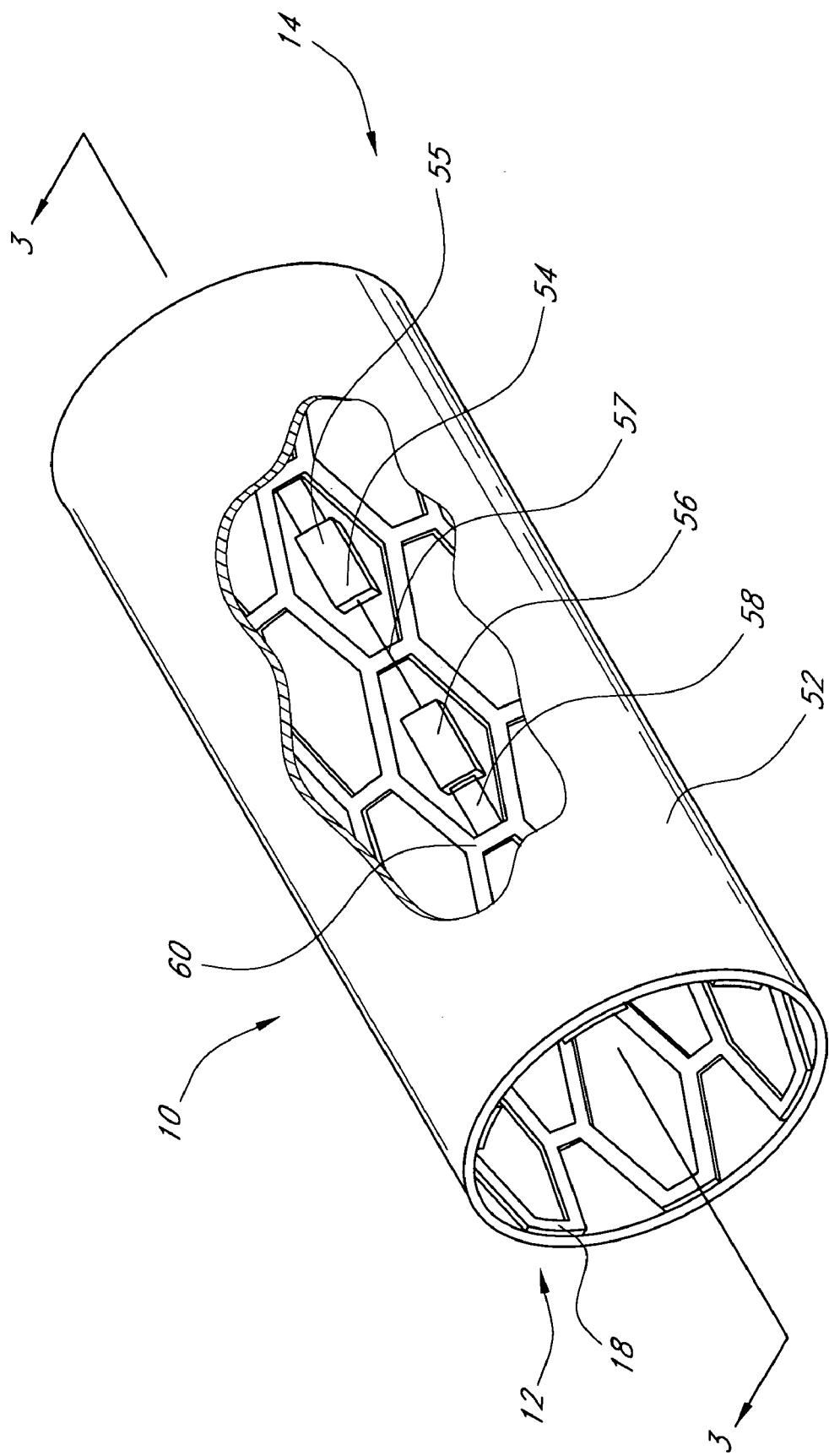
FIG. 2 is a perspective partial cut away view of a stent sensor device surrounded by a sheath.
Figure 3:
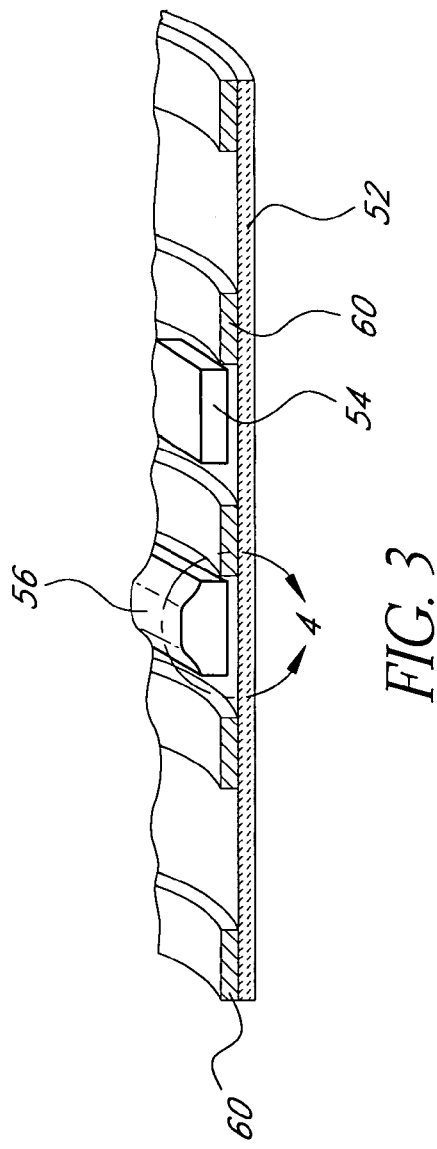
FIG. 3 is a cross-section taken along the line 3—3 in FIG. 2.

Now referring to FIG. 2, a covered implantable sensor device 10 is shown. The sensor 10 comprises a cylindrical stent wall 18 surrounded by a sheath 52. An antenna (not shown) may be wound around the body of the sensor 10 and connected to the power source or the transmitter. All relevant electronics are schematically illustrated as in electronics housing 54 which is electrically coupled to a sensor 56 by one or more conductors 57. All such junctions of dissimilar metals are coated with polymers which are impermeable to bodily fluids in order to reduce galvanic corrosion. The analyte sensing element 56 is covered with a membrane 62 (FIG. 4) which is permeable to the analyte of interest. The analyte sensing element 56 extends radially inwardly within the sensor 10 where blood flow conditions are optimal.

Figure 4:
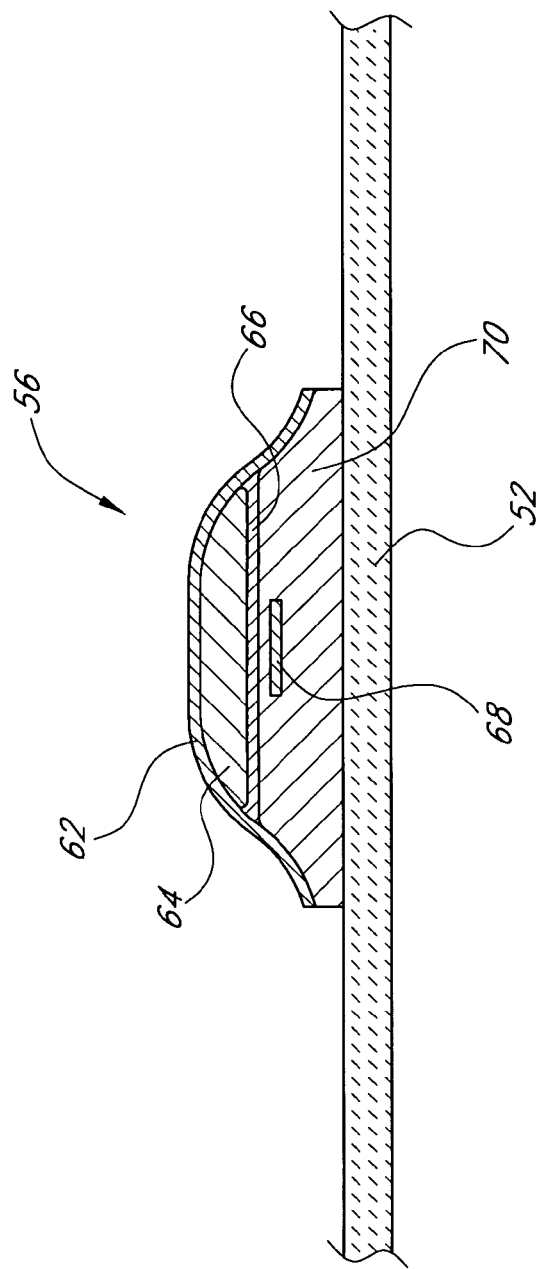
FIG. 4 is an enlarged cross-sectional view through the sensor element of FIG. 3.

Now referring to FIGS. 2, 4 and 5, the illustrated analyte sensing element 56 contains an enzyme gel layer 64, which is placed adjacent to the outer permeable membrane 62. The analyte diffuses through the membrane 62 to the gel enzyme layer 64. The reaction between the analyte and the enzyme occur in the gel enzyme layer 64. The reaction products then pass through an inner membrane 66 and react at the surface of a noble metal electrode 68, producing a current. An appropriate potential is applied to the electrode 68 from the power source contained in electronics housing 54 resulting in a signal, which is sent to the signal processing unit. The signal is then passed through the transmitter which transmits the information regarding the analyte of interest to an external monitor and/or implantable pump as has been discussed. The power source, the signal processing unit, and the transmitter are completely encapsulated in a housing 55 which is impermeable to biological fluids. The same housing 55 or a separate housing 70 also encapsulate the analyte sensor except for the membrane 62.

The sensor(s) to be incorporated into the device may be either electrochemical, piezoelectric, thermoelectric, acoustic, or optical. As known to those skilled in the art, there is a significant body of literature regarding the development of electrochemical glucose sensors. These generally incorporate an enzyme, which selectively reacts with glucose.

Electrochemical biosensors may be categorized as amperometric, conductometric, or potentiometric. Amperometric measurements are based on the oxidation or reduction or electrochemically active substances involved in the oxidation of glucose via glucose oxidase. Another method is measurement of changes in local pH due to the gluconic acid produced using a potentiometric sensor, usually a coated-wire pH selective electrode and/or ion-selective field effect transistor (ISFET). Conductometric sensors are based on the principle of electrical resistance changes during the reaction.

Potentiometric and conductometric sensors are currently limited due to the presence of numerous interfering chemicals in the environment. The main disadvantage of these sensors is their low sensitivity. The response of the potentiometric sensor depends on logarithmic changes in analyte concentration.

Microelectronics using ion selective field effect transistors (ISFET's) have been used for measurements of different analytes in body fluids (Erickson, K. A., et al., "Evaluation of a Novel Point-of-care System, the I-Stat Portable Clinical Analyzer", Clin. Chem. 39(2):283–287 (1993) which is herein incorporated). This allows miniaturization and integration of the transducer with associated electronic circuitry into a single chip. However, corrosion of the semiconductor material surface in saline and in physiological fluids is presently a problem for in vivo use. This problem may be corrected by surface coating or passivation of the ISFET. These types of sensors also belong to the class of potentiometric sensors, as described above.

Amperometric sensors respond linearly to the analyte concentration. If the limiting processes in signal generation are the enzymatic reactions, the dependence of the signal on glucose concentration is non-linear according to Michaelis-Menton kinetics. When the sensor operates in a glucose diffusion-limited mode, the signal is linearly proportional to the analyte concentration. Amperometric sensors are further subdivided into three classes:

1) Based on the production of hydrogen peroxide or consumption of oxygen.
2) Low molecular weight compounds used as mediators of the electron transfer process.
3) Direct electron transfer between the enzyme and the electrode.

Oxygen-electrode based sensors:

An operational enzyme electrode was first reported by Updike and Hicks (Updike, J. W., and Hicks, J. P., "*The Enzyme Electrode*," Nature, 214: 986–8, (1967)) based on a description by Clark and Lyons (Clark L. C., and Lyons, C., "*Electrode Systems for Continuous Monitoring in Cardiovascular*," Ann. NY Acad. Sci., 102:29–45 (1962)). In this process, the oxygen consumed in the oxidation of glucose is measured. The Clark oxygen electrode employs a platinum cathode held at a potential of approximately (−)0.6 V versus the saturated calomel electrode (S.C.E.), a sufficiently negative potential to reduce oxygen as follows:

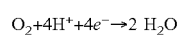

Because the species being measured in this reaction is a gas, interference from other species in the biological fluid is negligible. However, the signal is determined from reduction of the initial current, making glucose determinations at low concentrations difficult. Further, the system requires the use of a second electrode without any glucose oxidase, to determine the local oxygen tension for the glucose measurement. In addition, it is necessary to insure that there is excess oxygen in the catalytic layer so that the reaction rate is limited by the glucose. The ratio of blood glucose to oxygen can be as high as 10 to 1 in arterial blood, and 100 to 1 in venous blood. (Jaffari 1995) An oxygen electrode sensor has been described by Armour et al. (1990), which was implanted in the superior vena cava of six dogs for up to 15 weeks, with good agreement with standard in vitro assays.

Hydrogen Peroxide based sensors measure hydrogen peroxide production based on the oxidation of glucose at potentials above +600 mV vs. SCE. This signal is directly related to the concentration of glucose in the sample.

$$H_2O_2 \rightarrow O_2 + 2H^+ + 2e^-$$

Unfortunately, the high operating potential required can also result in the oxidation of other chemical species in the blood. This may be overcome by the. use of membranes. Bindra et al. (Bindra, D. S. et al., "*Design and in vitro studies of a needle type glucose sensor for subcutaneous monitoring*," Anal. Chem., 63: 1692–6 (1991)) reported glucose detection for up to 10 days in rats with a needle-type sensor, which consisted of GOD immobilized onto cellulose acetate as an inner membrane, and polyurethane as an outer membrane. Moussy et al. (Moussy, F. et al., "*Performance of subcutaneously implanted needle-type glucose sensors employing a novel trilayer coating*," Anal. Chem., 65: 2072–7 (1993)) used a needle type sensor with a trilayer coating. Nafion was used as an outer membrane, and poly (o-phenylenediamine) as an inner membrane to reduce interference from small electroactive species. GOD was immobilized between these two layers. As with the oxygen electrodes, the reaction must be limited by glucose, not oxygen.

In amperometric sensors with mediated electron transfer, oxygen as an electron acceptor is substituted by an artificial mediator, to overcome the tissue oxygen dependence of amperometric biosensors. Ferrocene and its derivatives are the most commonly used, although hexacyanoferrate (III), tetrathiafuvalene, and ruthenium hexamine (Jaffari, 1995) have also been investigated. In these sensors, a process involving the mediator instead of oxygen takes place:

$$GOD(red) + Mediator(ox) \rightarrow GOD(ox) + mediator(red)$$

At the electrode:

$$Mediator(red) \rightarrow Mediator(ox)$$

The electrochemical oxidation of the reduced mediator occurs at a low potential, thus reducing the sensitivity of the sensor to interfering compounds.

Limitations to the in vivo use of the sensor involve leaching of the mediator, and the possible toxicity of the mediator. This has been addressed by approaches such as:

1) Binding of the mediator to high molecular weight compounds,
2) Entrapment of the mediator and enzyme in conducting polymer films,
3) Covalent attachment of the mediator to a polymer film,
4) Modification of the enzyme with mediator molecules, and
5) Use of polymeric mediators.

All of these approaches have been investigated to reduce mediator leaching, although none have been tested in vivo (Jaffari, 1995).

An advantage of this type of sensor, because oxygen is not involved in the signal generation process, is that the sensor signal becomes independent of the oxygen concentration (Wilkins, 1996).

Amperometric sensors with direct electron transfer are independent of the oxygen concentration and involve direct oxidation of glucose by GOD at an electrode constructed from conducting organic salts (charge-transfer organic complexes with electron conductivity). Sensors based on this principle have been tested in vivo in rats, but little is presently known about the biocompatibility of such materials.

Examples of sensors that would be suitable for use in this invention include electrochemical sensors described in U.S. Pat. No. 6,001,067, issued to Shults, et al., "Device and method for determining analyte levels", Dec. 14, 1999, and U.S. Pat. No. 6,212,416, issued to Ward et al, Apr. 3, 2001, "Device for monitoring changes in analyte concentration".

Other types of sensors suitable for practicing the present invention, and which also depend on continuous blood glucose transport to the sensor, are fluorescence based sensors described in patents issued to Colvin, including U.S. Pat. No. 5,517,313, (issued May 14, 1996), and further described in U.S. Pat. No. 5,894,351 issued Apr. 13, 1999, U.S. Pat. No. 5,910,661 issued Jun. 8, 1999, U.S. Pat. No. 5,917,605 issued Jun. 29, 1999, U.S. Pat. No. 6,304,766 issued Oct. 16, 2001, and the following patents issued to Colvin et al., including U.S. Pat. No. 6,330,464 issued Dec. 11, 2001, U.S. Pat. No. 6,344,360, issued Feb. 5, 2002.

Another type of sensor for which the present invention is well suited, are pressure-based sensors, in which glucose sensitive hydrogels exert pressures which are related to glucose concentrations, described by Han et al in U.S. Pat. No. 6,514,689, "Hydrogel Biosensor", issued Feb. 4, 2003.

The most commonly used membrane for implantable biosensors is polyurethane (Jaffari, 1995). Other membranes which have been investigated include cellulose acetate, polypropylene, silicone rubber, and Nafion. These membranes have shown promise in short term monitoring, but long-term monitoring has been more difficult. Davies et al. (Davies, M. L., et al., "*Polymer membranes in clinical sensor application. Part* 1: *an overview of membrane function*," Biomaterials, 13: 971–89, (1992)) have reviewed extensively the range of polymers used as membranes for biosensors. Updike reported that immobilization of glucose oxidase within a membrane allowed it to accurately measure glucose levels for well over one year.

In a preferred embodiment, an amperometric electrode is used. The characteristics of such an electrode, such as one available from Minimed, Inc. (Sylmar, Calif.), is related to the production of hydrogen peroxide in the conversion of glucose to gluconic acid by glucose oxidase. The noble metal electrode 68 may be connected to any of a variety of RF transceivers. To avoid the use of batteries, which may be too large for this application, the system may be powered by, and signal transmission occurs via an inductive link. This requires an inductive coil (not shown) to be placed both inside the external receiver and an inductive coil (not shown) within the implantable sensor device 10. An example of the type of transceiver to be used is employed in the Ventak Mini IV automatic implantable cardioverter defibrillator (Guidant Corp, Santa Clara, Calif.). The transceiver coil in the preferred embodiment is specifically adapted for use with a stent platform. The size of the coil, in addition to the number of turns around the implant limits the power and signal transmission distance between the implant and the external receiver/power supply. In order to maximize the diameter of the coil, the coil is wound around the outside of the implantable sensor device 10. The transceiver coil is made from an electrically conductive material, and is coated to prevent corrosion. The coil may be aligned with and bonded to the struts of the implantable sensor device 10, in order to minimize any impact on expansion of the implantable sensor device 10. Alternatively, the struts of the implantable sensor device 10 themselves may serve as the antenna coil. In addition, in order to maximize signal transmission, the internal and external coils should be aligned so that their major axes are parallel. The external receiver coil should contain a ferrite core to optimize power and signal transmission. The external receiver and power supply should be designed so that it can be worn on the patient's body, and can be oriented to maximize the signal from the implanted sensor. This can be done by custom-placed foam padding to orient the external receiver and power supply.

Figure 6A:
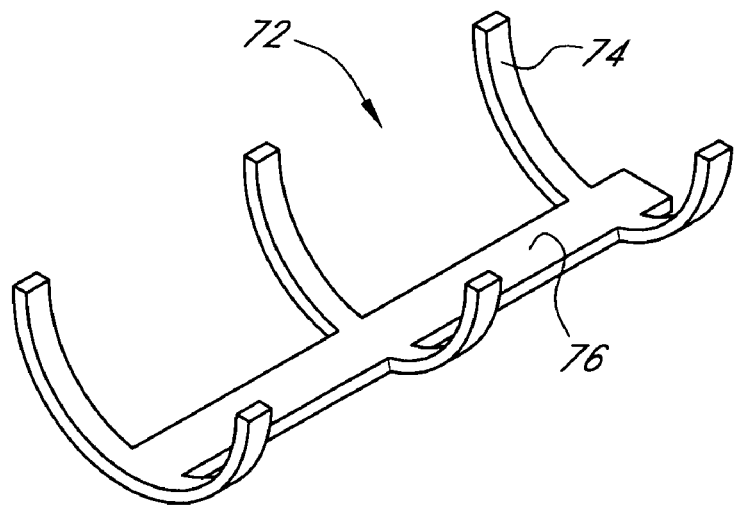
FIG. 6A is a perspective view of an alternate support structure in accordance with the present invention.
Figure 6B:
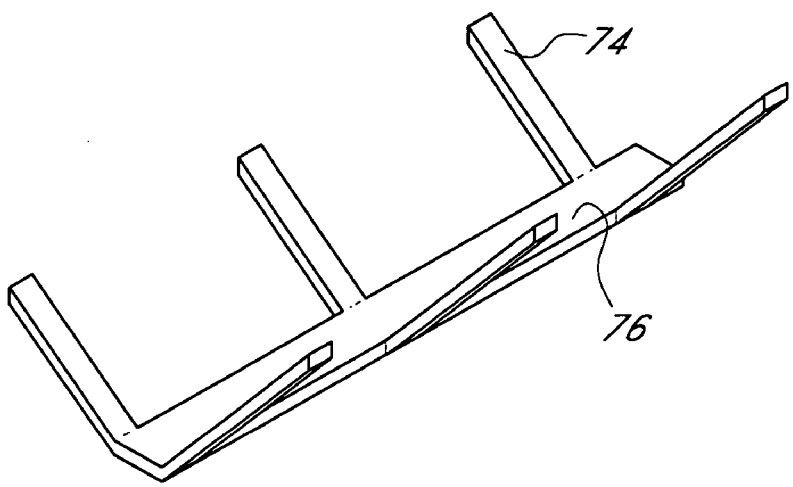
FIG. 6B is a perspective view of a further support structure in accordance with the present invention.
Figure 6C:
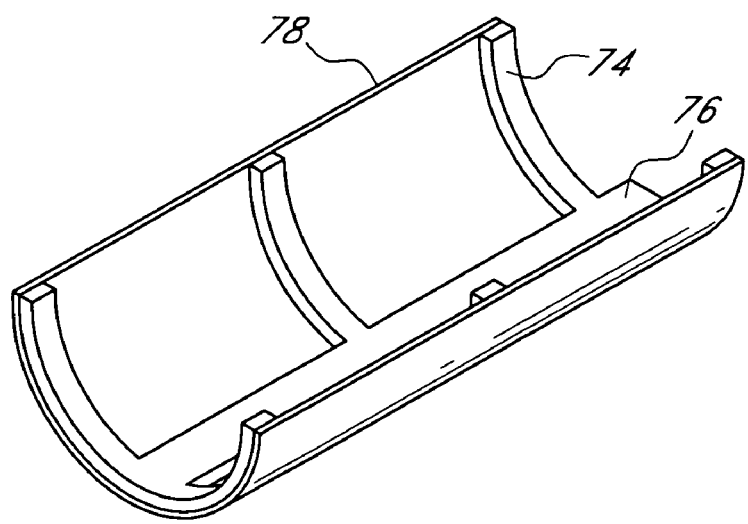
FIG. 6C is a perspective view of the support structure illustrated in FIG. 6A, provided with an outer fabric sheath.

Now referring to FIGS. 6A–6C, alternatively, the sensor device may be held in place within the vessel by any of a variety of anchoring systems other than a graft or stent. For example, any of a variety of anchoring structures may be provided with hooks or barbs to engage the vessel wall. Alternatively, semicircular cages or struts may be used, which only extend through a partial circumference of the vessel. FIG. 6A shows struts 74 that can be positioned securely against a blood vessel. An axially extending strut 76 connects the circumferential struts 74, and also could support a sensor. The support 72 can be manufactured in a variety of ways, such as by injection molding a suitable polymeric material or by laser cutting from stainless steel, Nitinol or other tube stock. FIG. 6B shows alternate struts 74 that can be secured against the vessel wall. Again, connecting struts 74 is one or more connecting struts 76. FIG. 6C shows a modification of the device shown in FIG. 6A, where the support 72 is provided with a sheath 180. In the case of Ward et al. (U.S. Pat. No. 6,212,416), they suggest the possible use of the sensor in an artery or vein, but provide no mechanism to secure the sensor within the vessel. If used as described, without such anchoring mechanism, the device would migrate within the vessel, causing significant injury to the patient, such as stroke, myocardial infarction, or pulmonary embolism, all of which are life threatening.

In order to implant an implantable sensor device within the vasculature of the patient, a catheter-based delivery system is used. All implantable sensor devices are formed to include a central lumen with a diameter in the reduced profile sufficient to allow passage of a guide wire and a catheter tip through it. The implantable sensor device is mounted onto a catheter tip, and then collapsed to as small a diameter as possible. The implantable sensor device may be deployed by removal of a deployment sheath, or other methods, which may be preferred for the specific type of stent platform being employed. These methods are well known in the art. After the implantable sensor device is deployed, the catheter and guidewire are removed from the (now enlarged) central lumen in the implantable sensor device. The implantable sensor device is placed such that neither the catheter nor the guidewire adversely affects the electronic circuitry.

Preferably, the implantable sensor device is implanted in a relatively large artery or vein (>5 mm) in order to minimize the risk that the implant may occlude the artery. In addition, a healthy artery or vein should be chosen, so that the device can open completely, and so that the flow patterns are normal.

Clinically, it is now accepted practice to place the stent in a parent vessel so that the stent struts cross the ostium of a side branch vessel. This is called "stent jail." (Pan, M., et al., "*Simple and Complex Stent Strategies for Bifurcated Coronary Arterial Stenosis Involving the Side Branch Origin*," Am. J. Cardiol., 83: 1320–25 (1999)). In addition, for stent-grafts for aortic aneurysm repair, investigation is being carried out regarding stent struts which cross the renal artery ostia. An example of such a suprarenal device is the Talent Aortic Stent-Graft (Medtronic, Inc.). This suggests that it is possible to have a wire (or transducer) which is placed directly across an artery without thrombus formation or thrombo-embolization. Thus, in an alternative embodiment, the sensor or sensing element (i.e., the transducer) can be placed directly across the path of the flowing blood, on a surface with low cross-sectional area, such as a wire with a diameter of 0.003" to 0.025", or a ribbon, oriented with its narrow edge facing upstream. The transducer or sensor can be placed on either the proximal, distal, or lateral faces of the wire or ribbon.

As with sensors mounted on or near the wall of the vessel, it is important that the sensor be placed across a large vessel with high blood velocity. This will not result in significant thrombus deposition, and any emboli which may result will be of sufficiently small size that they will be readily lysed by the patient.

As with stents, there are a multitude of possible designs for a sensing element which is placed directly across the bloodstream, as will be appreciated by those skilled in the art. The transducer (or sensing element) could be placed along the surface of a single, straight wire. FIG. 9A shows a cross-sectional view through a stent 14, which includes a sensing element 120 consisting of a wire-like noble electrode 68, which in turn is covered by a gel-enzyme layer 64 and finally by an analyte-permeable membrane 62. The outside of the analyte-permeable membrane 62 is bound to a wire-like structure made of a shape memory material 110 such as nitinol, which is either part of or is bonded to the stent 14. The shape memory material allows the electrode 68 and sensing element 120 to be positioned directly across the lumen of the vessel, as described above. The electrode 68 is connected to the signal processing unit (not shown) through a conductor (not shown). The remainder of the implantable sensor 10, including the power source, signal processing unit, transmitter, and stent, are positioned to be flush against the vessel wall.

Figure 9B:
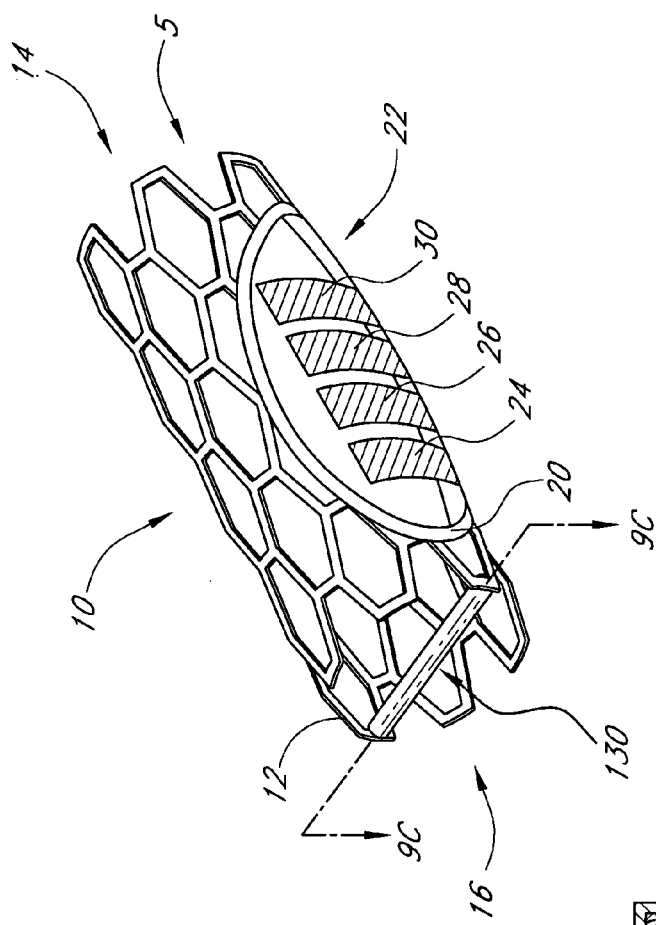
FIG. 9B is a perspective view of an expanded stent with an embedded sensor housing on its abluminal side and a transducer across the cross-section of the stent.
Figure 9C:
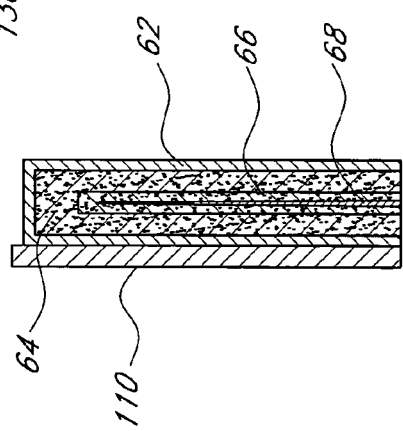
FIG. 9C is an enlarged cross-sectional view of the transducer of FIG. 9B, taken from the 9C—9C line.
Figure 9A:
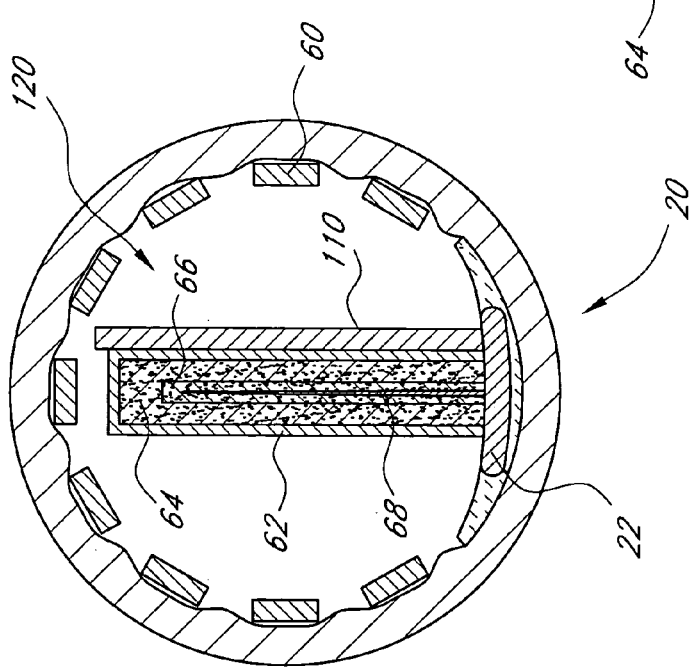
FIG. 9A is a cross-sectional view through a stent showing a transducer across the cross-section of the stent in accordance with the present invention.

FIG. 9B shows an implantable sensor device 10 with a sensing element 130 across the cross-section of the stent 14, with sensor circuitry 22. FIG. 9C shows an enlarged cross-sectional view of the sensing element 130 of FIG. 9B, taken along the 9C—9C line. The sensing element 130 consists of a wire-like noble electrode 68, which in turn is covered by a gel-enzyme layer 64 and finally by an analyte-permeable membrane 62. The outside of the analyte-permeable membrane 62 is bound to a wire-like structure made of a shape memory material 110 such as nitinol, which is bonded to the stent 14 on both ends. The sensing element 130 is connected to the sensing circuit 24 through a conductor (not shown).

FIG. 9D illustrates a transducer 140, consisting of a wire-like noble electrode 68, which in turn is covered by a gel-enzyme layer 64 and finally by an analyte-permeable membrane 62, which is bound to a wire-like structure made of a shape memory material 110 such as nitinol, which is bonded to the stent 14. The sensing element 140 is connected to the sensing circuit 24 through a conductor (not shown).

FIG. 9E shows another configuration with quadruple sensing elements 150, each at right angles to each other, attached to stent 14, with sensor circuitry 22. The sensing elements 150 are connected to the sensing circuit 24 through a conductor (not shown). Alternatively, multiple transducers could be positioned to form a wire mesh, provided the mesh size is sufficiently large to permit blood flow without significant thrombo-embolization. In other acceptable configurations, a very small sensor surface area impedes blood flow, compared to the blood vessel's cross-sectional area.

Figures 7A, 8:
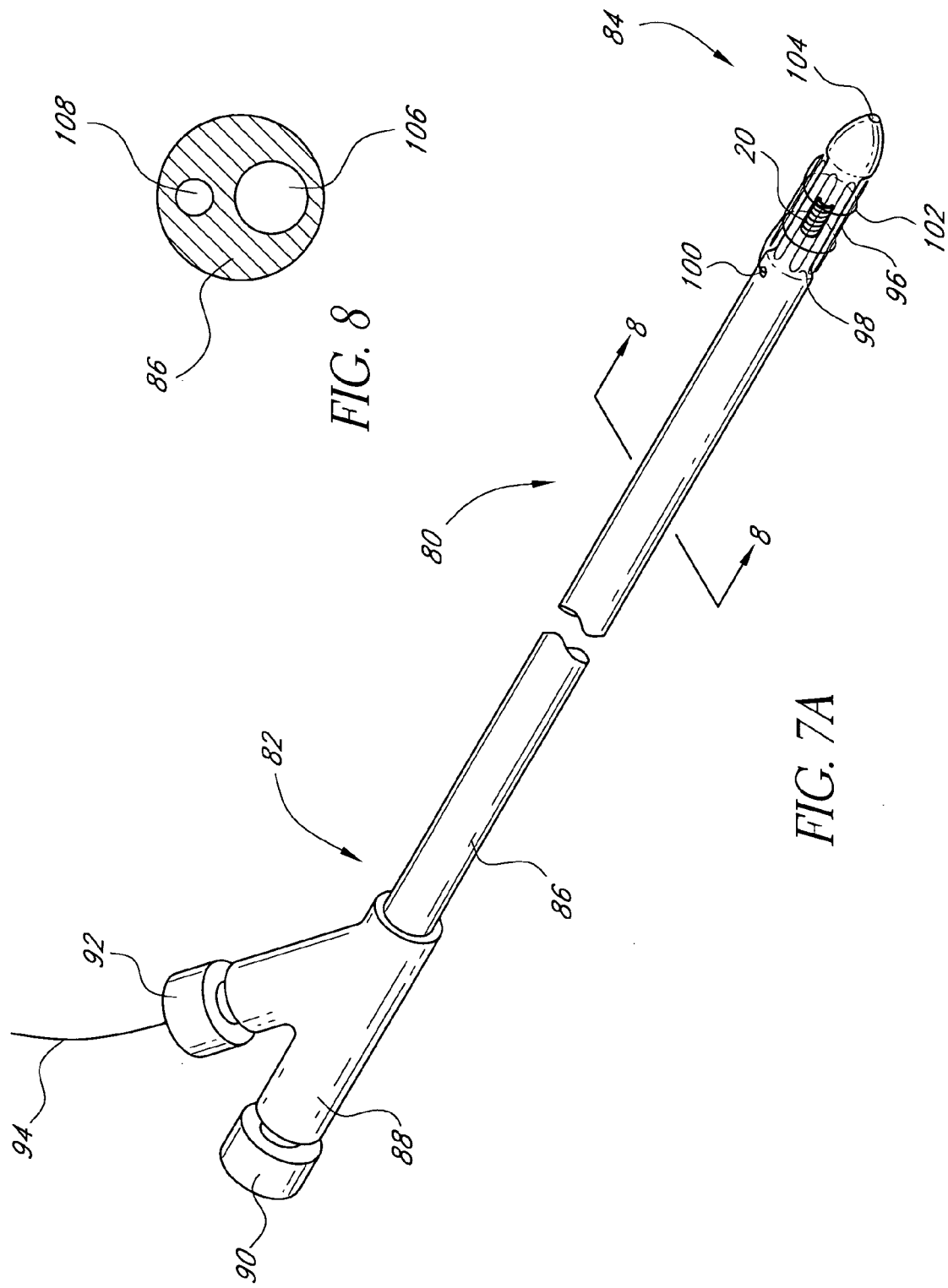
FIG. 7A is a side elevational view of the distal end of a catheter-based delivery system for a stent sensor device.
FIG. 8 is a cross-sectional view of the catheter-based delivery system taken along the 8—8 line of FIG. 7A.

Referring to FIG. 7A, there is disclosed a deployment catheter 80 which may be utilized to deploy a self-expandable stent type sensor support in accordance with the present invention. The catheter 80 comprises a proximal end 82, a distal end 84 and an elongate flexible tubular body 86 extending therebetween. The length of the tubular body 86 will vary depending upon the intended access point and deployment site for the stent sensor. For example, lengths in the area of about 120 cm to about 140 cm are typical for use in a coronary artery implantation by way of a femoral artery percutaneous puncture site. Other lengths for different access sites and deployment sites will be apparent to those of skill in the art in view of the disclosure herein.

The tubular body 86 may be manufactured in accordance with any of a variety of known techniques, such as by extrusion of appropriate biocompatible polymeric materials. Known materials which are commonly used for this application include high density polyethylene, polytetrofluroethylene, nylons, and a variety of others known in the art. Alternatively, at least a portion or all of the lengths of the tubular body 86 may comprise a spring coil, solid wall hypodermic needle tubing, or braided reinforced wall, depending upon the functional requirements of the catheter.

For most applications, the tubular body 86 will be provided with an approximately circular cross-sectional configuration having an external diameter within the range of from about 0.025 inches to about 0.065 inches. In accordance with one embodiment of the invention, the tubular body 86 comprises a multilumen extrusion having an external diameter of about 0.042 inches (3.2 f) throughout substantially all of its length. Alternatively, the tubular body 86 can have diameters as large as 12 Fr or higher. For percutaneous placement into larger vessels such as the iliac artery. Additional dimensions, materials and manufacturing techniques are well known in the angioplasty catheter art.

The proximal end 82 is provided with a manifold 88, having a variety of access ports depending upon the desired functionality of the catheter 80. In the illustrated embodiment, the manifold 88 is provided with a guidewire port 90 and a deployment wire port 94. Manifold 88 may be manufactured by injection molding, or other techniques known in the art.

The distal end 84 of deployment catheter 80 is provided with a collapsed support structure 96 having a sensor housing 20 thereon in accordance with the present invention. The support structure 96 is illustrated in its collapsed, low profile configuration, such as for transluminal advancement towards a placement site. The tubular body 86 may be provided with an annular recess 98 near the distal end 84, for receiving the support structure 96. In addition, the tubular body 86 may be provided with a recess for receiving the sensor housing 20, thereby reducing the collapsed profile of the loaded catheter 80.

The support structure 96 may be constrained in its reduced crossing profile configuration in any of a variety of ways as has been discussed. In this illustrated embodiment, the support structure 96 is restrained in its collapsed configuration by a deployment wire 94. Deployment wire 94 extends throughout the length of the tubular body 86 through a deployment wire lumen 108, such that a proximal end of the deployment wire 94 may be proximally retracted by the clinician. The distal end of the deployment wire 100 exits the tubular body 86 at a deployment wire port 100, and loops the support structure 96 in one or more loops or slip knots 102 to restrain the support structure 96 in its collapsed configuration. Loops or slip knots 102 are configured such that proximal retraction on deployment wire 94 causes the loops or slip knots 102 to become untied or otherwise disengaged, thereby releasing the support structure 96 so that it expands radially outwardly from its low profile introduction configuration to its radially enlarged implanted configuration. For applications in which the deployment site is removed from the percutaneous access site, the catheter 80 is preferably introduced over a guidewire as is known in the art. For this purpose, a distal guidewire opening 104 is in communication with the proximal guidewire port 90 by a guidewire lumen 106 extending therebetween.

An example of a similar delivery system is shown in U.S. Pat. No. 5,873,906 to Lau, et al. issued Feb. 23, 1999, which is herein incorporated by reference.

Figure 7B:
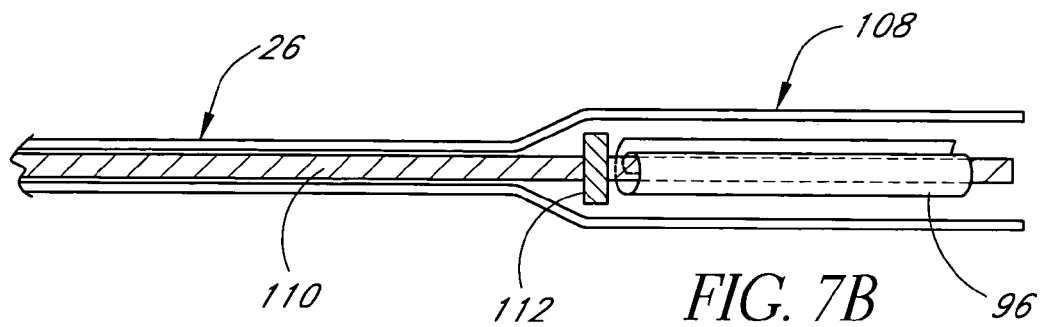
FIG. 7B is a cross-sectional view of a catheter-based delivery system for a rolled sheet type self-expanding stent with an embedded sensor.

Referring to FIG. 7B, the self-expanding implantable sensor device 96 can be deployed from a tubular restraining sheath 108 by pushing a rod 110 optionally attached to a disk 112, until the implantable sensor device 96 is pushed clear of the restraining sheath 108. An example of such a technique is described in U.S. Pat. No. 5,411,551 to Winston et al. (issued May 2, 1995).

Figure 7C:
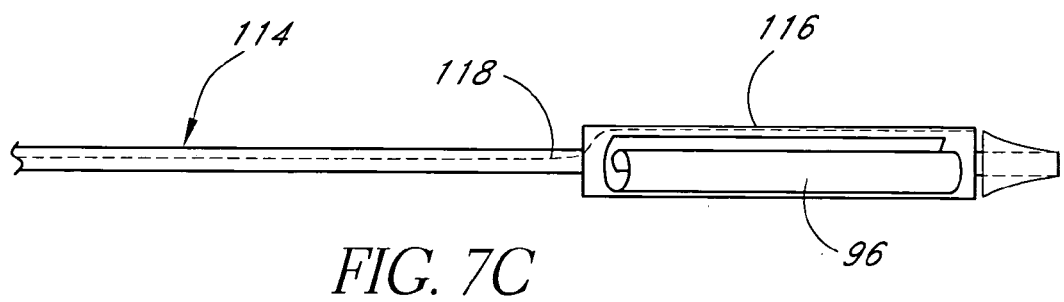
FIG. 7C is a cross-sectional view of a catheter-based delivery system, which uses a restraining sheath, for a self-expanding stent with an embedded sensor.

Referring to FIG. 7C, another deployment method for a self-expanding implantable sensor device 96 is shown. The implantable sensor device 96 is restrained onto the shaft of the catheter 114 by a sheath 116 and a tether line 118. The sheath 116 unfolds when the tether line 118 is pulled, allowing the implantable sensor device 96 to deploy.

Figure 7D:
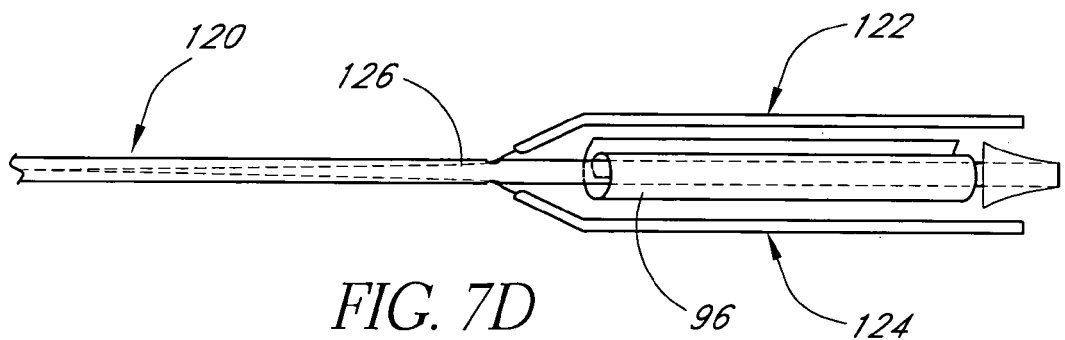
FIG. 7D is a cross-sectional view of a catheter-based delivery system, with a pull-away sheath, for a self-expanding stent with an embedded sensor.

Now referring to FIG. 7D, another deployment method for a self-expanding implantable sensor device 96 is shown. The implantable sensor device 96 is restrained onto the shaft of the catheter 120 by two or three or more restraining prongs 122,124. The restraining prongs 122,124 are retracted when one or more deployment wires 126 are pulled, allowing the implantable sensor device 96 to expand. An example of this can be shown in U.S. Pat. No. 6,024,763 to Lenker et al. (issued Feb. 15, 2000), which is herein incorporated by reference. However, in this patent, the rails are only designed to minimize frictional forces between a deployment sheath and the device. They are not actually used as the deployment mechanism. In the present case, prongs can be used to minimize the delivery profile of the device. Because the sensor and electronic circuitry may not collapse to a profile as small or as circular as a stent or stent-graft, it may be more appropriate to position the electronic components on one side of the catheter, and layer the collapsed stent on the opposite side of the catheter. This could be achieved by use of delivery prongs, as described.

Figure 7E:
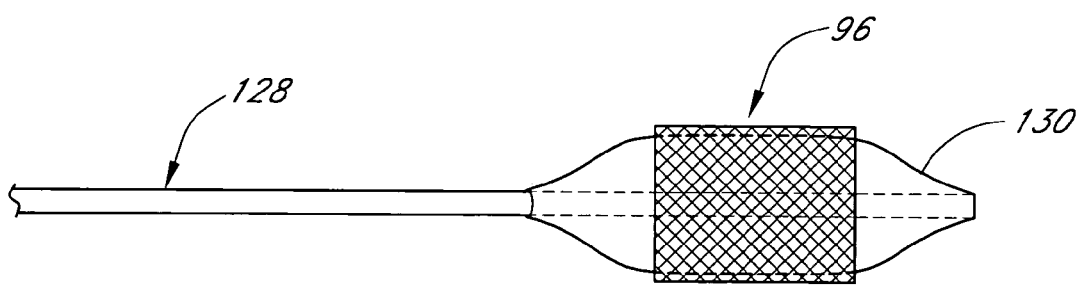
FIG. 7E is a cross-sectional view of a catheter-based delivery system for a balloon expandable stent with an embedded sensor.

Referring to FIG. 7E, the implantable sensor device 96 may be deployed by use of a suitable balloon catheter 128 if a balloon expandable stent platform is used. The balloon 130 is inflated at elevated pressures of 2 to 20 atmospheres, and after the implantable sensor device 96 is fully expanded, the balloon 130 is deflated and then the balloon catheter 128 is withdrawn. Use of such balloon catheters is well known in the art.

Figure 7F:
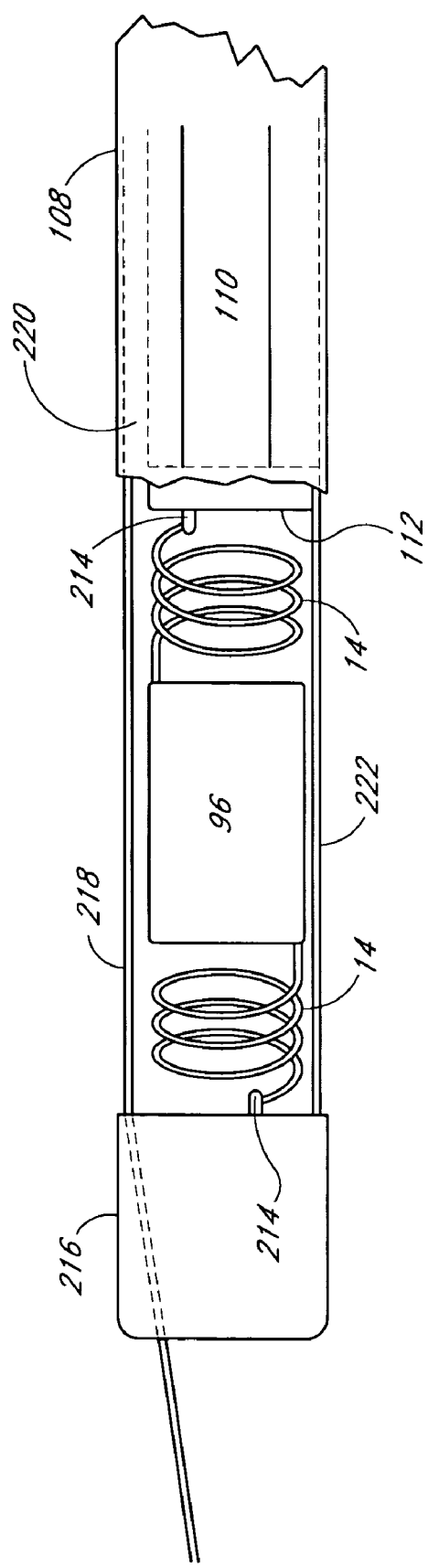
FIG. 7F is a cross-sectional view of a catheter-based delivery system for a self-expanding stent with an embedded sensor, in which the guidewire lumen passes on either side of the sensor.

Referring to FIG. 7F, the self-expanding implantable sensor device 96 can be deployed from a tubular restraining sheath 108 by proximally retracting the sheath 108 with respect to a push rod 110 optionally attached to a disk 112, until the implantable sensor device 96 is exposed clear of the restraining sheath 108. The constrained stent support structures 14 at either end of the sensor 96, may be held in place by a release mechanism, 214, which may be a simple knob or hook. Prior to deployment, the atraumatic catheter tip 216 is in direct apposition to tubular restraining sheath 108. As the sensor device is pushed clear of the restraining sheath, a small shaft 222 connects the push rod 110 or disk 112 to the catheter tip 216. A guidewire 218 passes through guidewire lumen 220, which may be located eccentrically with respect to the axis of the catheter. An example of a similar technique is described in U.S. Pat. No. 5,411,551 to Winston et al. (issued May 2, 1995) which is incorporated herein by reference. However, in Winston, the guidewire passes directly through the center of the catheter, whereas in the present disclosure the guidewire passes eccentrically through the delivery catheter. Allowing the guidewire to pass eccentrically through the catheter allows the sensor to be hermetically sealed, and permits a less complex sensor geometry. Additionally, the eccentric guidewire lumen provides a smaller delivery profile for the sensor and its delivery system.

Now referring generally to FIGS. 5A–C, as the blood passes over the sensor 20, glucose diffuses through the semi-permeable membrane 62. The housing design should keep the blood shear rate at the apex of the housing sufficiently high that there is minimal thrombosis on this surface and any formed thrombus will be of minimal thickness. Thus, diffusion of glucose through the semi-permeable membrane 62 should be the rate-limiting step, and surface of the device should not become covered in a fibrous capsule, as in the case of subcutaneous sensors. The glucose reacts with the glucose oxidase to produce hydrogen peroxide, which further reacts to produce an amperometric signal. The amperometric signal is converted by an appropriately designed electronic circuit so that it may be transmitted using the RF transceiver.

In general, the surface of the sensor 20 should be placed on the luminal side of the stent. With the exception of the glucose permeable membrane, which is part of the sensor, the electronic components of the sensor should be encapsulated in a conformal coating such as a fluoropolymer or a polyamide, and injection-molded or dip-coated in a silicon rubber, polyurethane, or other biocompatible housing material.

The sensor housing should be given a streamlined shape, with gradually sloped transitions at both its proximal and distal ends, in order to minimize flow disturbances. The housing should be as wide or wider at its base than at its apex. The apex of the housing should not protrude higher than 5–50% of the diameter of the fully deployed device. The glucose permeable membrane 62 should be placed at the apex of the housing, should not be encapsulated in the housing material, and should face the bloodstream. The glucose permeable membrane 62 should occupy the majority of the area of the housing apex.

Alternatively, if the device includes a graft on the luminal surface of the stent, the sensor may be placed on either the luminal or abluminal surface of a graft material. If the graft is place on the abluminal surface of the stent, the sensor should be placed on the luminal surface of the graft. The graft material is preferably a fluoropolymer, such as ePTFE. If the housing is placed on the luminal surface of the graft, it is bonded by partially dissolving the housing material thermally or using an appropriate solvent so that the housing becomes physically interpenetrated with the graft or with an appropriate adhesive, such as melt-processed poly(tetrafluoroethylene-co-hexafluoropropylene) (FEP). If the sensor is placed between the stent structure and the graft, it should be bonded to both the stent and the graft; to prevent graft movements from causing thrombosis.

Generally, the height of the sensor is estimated to be 2 to 3 times the thickness of a stent strut, based on some observations of a limited number of stent designs (Virmani, 1999). This estimate represents the approximate thickness of the fibrous tissue layer above the stent surface. Thus, the sensor height above the stent luminal surface should be 1–2 times the thickness of a stent strut. The strut thickness varies with design, but is roughly 0.005" to 0.010" (0.13 to 0.26 mm). Thus, by using this approach, the housing should protrude about 0.2 to 0.5 mm above the stent luminal surface.

The effect that this will have on the target vessel is a function of the diameter of the vessel, as given in the following table:

| Vessel Diameter (mm) | Sensor Height above struts (mm) | Loss in Diameter (%) | Loss in Area (%) |
|---|---|---|---|
| 10 | 0.5 | 5.0 | 9.8 |
| 10 | 0.2 | 2.0 | 4.0 |
| 9 | 0.5 | 5.6 | 10.8 |
| 9 | 0.2 | 2.2 | 4.4 |
| 8 | 0.5 | 6.3 | 12.1 |
| 8 | 0.2 | 2.5 | 4.9 |
| 7 | 0.5 | 7.1 | 13.8 |
| 7 | 0.2 | 2.9 | 5.6 |
| 6 | 0.5 | 8.3 | 16.0 |
| 6 | 0.2 | 3.3 | 6.6 |
| 5 | 0.5 | 10.0 | 19.0 |
| 5 | 0.2 | 4.0 | 7.8 |

As is evident from the table, the smaller the vessel and the greater the sensor height, the greater the obstruction which is created. Design requirements will vary and require investigation for each application as is well known in the art.

This table also provides insights into the intrusion of the sensor as a percentage of post-deployment vessel diameter. A native vessel with greater than 50% diameter stenosis is clinically defined to be a restenotic vessel, and typically requires re-intervention. It is estimated that the sensor should not obstruct more than about 25% of the vessel diameter. Alternatively, the percent area loss of a vessel, along with a sensor height, can be examined and examples are tabulated below:

| Vessel Diameter (mm) | Sensor Height above struts (mm) | Loss in Diameter (%) | Loss in Area (%) |
|---|---|---|---|
| 10 | 0.5 | 5.0 | 9.8% |
| 10 | 2.5 | 25.0 | 43.8% |
| 9 | 0.5 | 5.0 | 9.8% |
| 9 | 2.3 | 25.0 | 43.8% |
| 8 | 0.4 | 5.0 | 9.8% |
| 8 | 2.0 | 25.0 | 43.8% |
| 7 | 0.4 | 5.0 | 9.8% |
| 7 | 1.8 | 25.0 | 43.8% |
| 6 | 0.3 | 5.0 | 9.8% |
| 6 | 1.5 | 25.0 | 43.8% |
| 5 | 0.3 | 5.0 | 9.8% |
| 5 | 1.3 | 25.0 | 43.8% |

Using this approach, the sensor height can range from about 0.3 to 2.5 mm in height above the stent luminal surface.

With regard to flow velocity, flow measurements in piping systems are commonly obtained from the pressure drop across a restriction, such as a Venturi meter. As is discussed above, the restriction should not be greater than about 25% of the vessel diameter. Because the volumetric flowrate, Q, must be the same both proximal to and within the restriction, the velocity within the restriction is related to the upstream velocity by:

$$v_2 = v_1(A_1/A_2)$$

Therefore, for an approximately 25% restriction in diameter, the restriction in area is about 43.8%, and the velocity within the restriction is about 178% of the upstream velocity, and for an approximately 5% restriction in diameter, the velocity within the restriction is approximately 111% of the upstream velocity.

The above analysis is true for situations where the velocity profile is in turbulent flow in a pipe. For laminar flow, there will be a parabolic velocity distribution, with zero velocity at the wall, and maximum velocity occurring in the middle. This distribution may be somewhat impractical to measure, so the exact position where 178% of the proximal velocity occurs may be hard to establish. Thus, another approach to determining the proper height of the sensor is to find the sensor height where the blood velocity is approximately 125–200% of its proximal velocity. This can be determined using duplex ultrasound, or hot-wire anemometry, or other flow-measuring techniques. Using this approach, the sensor may be flush mounted against the wall of the vessel, with a flow impedance device mounted at the same axial position within the vessel, in order to increase the velocity within the sensor/impedance device to about 125–200% of the proximal flow velocity. The location where the estimate of the proximal flow velocity is approximately 200% is preferred. This would allow for the possibility of flush mounted sensors.

One key problem with most implanted sensors is fibrous tissue encapsulation. While proper positioning of the sensor within the vessel can minimize the thickness of a fibrous tissue layer, it may not be possible to avoid endothelialization of the sensor surface. Thus, the sensor design of the current invention may not actually project completely beyond the tissue growth, but the thickness of the tissue layer would ideally be only a single layer of endothelial cells.

Prior to implantation, the sensor may be checked for a reproducible response to glucose concentration. This may be done in the operating theater using sterile technique immediately prior to implantation, or may be done in a batch-wise manner during the manufacturing process. Following implantation, the sensor may then be calibrated by comparison of the output signal with an accepted standard. Typically, this may be done by comparing the signal with the value obtained from a laboratory glucose sensor, such as made by Yellow Springs Instruments (Yellow Springs, Ohio). Preferably, the calibration curve should be stable over time and for wide range of glucose values. For example, the slope of the calibration curve should be sufficiently stable to give an error of less than ten percent. Weekly calibrations should be sufficient to insure stable and accurate readings, however calibration can be performed as frequently as required. For example, there may be a change in sensitivity over the first month or so, if the transducer becomes endothelialized. However, after that point, the system should be stable. Thus, calibrations could be required as often as every other day at first, and taper off to no more than about once per week.

Once calibrated, if the external signal produced by the sensor indicates that the glucose level is outside of the normal physiological range, there are several possible outcomes.

1. An audible, visible or tactile alarm may sound, so that the patient or physician may check the sensor with a home glucose monitoring kit (e.g., One Touch, LifeScan, Johnson & Johnson), and then take appropriate action such as administration of insulin or glucose.
2. The signal may be transmitted directly to an implantable insulin pump, which may administer insulin directly without requiring a response by the patient.

FIGS. 5A–C show various embodiments in which the sensor and transmitter are on either the luminal or abluminal surface of the stent. Now referring to FIG. 5A, an implanted sensor 20 is shown in a transverse cross-sectional view through the vessel. The struts 60 of the implantable sensor device may be surrounded by an inner tubular sheath (not illustrated for simplicity), which would contact the blood vessel wall when deployed. The sensor housing 20 sits between a pair of struts 60. The membrane 62 is exposed to the blood flow. The analyte sensor 56 will normally have a larger cross-sectional area than the stent struts 60. The outer sheath allows for enhanced uniform radial expansion (beyond that of self-expanding struts), especially if the sheath is bonded to each of the struts 60 of the stent, and is bonded through the length of the stent, not just at the ends. This would link each of the struts 60 to its neighbors, preventing uneven expansion. It would also be advantageous to make the sheath out of a material which could be stretched slightly to obtain its final diameter, so that irregularities in the flow surface are minimized, except in the region of the sensor.

When a non-sheath implantable sensor device is either balloon expanded (or in the case of self-expanding stents, following balloon touch-up), the stent struts 60 can be embedded more deeply into the vessel wall than the sensor housing 20. If the struts 60 were positioned between the flowing blood and the sensor surface, they would cause flow stagnation, and therefore thrombosis on the membrane 62 of the sensor. If the sensor is placed instead on the luminal surface of the stent, the sensor will again be embedded less deeply in the vessel wall, although without struts 60 on its luminal surface, there will be minimal hemostasis and thrombus formation on the transducer surface.

As it can be seen, the sensor could be placed either between the stent struts and the inner sheath, or on the luminal surface of the inner sheath. In both cases, a semipermeable membrane might still be necessary to insure that only the analyte of interest reaches the surface of the sensor. In either case, the sensor should be designed with a streamlined profile at both its proximal and distal ends, to minimize regions of hemostasis.

In accordance with another aspect of the invention, the sensor and its associated circuitry are connected between two or more stent segments, with or without the presence of a stent or supporting member at the location of the sensor. This provides a number of advantages, including a decrease in the delivery profile, and an increase in flexibility. This allows easier access to sites with tortuous vascular anatomy, but will still allow the sensor to maintain its same relative position in the blood vessel.

Figure 10:
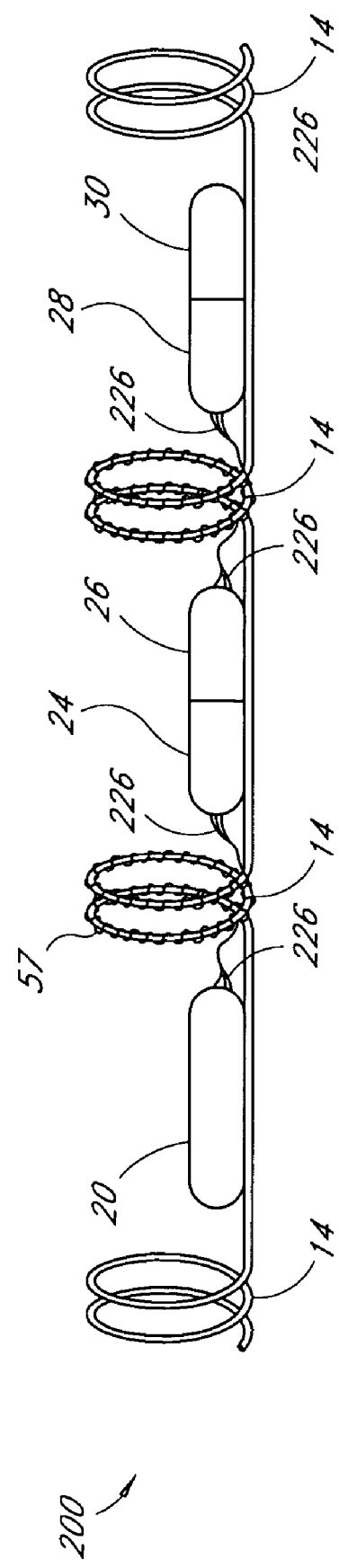
FIG. 10 shows a side elevational view of a sensor and transmitter, with expanded anchoring stents at the proximal end of the sensor, intermediate between the sensor and transmitter, and at the distal end of the transmitter.

FIG. 10 shows a side elevational view of a sensor 20, a sensing circuit 24 and signal processing unit 26, a power source 28 and a radio-transmitter 30, with expanded anchoring stents 14 at the proximal end 200 of the sensor 20, intermediate between the sensor 20 and the sensing circuit 24 and signal processing circuits 26, also intermediate between the sensing circuit 24 and signal processing circuits 26 and the power source 28 and radio-transmitter 30, and at the distal end 210 of the power source 28 and radio-transmitter 30. Each segment of the implantable sensor device is connected to its neighboring segment by the use of electrical connectors 57, with strain relief elements 226. The electrical connectors 57 are hermetically sealed. Additionally, the electrical connectors 57 are of sufficient length, and have redundancies so that they can connect the various segments allowing flexibility of positioning between each segment of the implantable sensor while minimizing the strain imparted on the connectors. It is important to note that the relative position of each of these components between the anchoring stents is somewhat arbitrary. The device could be designed with these components in any order, and still function equally well, as will be apparent to those skilled in the art.

Figure 11:
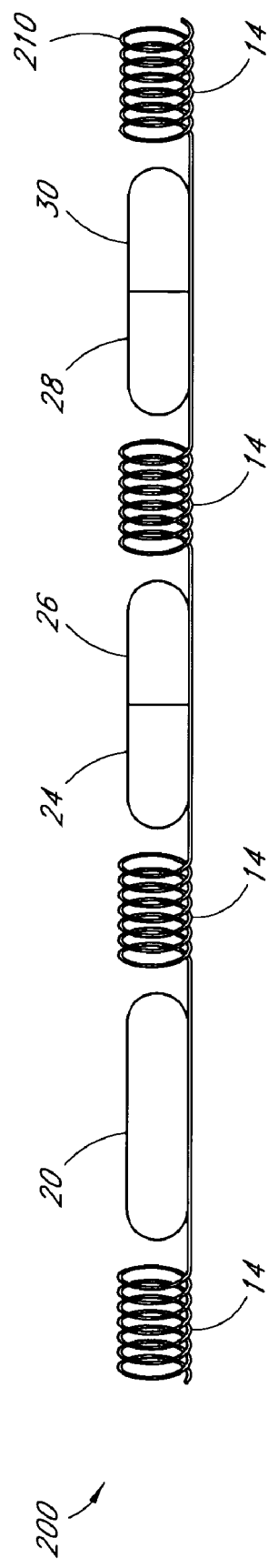
FIG. 11 shows a side elevational view of a sensor and transmitter, with anchoring stents in the compressed state at the proximal end of the sensor, intermediate between the sensor and transmitter, and at the distal end of the transmitter.

FIG. 11 shows a side elevational view of a sensor 20, a sensing circuit 24 and signal processing unit 26, a power source 28 and a radio-transmitter 30, with anchoring stents 14 in the compressed state such as within a tubular deployment catheter at the proximal end 200 of the sensor 20, intermediate between the sensor 20 and the sensing circuit 24 and signal processing circuits 26, also intermediate between the sensing circuit 24 and signal processing circuits 26 and the power source 28 and radio-transmitter 30, and at the distal end 210 of the power source 28 and radio-transmitter 30. The advantages of this segmented embodiment of the invention are that the overall delivery profile of the device is reduced, and the device becomes more flexible for delivery through tortuous vessels.

Thus, the present invention provides at least one electrical component, having at least a first support on a proximal end and a second support on a distal end, for supporting the component in a body lumen. As disclosed herein, the electrical circuitry may desirably be divided into at least two or three discrete physical components spaced axially apart and in electrical communication with each other to minimize the implanted profile and enhance deliverability. Each of the components may be provided with a proximal and a distal support, as illustrated in FIGS. 10 and 11. The two or three or four or more supports may be connected together independently of the intervening electrical component, or may be connected only through the housing of the intervening electrical component. The supports may comprise any of a variety of self-expandable coils or other structures well known in the self expandable stent and graft (e.g., abdominal aortic aneurysm graft) arts. Alternatively, balloon expandable or mechanically expandable anchor structures may be used. In an alternate configuration, the support may comprise an elongated ribbon or wire such as Nitinol which is based into a spiral, having the electrical components spaced axially apart therealong.

In another aspect of this invention, it is possible to monitor substances other than glucose by using different enzymes, as listed in the table below:

| ANALYTE | ENZYME |
| --- | --- |
| glucose | glucose oxidase |
| glucose | glucose dehydrogenase |
| lactate | lactate oxidase |
| 1-methionine | 1-amino acid oxidase |
| 1-phenylalanine | 1-amino acid oxidase |
| d-aspartate | d-amino acid oxidase |
| d-glutamate | d-amino acid oxidase |
| urate | urate oxidase |
| ethyl alcohol | alcohol oxidase |
| methyl alcohol | alcohol oxidase |
| cholesterol | cholesterol oxidase |
| ascorbic acid | ascorbate oxidase |

In still another aspect of the invention, a different class of sensors is used to detect the presence of chemical analytes in blood. These sensors, termed "immunosensors", rely on the interaction between an antibody and its antigen, which are very specific, and typically there is a very strong interaction between antibody and antigen. This type of detection system may have broader applicability for detecting molecules in blood as compared with enzymatic sensors (Rabbany S Y, Donner B L, Ligler F S, "Optical Immunosensors" Crit Rev Biomed Eng 1994; 22(5–6):307–46; and Stefan R I, van Staden J F, Aboul-Enein H Y, "Immunosensors In Clinical Analysis" Fresenius J Anal Chem March–April 2000; 366(6–7):659–68). Antibodies can be produced which can recognize almost any biomolecule, and therefore the number of possible target analytes could be substantially increased using this method. As Stefan et al. (2000) state, "The main problem of [immunosensor] utilization is the interference or loss of affinity when real biological fluids (e.g., blood, serum, plasma, urine, saliva) have to be analyzed." They continue, "For in vivo tests with immunosensors, highly biocompatible materials have to be found for electrode construction" (emphasis added). The present invention provides an excellent method for solving the key issue of immunosensor fouling.

There are a number of potential applications of this technology, including detection of infectious disease, cardiac disorders, and cancer, as well as clinical drug monitoring. (Rabbany 1994). Other potential applications include illicit drug monitoring, and research applications focused on drug development and pharmacokinetics studies. For instance, Hanbury et al. (Hanbury C M, Miller W G, Harris R B, "Antibody Characteristics For A Continuous Response Fiber Optic Immunosensor For Theophylline" Biosens Bioelectron 1996; 11(11):1129–38) describe a continuous immunosensor for monitoring theophylline, a vasodilator with a narrow therapeutic range (55–110 µM), and which requires frequent monitoring to assure therapeutic efficacy and prevent toxicity.

Another important application would be in the area of crisis-oriented diagnostics. For example, heart patients presenting with chest pain, or those at risk for recurrent acute myocardial infarction (AMI), could be quickly diagnosed with AMI by using the present invention to monitor for biochemical markers such as creatine kinase (CK-MB), serum cardiac troponins (cTnT or cTnI), aspartate aminotransferase (AST), lactate dehydrogenase (LDH), beta-hydroxybutyrate dehydrogenase (HBD), serum myoglobin, glycogen phosphorylase isoenzyme BB (GPBB), fatty acid binding protein (FABP), phosphoglyceric acid mutase isoenzyme MB, enolase isoenzyme alpha beta, S100a0, and annexin V (Olukoga A, Donaldson D, "An Overview Of Biochemical Markers In Acute Coronary Syndromes", J Royal Soc Promot Health 121(2):102–106 (2001).) Of potentially greater value is use the present invention to monitor for biochemical markers which may precede AMI, such as C-reactive protein (CRP) (Rabbany 1994), serum TnT, and inflammatory markers such as V-CAM, I-CAM, or interleukin-6 for the prognosis of myocardial infarction. For such applications, speed and accuracy of monitoring are essential.

Other potential uses of this type of immunosensor include monitoring anticoagulation levels, which might include monitoring for thrombin, prothrombin fragment 1+2 (F1+2), fibrinopeptides A or B, Factor Xa, thrombin-antithrombin III complex, or platelet release products such as thromboxane A2, PDGF, or markers of fibrin degradation such as D-dimer, other markers which could potentially serve as an index for a patient's level of anticoagulation. Finally, the prospect of continuous, ambulatory monitoring provides improved therapeutic efficacy, cost containment, convenience, and patient peace of mind.

Continuous immunosensors have been previously demonstrated (Ligler, et al., U.S. Pat. No. 5,183,740 "Flow Immunosensor Method And Apparatus," Feb. 2, 1993; and Ligler, et al., U.S. Pat. No. 6,245,296 "Flow Immunosensor Apparatus," issued Jun. 12, 2001) for the detection of explosives in soil samples, among other applications (Gauger P R, Holt D B, Patterson C H Jr, Charles P T, Shriver-Lake L, Kusterbeck A W, "Explosives Detection In Soil Using A Field-Portable Continuous Flow Immunosensor," J Hazard Mater May 7, 2000; 83(1–2):51–63; Vianello F, Signor L, Pizzariello A, Di Paolo M L, Scarpa M, Hock B, Giersch T, Rigo A., "Continuous Flow Immunosensor For Atrazine Detection," Biosens Bioelectron Jan. 1, 1998; 13(1):45–53; Narang U, Gauger P R, Kusterbeck A W, Ligler F S, "Multianalyte Detection Using A Capillary-Based Flow Immunosensor," Anal Biochem Jan. 1, 1998; 255(1):13–19; Kusterbeck A W, Wemhoff G A, Charles P T, Yeager D A, Bredehorst R, Vogel C W, Ligler F S, "A Continuous Flow Immunoassay For Rapid And Sensitive Detection Of Small Molecules," J Immunol Methods Dec. 31, 1990; 135(1–2):191–7; and Charles P T, Conrad D W, Jacobs M S, Bart J C, Kusterbeck A W, "Synthesis Of A Fluorescent Analog Of Polychlorinated Biphenyls For Use In A Continuous Flow Innunosensor Assay," Bioconjug Chem November–December 1995; 6(6):691–4.) and sample analysis is very rapid (<5 minutes). However, the continuous immunosensors described are not readily translated to the clinical need for ambulatory monitoring. For instance, Ligler (1993) teaches that the level of the target molecule in the system should be measured by determining the amount of label that is released from the apparatus, not the amount of antibody-antigen complex remaining in region of the apparatus. Measuring the amount of the labeled target molecule released into the bloodstream would require that samples be taken from the patient on a frequent basis. This would not provide any benefit over using a standard enzyme-linked immunosorbent assay (ELISA) or radioimmunoassay (RIA) to look for this same unlabeled analyte of interest.

As described in FIGS. 1–5 and 9–11, above, the sensor 20 may in a preferred alternative embodiment, be an immunosensor. The anchoring platform for this embodiment of the invention is similar to that which was previously described in the context of electrochemical glucose sensors, as is the positioning of the sensor 20 and radiotransmitter 30 with respect to the anchoring platform 14, and the radiotransmitter 30 for sending the signal to the external device. A power source 28, sensing circuit 24, and a signal processing circuit 26 are also included with the immunosensor. The external device provides a read-out of the data regarding the concentration of analyte in the patient's blood at any time, and appropriate audible, visual, vibratory, or other signals are given to notify the user of an important change in condition.

As with enzymatic glucose sensors, there are a multiplicity of ways in which the molecular recognition event (i.e., the antibody-antigen reaction) can be translated into an electrical signal. These include amperometric, potentiometric, piezoelectric, surface plasmon resonance (SPR), scintillation, acoustic, fluorescent and chemiluminescent immunosensors (Stefan 2000). These types of sensors have been previously described in the literature (Stefan 2000).

Amperometric sensors typically use enzymes (Rabbany 1994) such as alkaline phosphatase or horse-radish peroxidase to label antigens or antibodies, so that the reaction products produced by the enzyme (rather than the antibody or antigen) provide the actual signal to be detected (Stefan 2000). This adds a level of complexity for an implantable device, because a third component is now required, in addition to the antibody and antigen. For this type of immunosensor, not only are the antigen of interest and an enzyme-labeled antibody required, but an appropriate substrate for the enzyme label is also required. This enzyme substrate can be delivered under conditions to insure that the signal being produced is determined by the amount of enzyme-labeled antibody present, rather than the amount of substrate for the enzyme.

Potentiometric sensors have excellent reproducibility, although according to Stefan (2000), "in most cases, potentiometric transducers cannot provide the necessary sensitivity for the antigen-antibody reaction." This is because the resulting signal is proportional to the logarithm of the analyte concentration.

Piezoelectric sensors, such as those based on the quartz-crystal microbalance (QCM) may not be well suited to this application, due to the high background response from non-specific adsorption (Stefan 2000). Surface plasmon resonance detection is also less well suited to the present application, due to interference from non-specific binding (Rabbany 1994, Stefan 2000).

In principal, detection could be performed by the use of antigens labeled with radionuclides. In that case, a scintillation detector such as a NaI crystal coupled with a photodiode or photomultiplier tube could be used. The detector for this type of sensor is otherwise similar to that described below for the fluorescence detectors. However, the use of radionuclides as labeling agents is less attractive, due to problems with handling, and exposure of the patient and physician to radiation.

Figure 12:
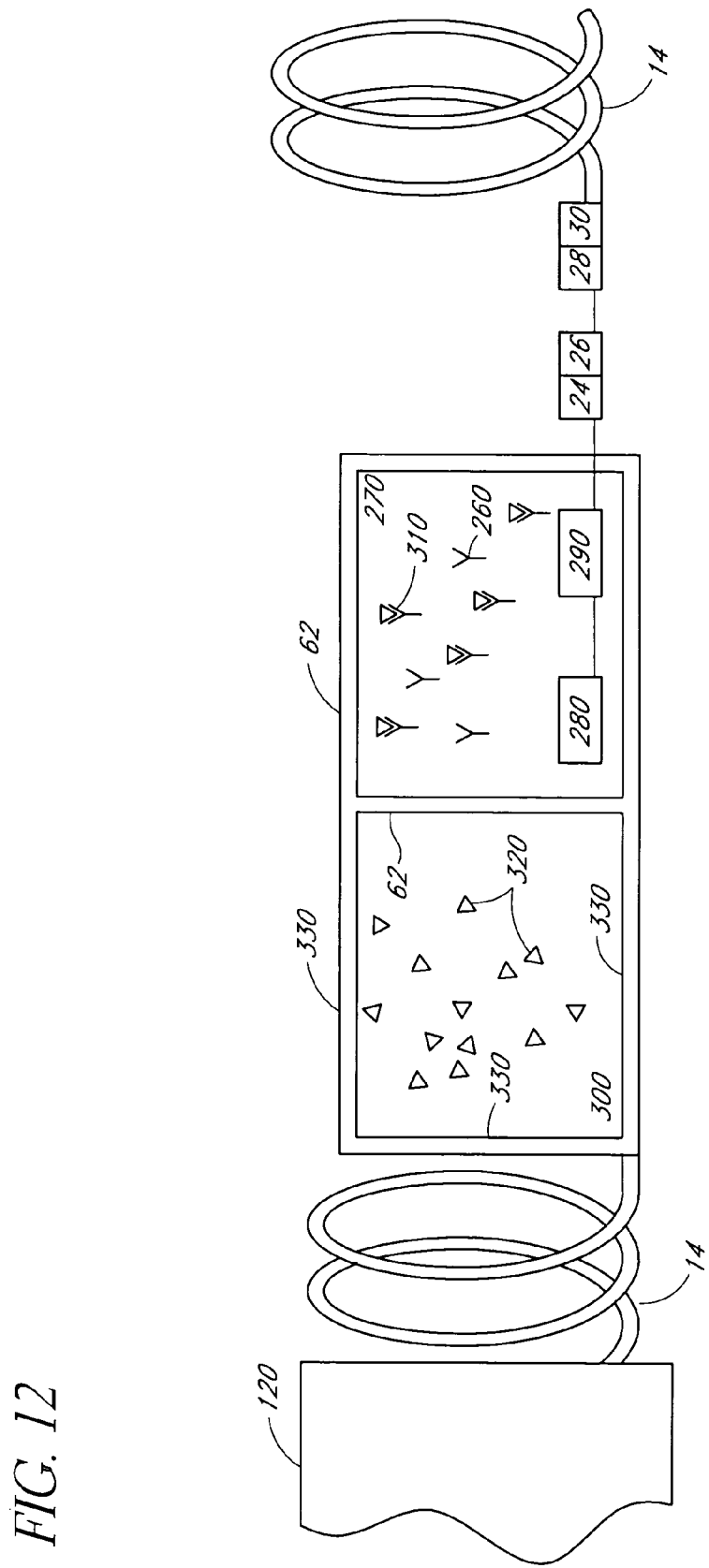
FIG. 12 is a diagram of a constrained anchoring platform or stent with a sensor housing containing a reservoir for delivery of labeled target molecules, and a sensing compartment containing a signal source, a receiver and antibodies with and without labeled target molecules, signal processing circuitry, and a radiotransmitter.

Optical immunosensors include fluorescent or chemiluminescence-based sensors. A fluorescence-based sensor is shown in FIG. 12, and is supported by a stent structure 14 which is in the compressed state for delivery from a catheter 120. In this sensor, the labeled target molecule 260 has a fluorescent label, such as fluorescein, tetramethylrhodamine, or Texas Red. If a fluorescent label is used, the sensor will consist of both a light source 280 such as a light-emitting diode (LED), and a photosensitive detector such as a photomultiplier tube or photodiode 290, such as that supplied by Silicon Sensors (Madison, Wis.). The light source 280 with a filter (not shown) produces light at the excitation wavelength $\lambda_1$, and the photodiode 290 with a filter (not shown) detects the light at wavelength $\lambda_2$ emitted by the fluorescence of the label. In the case of fluorescein, the wavelength of light that is absorbed by the label is in the range of 470 nm, and the wavelength of fluorescent light is in the range of 540 nm. The sensing circuit 24 and radiotransmitter 30 are also included. The intensity of light detected by the photodiode provides an electrical signal, which is dependent upon the intensity of the detected fluorescence. A change in signal level will indicate a change in the concentration or presence of the antigen of interest.

FIG. 12 also shows a sensor 20 containing a reservoir 300 of labeled antigen 320 which is included as part of the sensor. The reservoir is encapsulated on all but one side by a membrane 330 that is impermeable to the analyte of interest. The impermeable membrane may be a poly(carbonate urethane), silicone rubber, Parylene, Teflon, or water-impermeable polymer. A semi-permeable membrane 62 is included on the final side of the reservoir, which adjoins the sensor compartment as a semi-permeable barrier to control the rate at which the labeled antigen diffuses from the reservoir to the sensing compartment. The semi-permeable membrane 62 is preferably a hydrogel, such as poly(ethylene glycol) (PEG), poly(vinyl alcohol) (PVA), poly(N-vinyl pyrrolidone) (PVP), polyacrylamide, poly(acrylic acid) (PAA), poly(hydroxyethyl methacrylate) (PHEMA), or other. The thickness, chemical nature, and cross-link density of the hydrogel can be controlled as is known by those skilled in the art in order to obtain an appropriate rate of diffusion of labeled antigen out of the reservoir, and into the sensor compartment. Further, this semi-permeable membrane 62 may contain multiple layers, such as a hydrogel bonded to a dialysis membrane, polyurethane, poly(vinylidene fluoride) (PVDF), ePTFE, Nafion, or other second membrane layer. The reservoir provides a flux of labeled target molecule which allows the sensor to be replenished over time, and allows the measurement of both decreases and increases in analyte concentration in the blood. The reservoir provides the added benefit of extending the lifetime of the sensor.

The sensor for this embodiment detects the presence of the target molecule as follows. First, an antibody 260, which hereafter refers to any of combination of polyclonal antibodies, monoclonal antibodies, or the Fab fragment of an antibody, is immobilized on or near the sensor light source 280 and photodetector 290. The antibodies may be from human, mammalian, or non-mammalian origins, provided that adequate cross-reactivity between the antibody and antigen can be established. The antibodies may be immobilized within or upon films (not shown) or membranes (not shown) that may be present on the surface of the light source 280 or photodetector 290. In addition, the antibodies may be immobilized onto particulate supports near the sensor component, such as Sepharose (Pharmacia). The immobilization may be performed by covalently bonding the antibody to the substrate with bi-functional molecules such as glutaraldehyde, carbodiimides, biotin-avidin, and other molecules with one or more functional groups on each of at least two ends as are well known to those skilled in the art. Additionally, bi-functional spacer molecules such as N-hydroxysuccinimide derivatized polyethylene glycols may be used to bind the antibody within the sensor compartment. Because immobilization of antibodies can significantly change their reactivity, methods for improved orientation of the antibodies have been described (Stefan, 2000). During the manufacture or final preparation of the device, prior to implantation in the patient, the antibody is saturated with a large excess of labeled antigen, beyond the stoichiometric excess needed to fully occupy all the available sites on the antibodies.

In comparison with enzymatic electrochemical sensors, immunosensors may preferably be modified so that the luminal sensor surface is positioned even closer to the center of the blood vessel in order to further reduce endothelial coverage, because not all antigens are capable of passing through an endothelial layer. The outer membrane 62 covering the luminal surface of the sensor is preferentially a hydrogel, such as poly(ethylene glycol) (PEG), poly(vinyl alcohol) (PVA), poly(N-vinyl pyrrolidone) (PVP), poly(hydroxy ethylmethacrylate) (PHEMA), or other, in order to further reduce the probability of cell adhesion to the surface. It may also come from the group consisting of ePTFE, polyurethane, silicone rubber, cross-linked collagen, polypropylene, cellulose acetate, poly(vinylidene fluoride) (PVDF), Nafion or other biocompatible material. The outer membrane must also be permeable to the analyte of interest. The permeability of the membrane is selected to allow the analyte of interest to freely contact the sensor, while restricting the passage of other blood components. The permeability of this membrane 62 can be controlled by varying the porosity of the hydrogel or polymer, which can be controlled by varying the cross-link density and the molecular weight of the polymer between cross-links. Additionally, the thickness of the outer membrane can be controlled, allowing control of the transport rate of the target analyte. Finally, the outermost membrane may be bonded to a second, inner membrane layer which may be made from either ePTFE, polyurethane, silicone rubber, cross-linked collagen, polypropylene, cellulose acetate, poly(vinylidene fluoride) (PVDF), Nafion, or other biocompatible membrane material with controlled porosity to further control the transport of the target molecule to the sensor.

As the sensor is exposed to flowing blood containing the antigen of interest, there will be a competition for the antibody binding sites on the sensor between the labeled antigen (both that originally implanted in the sensor compartment 270 and that contained in an additional reservoir 300 of labeled target molecules) and the antigen in the bloodstream. Over time, there will be a displacement of the labeled antigen originally supplied in the sensor by the non-labeled antigen, which is present in the bloodstream. Rabbany (1994) reports that the antibody-antigen reaction is seen as nearly irreversible except in the case of continuous-flow immunosensors. Because of this, only when unlabeled antigen is present in the continuously flowing blood is the labeled antigen displaced. Thus, if no antigen is present in the blood, the sensor will remain undepleted. The amount of antigen-antibody complex 310 can be measured on a very frequent (nearly continuous) basis. To do this, the LED emits a pulse of light, and the resulting fluorescence intensity is measured by the photodiode.

Figure 13:
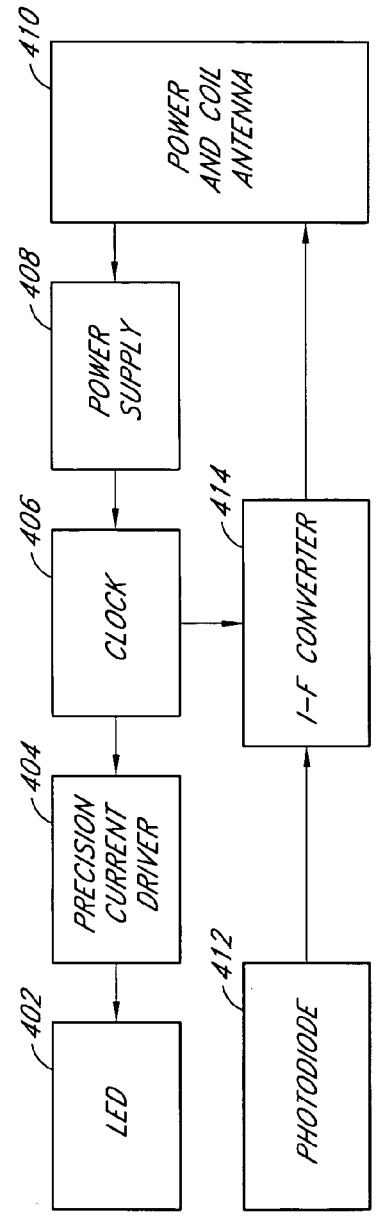
FIG. 13 is a block diagram of the fluorescence based sensor electronics of the sensor of FIG. 12.

Now referring to FIG. 13, the light emitting diode sensor circuit consists of a constant-current LED drive circuit 404 that ensures consistent brightness over a range of input voltages. The LED 402 is controlled by a square wave clock circuit 406 that gates the LED 402 on and off at rate that can be set for the particular application. This type of sensor is powered by the power supply 408 via the power coil/antenna 410.

The light detector circuit consists of a photodiode 412 and a current-to-frequency converter 414. The I-F converter output is gated by the clock 180 degrees out of phase with respect to the signal used to drive the LED. This ensures that there is no output from the converter when the LED is being driven.

Figure 14B:
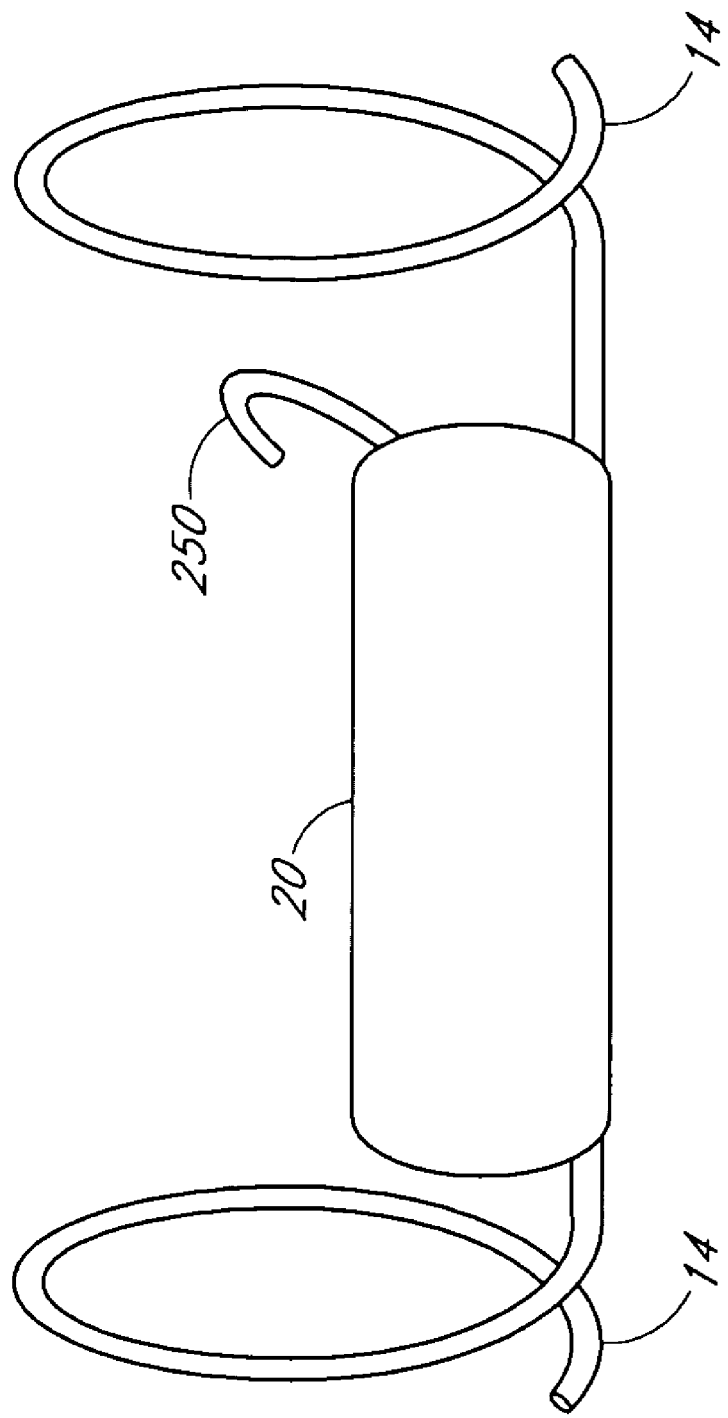
FIG. 14B is a diagram of an expanded anchoring platform or stent with an embedded sensor housing on its luminal side, and containing a hook on the sensor housing with which the device can be retrieved.
Figure 15A:
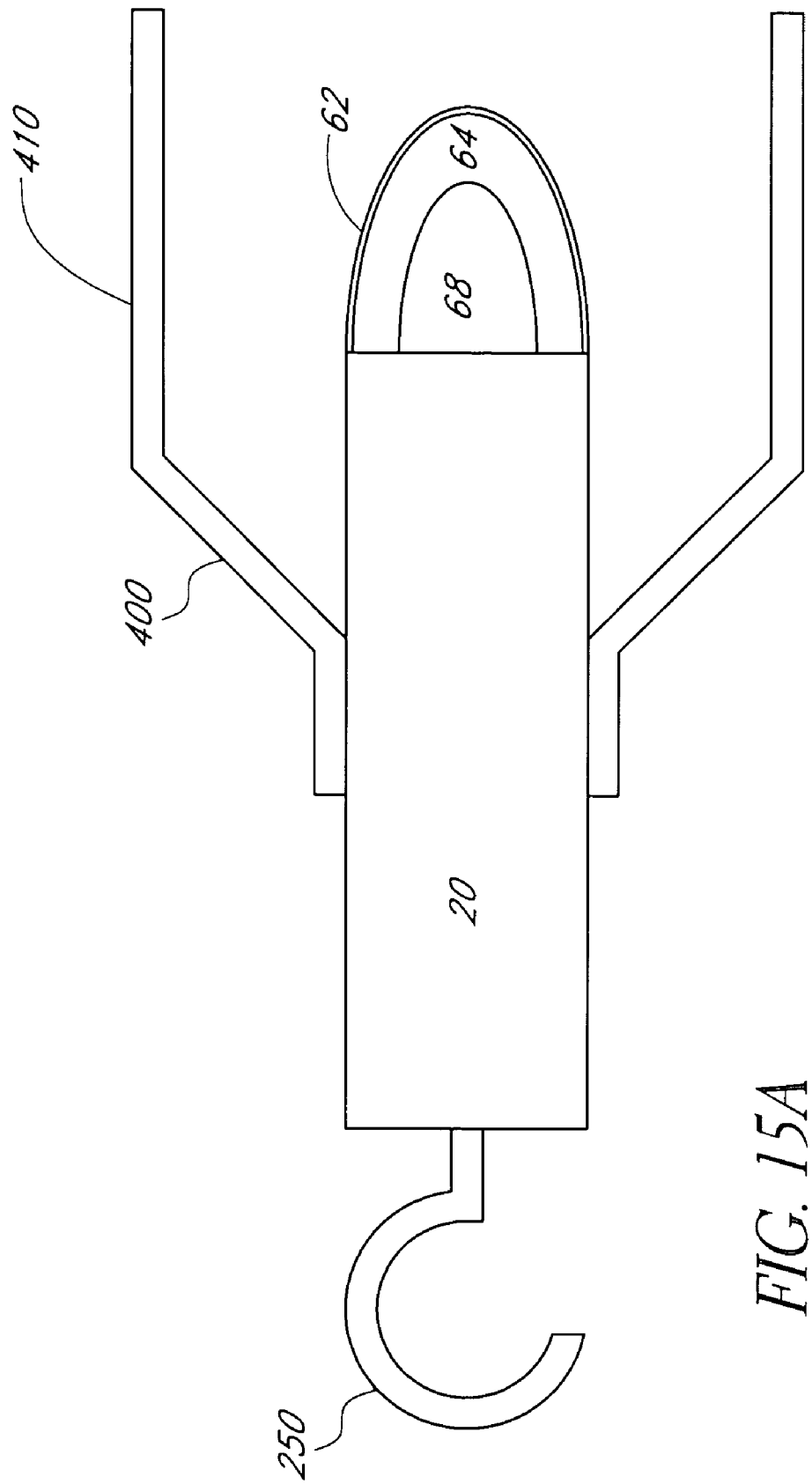
FIG. 15A is a side view diagram of an expanded anchoring platform with an embedded sensor, which is placed centrally in a vessel, and containing a hook on the sensor housing with which the device can be retrieved.

In an alternate embodiment, the reservoir can instead be fabricated from a degradable material such as poly(lactide-co-glycolide) (PLGA), polycaprolactone (PCL), or other controllably degradable material. The labeled target molecule is incorporated into such a matrix by mixing the target molecule directly into a solution of PLGA, and precipitating the PLGA. Alternatively, the reservoir is loaded with microspheres containing either the antibody or antigen of interest (Ma J, Luo D, Qi W, Cao L, "Antitumor Effect Of The Idiotypic Cascade Induced By An Antibody Encapsulated In Poly(D,L-Lactide-Co-Glycolide) Microspheres," Jpn J Cancer Res 92(10); 1110–15, (2001); Torche A M, Le Corre P, Albina E, Jestin A, Le Verge R, "PLGA Microspheres Phagocytosis By Pig Alveolar Macrophages: Influence Of Poly(Vinyl Alcohol) Concentration, Nature Of Loaded-Protein And Copolymer Nature," J Drug Target 7(5):343–54 (2000); Mordenti J, Thomsen K, Licko V, Berleau L, Kahn J W, Cuthbertson R A, Duenas E T, Ryan A M, Schofield C, Berger T W, Meng Y G, Cleland J, "Intraocular Pharmacokinetics And Safety Of A Humanized Monoclonal Antibody In Rabbits After Intravitreal Administration Of A Solution Or A PLGA Microsphere Formulation," Toxicol Sci 52(1): 101–6, (1999)). These microspheres may be prepared by emulsion polymerization, as is known in the art. It is possible to control the release rate of labeled target molecule from these degradable microspheres by varying the co-polymer composition and particle size. For example, a 50:50 ratio of lactide to glycolide monomers is known to degrade more rapidly than homopolymers of either poly(lactide) or poly(glycolide). One difficulty with these types of systems is that as the matrix degrades, its by-products can affect the pH of the local micro-environment. This may have an effect on the stability and solubility of the labeled antigen. A solution to this may be found by incorporating basic salts, such as magnesium hydroxide, calcium hydroxide, calcium phosphate, or zinc sulfate, in order to maintain a pH neutral environment, as described by Zhu et al (Zhu G, and Schwendeman S P, "Stabilization of Proteins Encapsulated in Cylindrical Poly(lactide-co-glycolide) Implants: Mechanism of Stabilization by Basic Additives", Pharm Res 17(3): 351–7 (2000)). Another approach by Jiang (Jiang W, and Schwendeman S P, "Stabilization and Controlled Release of Bovine Serum Albumin Encapsulated in Poly(D,L-lactide) and Poly(ethylene glycol) Microsphere Blends", Pharm Res 18(6): 878–885 (2001)) is to blend a highly water-soluble polymer such as poly(ethylene glycol) (PEG), poly(N-vinyl pyrrolidone) (PVP), or poly(vinyl alcohol) (PVA), with a more slowly degrading homopolymer, such as poly(lactide) (PLA) or poly(glycolide) (PGA). However, the only requirement for the present invention is that the microsphere delivery system is able to maintain antigenic recognition of the labeled target molecule. It is not necessary that the activity of the target molecule be maintained.

One of the difficulties with measuring the amount of labeled antigen-antibody complex still present near the sensor, however, is that of sensor response time. That is, if the amount of label bound to the sensor is relatively large compared to the amount which is displaced, it will be difficult to accurately determine the concentration of the analyte. This is because the difference between two large and uncertain numbers also has a high degree of uncertainty. Thus, the current approach will have a somewhat longer sensor response time, or require a larger change from baseline, and hence have a somewhat lower sensitivity, as compared to the approach described by Ligler (1993), in order to establish a measurable change in antigen level. Sensor response times are dependent on the concentration of antigen in the bloodstream, the rate at which the antigen is transported across the semi-permeable membrane, the reaction rate between antigen and antibody, and the rate at which the displaced, labeled antigen is transported out of the sensor compartment, into the bloodstream. In addition, the relative concentrations of labeled antigen from the reservoir and unlabeled antigen from the bloodstream, which are present in the sensor compartment, will also play an important role. Similarly, the lifetime of the sensor will be dependent on the factors listed above, as well as the amount of labeled target molecule incorporated in the reservoir. If the sensor lifetime were limited by the amount of labeled target molecule incorporated in the reservoir, it may be possible to extend the sensor lifetime, for example, by re-loading the sensor with controlled-release microspheres in a secondary catheterization procedure, or by direct injection with a syringe and needle.

In an alternative embodiment, it is possible to immobilize the antigen, and label the target antibody, in order to monitor the presence of antibodies in the bloodstream. This is done by reversing the immobilization of the antigen near the sensor, and providing a reservoir of labeled antibody as described above for FIG. 12. This may be useful for monitoring patients with conditions such as HIV or AIDS.

The implantable sensor described, could also be made to be retrievable. (Neuerburg, J, Gunther, R W, Rassmussen, E, Vorwerk D, Tonn K, Handt S, Kupper W, Hansen J V, "New Retrievable Percutaneous Vena Cava Filter: Experimental In Vitro And In Vivo Evaluation," Cardiovasc Intervent Radiol 16(4): 224–9 (1993); Neuerburg, J M, Gunther, R W, Vorwerk D, Dondelinger R F, Jager H, Lackner K J, Schild H H, Plant G R, Joffre F G, Schneider P A, Janssen J H, "Results Of A Multicenter Study Of The Retrievable Tulip Vena Cava Filter: Early Clinical Experience," Cardiovasc Intervent Radiol 16(4): 224–9 (1993); and Millward S F, Oliva V L, Bell S D, Valenti D A, Rasuli P, Asch M, Hadziomerovic A, Kachura J R, "Gunther Tulip Retrievable Vena Cava Filter: Results From The Registry Of The Canadian Interventional Radiology Association," J Vasc Interv Radiol 12(9): 1053–8 (2001).) At any point up to a biologically determined retrieval limit, it is possible to remove both the sensor and its anchoring platform, using a device such as the GooseNeck Snare (Microvena Corp.) in a follow-up catheterization procedure.

As shown in FIG. 14A, the anchoring platform 14 can be designed with a hook, loop, eye, or other easily snareable feature 250 such as at the downstream end, so that it can be removed up to a certain period of time without the necessity of leaving the device permanently implanted in the patient. In this example, the hook is preferably made of the same material as the anchoring platform, such as 316L stainless steel, or nitinol, and may either be laser-cut from the same tubing stock as the anchoring platform, or may be laser-welded onto the anchoring platform. The hook may preferably have a diameter greater than that of the retrieval snare wire, typically 0.020–0.030" in diameter, so that the retrieval snare can easily rest in the hook. As an alternative to a hook, a feature such as a ball with a diameter of about 0.75 to 2 mm may be formed at the end of straight segment of wire with a diameter of about 0.5 mm. The hook may also be shaped like a closed loop, or like an anchor, with each arm of the anchor having a length of about 0.5 to 1 mm. In FIG. 14A, the snareable feature 250 on the anchoring platform protrudes slightly into the lumen of the vessel, so that it does not become completely encapsulated in tissue. In an alternative embodiment, as shown in FIG. 14B, the snareable feature 250 is mounted to the distal end of the sensor housing 20. Typically in order to prevent corrosion, the sensor electronics will be hermetically sealed using either a glass, ceramic, epoxy, or metal housing. In this case, the snareable feature may be either laser-welded to the metal housing, or embedded in the glass, ceramic or epoxy at the time the hermetic seal is formed.

The sensor housing may be coupled to the anchoring platform using mechanical clips designed to release under the appropriate applied force, or using degradable materials such as PLGA or PLA. Because the luminal surface of the sensor housing is designed so that it does not become encapsulated with fibrous tissue, it is possible to retrieve the sensor component at any time following implantation. However, with degradable materials, the implant must remain in place long enough for these degradable anchors to lose their strength and give way during retrieval. The anchoring platform is left behind. In these embodiments of the invention, the snareable feature makes the device suitable for continuous monitoring of a temporary patient condition. It is also suitable for short-term monitoring of drugs, such as those with a narrow window between efficacy and toxicity. In addition, it is possible to remove a sensor that may no longer be functional.

Now referring to FIGS. 15A and 15B, in an alternative embodiment, both the sensor and its anchoring platform could be designed to be retrievable for an indefinite period. In this case, the sensor 20 is centrally mounted in an anchoring platform 400. The sensor housing may be bonded to the platform by positioning the two components in close proximity during the formation of a hermetic seal, using glass, metal, or epoxy, as described above for FIG. 14A. Additionally, if the sensor is hermetically sealed in a metal case, the sensor and anchoring platform could be laser-welded together. Another means of connecting the two components would be by mechanical interfit. The anchoring platform 400 contains side struts 410 which extend axially within the vessel. The anchoring platform 400 is preferably made of a self-expanding material such as nitinol. This anchoring platform 400 centers the sensor 20 in the middle of the flowstream, so that the proximal (upstream) tip of the sensor is again kept free of thrombus or other fouling tissue because of the high flow velocity. The side struts 410 also help to keep the sensor centered in the bloodstream. These side struts 410 may have a length ranging from 1 to 100 mm, with longer struts providing improved ability to prevent the sensor from tipping away from the center of the vessel, and shorter struts making the entire device easier to introduce into the vasculature, and also being easier to retrieve. A preferred length range for the side struts 410 is from 5 to 30 mm. The side struts 410 may contain radially outwardly directed hooks (not shown) to prevent the device from migrating. These migration-resistant hooks could be placed at any position along the side struts, and are oriented in a direction to prevent migration of the device towards the heart or lungs. As described in U.S. Pat. No. 6,258,026, to Ravenscroft et al., issued Jul. 10, 2001, the hooks could be made small enough so that they prevent sensor migration, but can be easily deformed during retrieval, allowing the device to be withdrawn from the vessel. The proximal tip of the sensor is preferably in a streamlined configuration, such as a parabola or a cone, to minimize the risk of thrombus formation. A hook 250, knob, or other easily snareable feature is placed at the distal (downstream) end of the sensor. The entire device can then be removed in a catheterization procedure by using a snare as previously described to catch the hook 250 and draw the anchoring platform into the distal end of a tubular retrieval catheter. Because the parallel struts 410 of the anchoring platform 400 are open-ended, they will not become mechanically interlocked by neointimal tissue, and therefore the entire device will be retrievable for an indefinite period. The retrieval process would be much like withdrawing a hypodermic needle from under the skin.

It is possible to remove both the sensor and its anchoring platform, using a snare in a follow-up catheterization procedure. As is well known to those skilled in the art, the snare would be introduced into the vasculature using the same Seldinger techniques that are used to implant a stent. Under fluoroscopic guidance, the physician would first select an appropriate vascular access site, and then would insert a guiding catheter of sufficient diameter so as to be able to accommodate the retrieved sensor and its anchoring platform. Next, the physician would insert a snare, such as the GooseNeck Snare (Microvena Corp.) through the guiding catheter, and approach the sensor hook with the snare. Once the physician grasps the sensor hook with the snare, and proximally retracts the snare, the sensor would collapse into the retrieval catheter, and the sensor and guiding catheter could be simultaneously withdrawn from the patient's body.

There are at least two types of sensors which are used in monitoring arterial blood gas values, and which are suitable for practicing this invention. The first type is a Clark-type electrode, in which an electrochemical reaction, such as the reduction of $O_2$, occurs at an electrode, and an electrical current is monitored. Early oxygen electrodes required initial calibration against a simultaneous ABG sample, and sensor drift necessitated frequent recalibrations. Thrombosis was also a critical issue for this type of intravascular sensor, and so the oxygen electrode was not widely accepted. (Mahutte, 1998). In addition, electrochemical pH and $pCO_2$ monitors are not available.

The other major category of IABG's is optodes, which measure blood gases optically, and are suitable for practicing the present invention. These sensors are based on fiberoptics that are coupled with a reagent. Interaction between the reagent and an analyte of interest results in a change in the optical properties of the reagent, which is detected through the fiber-optic. Optical sensors such as these do not require the use of a reference electrode. There are three main types of optodes, based on either absorbance, fluorescence, or quenching (W. R. Seitz, "Chemical Sensors Based on Fiber Optics", Anal. Chem. 56(1):16A–34A (1984) and C. K. Mahutte, "On-line Arterial Blood Gas Analysis with Optodes: Current Status," Clin. Biochem 1998; 31:119–130). When light of a certain wavelength passes through a reagent, and there is a reduction in intensity of the light, that is termed absorbance. Fluorescence optodes work because the reagent absorbs light at one frequency, and re-emits light at a second frequency. The intensity of light at both frequencies can be measured, providing a correlation with the concentration of the analyte of interest (L. A. Saari and W. R. Seitz, "pH sensor based on immobilized fluoresceinamine", Anal. Chem. 1982; 54:821–23). Fluorescence quenching is also used for detection of analytes such as oxygen. Oxygen can reduce the amount of fluorescence of certain organic compounds, and therefore the reduction in the intensity of re-emitted light can be used as the basis for measurement of oxygen concentration (J. I. Peterson et al., "Fiber-Optic Probe for In Vivo Measurement of Oxygen Partial Pressure", Anal. Chem. (1984) 56:62–67)).

The reagent phase of an optode can be positioned at any point along the fiber-optic, either at the end, or along the sides, allowing for different geometric configurations to be used (Mahutte 1998).

There have been a number of ABG sensors that have reached commercialization at various times and these would be suitable for practicing the present invention. These include the Paratrend 7 (Pfizer/Biomedical Sensors, Malvern, Pa.) (I K Weiss, et al, "Continuous arterial gas monitoring: Initial experience with the Paratrend 7 in children," Intensive Care Med. (1996) 22:1414–1417), the CDI 1000 (Cardiovascular Devices, Irvine Calif.), Optex Biomedical (TX), and the PB3300 (Puritan-Bennett, Carlsbad, Calif.) (T. Lumsden, et al. "The PB3300 Intraarterial Blood Gas monitoring system," J. Clin. Monit 1994; 10:59–66).

The Paratrend 7 is a combination electrode-optode system, with fiberoptic pH and $pCO_2$ sensors, an amperometric oxygen sensor, and a thermocouple for temperature compensation, and would be suitable for practicing the present invention. The CDI 1000, the Optex sensor, and the PB3300 are pure optode systems. In the PB3300, the reagent is on the external circumference of the sensor. Acceptable levels of accuracy have been reported with the PB3300 system, but the longest reported duration of implantation was 121 hours.

In addition, U.S. Pat. No. 5,326,531 Jul. 5, 1994 to Hahn et al., "$CO_2$ Sensor using a hydrophilic polyurethane matrix and process for manufacturing" describes a $CO_2$ optode, and U.S. Pat. No. 5,378,432 Jan. 3, 1995 to Bankert et al, "Optical Fiber pH microsensor and method of manufacture" describes a pH optode, both of which can be used in the present invention.

The clinical issues identified which prevent the sensors from functioning properly in vivo are known as the "wall-stress effect", and are attributed to hypotension or vasoconstriction. In some instances, the pH, $pCO_2$ and $pO_2$ values are variable due to thrombus formation at the tip of the catheter, while in other instances, the variation was due to the sensor touching the arterial wall, and measuring gas values in the tissue (C. K. Mahutte, "On-line Arterial Blood Gas Analysis with Optodes: Current Status," Clin. Biochem 1998; 31:119–130). Both vasospasm and wrist flexion have been identified as factors which negatively affect the performance of these sensors. The anchoring platform (14) shown in FIG. 16 is designed to address these problems.

In U.S. Pat. No. 6,447,395 (Nov. 5, 2002), Schulman et al. shows a sensor designed to avoid direct contact between the sensing surface and the vessel wall. This sensor is built near the tip of a catheter, and the catheter at the sensing surface is bent in a zig-zag shape. However, there are two major drawbacks with this type of design. First, blood flow stagnation will occur in the region at the inside apex of the zig-zag, and therefore, thrombosis will occur on this sensing surface, and interfere with sensor function, even if the sensor surface does not touch the vessel wall. Second, because most catheters are made from somewhat rigid materials, such as nylon, any catheter with a zig-zag pattern as shown in FIG. 6 of Schulman would not be able to be introduced into a vessel using a catheter sheath introducer, as is standard clinical practice. In addition, such a sensor could not be introduced into a vessel using a trocar or other small diameter tool to allow vessel access.

Figure 16:
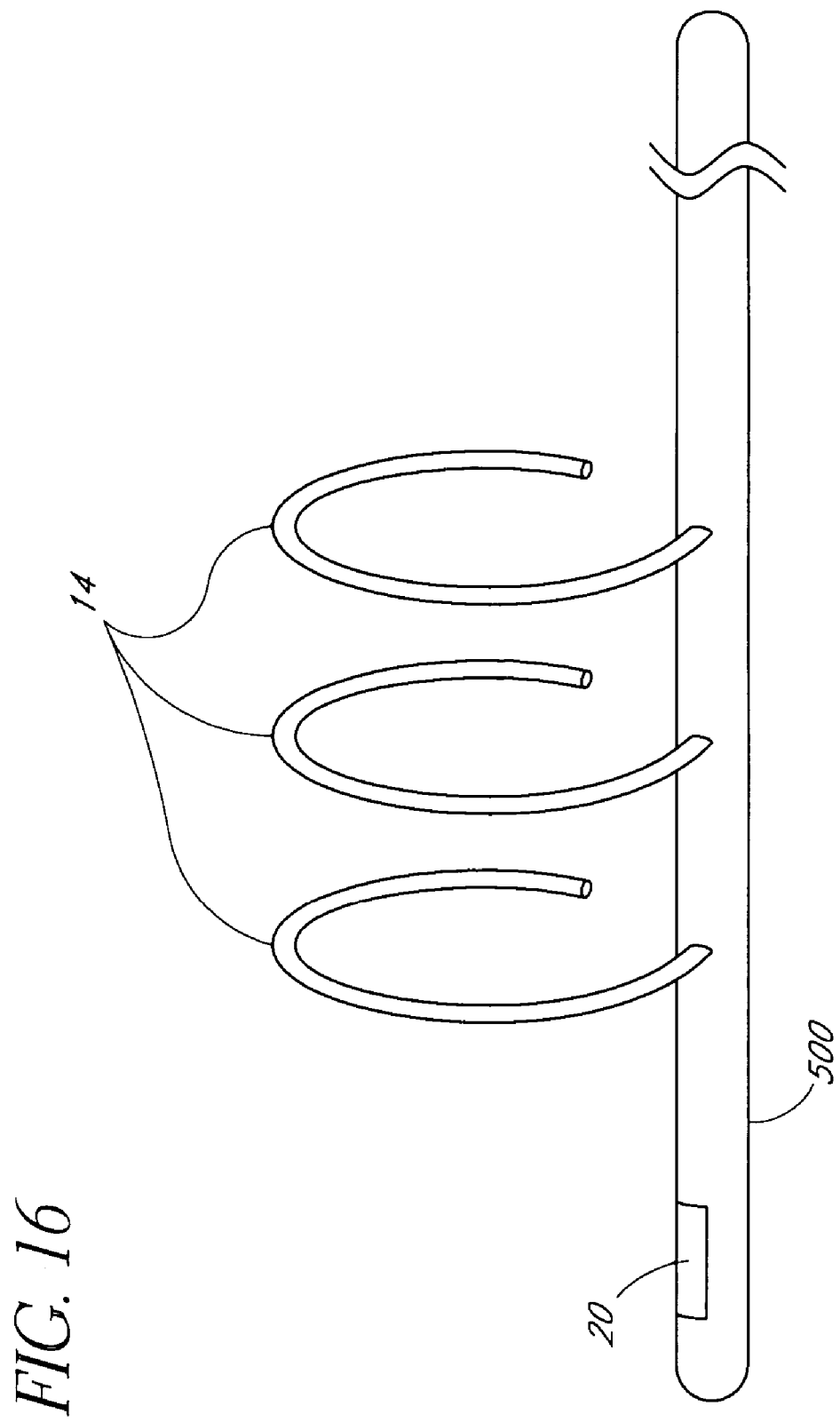
FIG. 16 is a side view diagram of a catheter containing a sensor near its distal end, with self-expanding split-ring anchors.

As shown in FIG. 16, the anchoring platform 14 is connected to a catheter 500, which contains multiple sensors 20, such as optode sensors, for monitoring pH, $pO_2$, and $pCO_2$, near its distal end. As in other embodiments, the anchors are made of a self-expanding material such as nitinol. As previously described, these anchors help to position the sensor near the wall, with the sensing surface 20 oriented toward the vessel lumen. These anchors may be split rings, which under a compressive load would form closed rings, resisting vessel compression due to vasospasm (Khatri, S. et al., "Stenting for Coronary Artery Spasm," Catheter Cardiovasc Interv., May 2000, 56(1):16–20, and Cheng, T. O., "Percutaneous Coronary Intervention for Variant Angina: Balloon vs. Stent", Catheter Cardiovasc Interv., 2002 May 56(1):21 but would also open up under tension to allow the catheter and sensor to be withdrawn at the end of its useful life. For monitoring of blood gases in the radial artery, which has a typical diameter of 3–4 mm, these anchors should have an expanded diameter of 3.5–5 mm, to allow for slight oversizing of the anchors, which is common practice in stent placement. The catheter and sensor may be withdrawn from the patient using a slightly larger catheter sheath, in order to accommodate the anchors, and protect the vessel from further damage during removal. As an alternative to placing the sensor near the side of the vessel, the catheter and sensor could be centered in the vessel, with one or more struts connecting the sensor to one or more support rings. The support rings serve to maintain the position of the sensor in the center of the vessel, and additionally serve to resist vessel compression due to vasospasm, and may reduce the risk of vessel compression due to joint flexion. In another embodiment, the support rings may have a helical configuration, the helix being joined to the sensor by one or more struts, which help to position the sensor in the center of the bloodstream. The use of a helical support structure which is connected to the catheter at only a single point provides the option of removing the sensor, even after the wound healing process has occurred, and fibrin which deposits on the strut surfaces has transformed into fibro-collagenous tissue. This is because the helix can be unwound, and pulled into the retrieval catheter. Thus, the addition of these support anchors serves to counteract vessel compression, one of the main obstacles that prevents IABG sensors from functioning long-term in an arterial setting. Appropriate positioning of the sensor in the flow field also minimizes the risk that slow flow will cause thrombosis and sensor fouling. Alternatively, the sensors may be placed in an artery that is larger than the radial artery, such as the femoral artery, and the present invention is suitable for numerous intravascular locations.

In addition to monitoring pH, O2, and CO2, it is also possible to use optodes to measure any of a variety of different species using ion-selective membranes with ionophores. (Bakker, E., et al., "Carrier-Based Ion-Selective Electrodes and Bulk Optodes. 1. General Characteristics" Chem. Rev. 1997 97:3083–3132). These ion selective sensors, whether optical or electrochemical, are based on lipophilic complexing agents capable of reversibly binding ions, called ionophores. The sensing layer of most ion selective electrodes (ISE's) or optodes is an organic polymeric membrane, of which polyvinyl chloride (PVC) is the most widely used. Other materials such as derivatized PVC, silicone rubber, or polyurethanes can also be used. A requirement for such membranes is that its glass transition temperature needs to be below the operating temperature. This requirement is necessary to allow reasonably rapid diffusion times. Alternatively, plasticizers, such as those used in PVC can be used to achieve the same goal. The plasticizer is typically selected for its compatibility with the ionophore. The ionophore determines the selectivity of the sensor. The final component of the ISE membrane is either a quaternary ammonium salt, to provide cationic sites, or tetraphenylborate salts to provide anionic sites. (R. D. Johnson et al, "Ionophore-based ion-selective potentiometric and optical sensors," Anal. Bioanal. Chem. 2003 June; 376(3):328–41.)

It is possible to alter the surface of these ISE membranes in order to improve their blood compatibility, such as with the use of phosphoryl choline (Berrocal M J, et al, "Improving the blood-compatibility of ion-selective electrodes by employing poly(MPC-co-BMA), a copolymer containing phosphorylcholine, as a membrane coating." Anal. Chem. Aug. 1 2002; 74(15):3644–8) or with heparin, poly(ethylene glycol), or poly(vinyl pyrrolidone), or the ISE membrane may first be covered by a protective membrane such as ePTFE with 0.4 micron porosity, and then surface modifications applied. Among the species that can be monitored using these technologies are calcium, chlorine, potassium, sodium, bicarbonate, phosphate, phosphorous, and magnesium. Other metal ions which can be detected using this technology include lithium, ammonium, rubidium, cesium, beryllium, strontium, barium, molybdenum, iron, copper, silver, zinc, cadmium, mercury, thallium, bismuth, lead, uranium, and samarium. Other inorganic ionic analytes which can be measured using this technology include creatinine, organic ammonium ions, nucleotides, and polyionic analytes such as heparin and protamine. (Buhlmann P, et al, "Carrier-Based Ion-Selective Electrodes and Bulk Optodes. 2. Ionophores for Potentiometric and Optical Sensors," Chem Rev. Jun. 18 1998; 98(4):1593–1688). The response of ISE's toward a single analyte ion is described by the Nernst equation.

In a further aspect of the invention, a pressure sensor can be implanted within a blood vessel in order to monitor a patient on a continuous basis. The pressure sensor may be similar to many described in the art, such as potentiometric pressure sensors, inductive pressure sensors, capacitive pressure sensors, piezoelectric pressure sensors, and strain gage pressure sensors. The pressure sensor can also be a micro electromechanical system (MEMS) device such as those made by Honeywell, Sensym, or All Sensors Corp (San Jose, Calif.) that is constructed using microfabrication methods that are well known in the microelectronics industry. Once the pressure signal has been converted into an electrical signal, the signal is then transmitted to an external receiver that may be worn by the patient. The sensor can be configured on the anchoring platform in any of the various configurations previously described in this disclosure, including those in which the sensor itself is retrievable in the case of sensor malfunction.

It is also valuable to monitor the condition of patients who have abdominal aortic aneurysms, which can be treated with endovascular stent-grafts. Sonesson et al. (Sonesson B., et al., "Intra-aneurysm pressure measurements in successfully excluded abdominal aortic aneurysm after endovascular repair" J Vasc Surg 37:733–8 (2003)) describe how monitoring the pressure on both the luminal side and aneurysmal side of such stent-grafts can help a physician to determine when and whether follow-up intervention is required. However, in their study, a follow-up catheterization procedure was required to monitor these pressures. It would clearly be advantageous to be able to obtain this information without having to perform an additional procedure. An implantable pressure sensor as described herein which does not become covered with a layer of fibrocollagenous tissue would provide accurate intra-arterial measurements. If a second sensor were mounted on the aneurysmal side of the stent-graft, its signal would not change substantially, as the healing process within the aneurysmal sack is known to be substantially delayed.

Schmitz-Rode et al. (Schmitz-Rode T, Schnakenberg U, Pfeffer J G, Piroth W, Vom Bogel G, Mokwa W, Gunther R W, "Vascular capsule for telemetric monitoring of blood pressure," Rofo Fortschr Geb Rontgenstr Neuen Bildgeb Verfahr. 2003 February; 175(2):282–6) describe a capsular pressure sensor that is implanted in the arterial system at an arterial branch. Three self-expanding legs were attached to the sensor capsule in order to maintain sensor position and prevent migration as well as occlusion (WO 00/74557, 7 Jun. 2000 to T. Schmitz-Rode, et al.). However, they reported that in 3/6 cases, the devices migrated several centimeters to the next arterial bifurcation, where the device became lodged, and caused an occlusion of one of the branch vessels. The three-leg anchoring system of this device means that it is prone to tilting, and so its exact position with the vessel is not controllable. Further, this device is not easily retrievable in the event of patient need or device failure. In addition, physicians would prefer to use a device whose placement is more accurate. It may also be important to monitor pressures at a location distant from an arterial bifurcation. Hence, an improved anchoring system, as described herein, can provide a significant improvement in this area.

Bullister et al. (Bullister E., et al., "A Blood Pressure Sensor for Long-Term Implantation," Artificial Organs 25(5):376–379 (2001)) describe a pressure sensor that is mounted within the wall of a titanium tube, and that may be used in line with a left ventricular assist device. However, such a device would require surgical implantation, which may not be appropriate for monitoring many patients, especially critical care patients, whose condition may exclude them as surgical candidates. In addition, if such a sensor were anastamosed end-to-end in a vessel, there would be a clear compliance mis-match between the vessel and the sensor. Compliance mis-match is well established as a cause of vascular graft failure.

Pressure sensors that are attached to stents have also been disclosed (U.S. Pat. No. 6,015,387 issued Jan. 18, 2000 to Schwartz et al. and U.S. Pat. No. 6,053,873 issued Apr. 25, 2000 to Govari et al.). Govari describes positioning of a pressure sensor on the outer wall of a stent. However, without proper positioning of the sensor with respect to the stent and the vessel lumen, the sensor surface will be covered with fibrin, which will subsequently transform into fibrous tissue, as part of the natural healing process. The fibrous tissue will create a barrier between the sensor and the blood, and will affect the value of the pressure readings obtained from the sensor. The fibrous tissue itself has elastic properties that will vary over time, and will be dependent on the thickness of the tissue layer that is formed. Thus, such a system may not allow immediate determination of whether the sensor is covered with tissue, or whether patient intervention is required. In addition, the devices described by Schwartz and Govari are not designed to be retrievable in case the sensor fails to function properly.

Ultrasonic flow sensors of the type described in U.S. Pat. No. 6,053,873 to Govari et al., which is hereby incorporated in its entirety, may be mounted in a hermetically sealed sensor housing made from epoxy, glass, ceramic, stainless steel, or the like, and mounted on the luminal surface of a stent, such that the luminal surface of the sensor housing protrudes into the lumen, as previously described. The sensor may alternatively be placed between two or more anchors, in such a manner that the sensor housing is designed to protrude into the lumen of the vessel, with respect to the anchors. The sensors are mounted at spaced-apart locations so that the transit time or Doppler ultrasound methods for determining flow rates described by Govari may be used. Additionally, the sensors may be positioned at an appropriate Doppler angle.

The anchors may consist of self-expansive materials, such as nitinol, or may be made from balloon expandable materials such as 316L stainless steel. In addition the anchors may be made from elements that are not closed curves, and which do not become interlocked with fibrous tissue over time. The open hoop structures shown in FIG. 16 are one type of anchor that may be suitable for practicing this invention. There may optionally be provided a retrieval hook at the downstream end of the sensor for removing the sensor at the end of its useful life. The sensor itself may be powered using an inductive link, or an implantable battery, and the sensor responses may be analyzed using an application-specific integrated circuit.

A thermal sensor for measuring flowrates is disclosed which consists of a thermal source, such as a resistive heating element, and at least one sensing unit, such as a thermistor or thermocouple. Both the heating element and the sensor are placed in the sensor housing, which protrudes into the lumen of the vessel in order to minimize tissue overgrowth. The heating element is placed upstream from the first thermocouple, and a small (<2.5° C.) temperature increase is applied to the bloodstream near the heating element. A second thermocouple is positioned immediately distal to the heating element to insure that the local temperature rise is small. The time for the temperature increase to be sensed by the downstream thermocouple is measured, and the flowrate may be determined from this information using standard thermodilution calculations.

Additionally, the Fick method for determination of cardiac output could be performed, using oxygen sensors described herein, placed in both the arterial circulation, and in the pulmonary artery. The Fick method for determining cardiac output is based on the principle that consumption of a substance (oxygen in this case) must equal blood flow to the organ multiplied by the difference between the arterial and venous concentrations of the substance. For this method, the formula for cardiac output is as follows:

$$CO = \frac{\text{oxygen consumption per minute }(VO2)}{(\text{arterial oxygen content} - \text{venous oxygen content})}$$

where oxygen content is calculated as: (1.34×[Hb]×oxygen saturation)/100. [Hb] is the hemoglobin concentration, which can be periodically assessed by a hemotology laboratory. In this case, the oxygen consumption can either be estimated or directly measured using standard techniques, or using the implantable sensors described herein. Arterial oxygen saturation is usually determined by arterial blood gas analysis (or using an implantable oxygen sensor described herein), while venous oxygen saturation is determined by mixed venous (pulmonary arterial) blood gas analysis (or using an implantable oxygen sensor described herein). There are a number of different sensors that would be appropriate for the measurement of nitric oxide (Berkels, R. et al. A new method to measure nitrate/nitrite with a NO-sensitive electrode. *J Appl Physiol* 90: 317–320, 2001). Because NO has a short half-life (2–30 s), it is difficult to measure authentic NO. It rapidly decomposes to nitrate and nitrite, which may accumulate in the sample. There are different methods of determining NO. It is possible to measure NO by using a bioassay, an oxyhemoglobin assay, electron paramagnetic resonance, chemiluminescence, HPLC, the Griess reaction, or different electrochemical electrodes. In addition, electrodes for NO detection are commercially available (WPI, Sarasota, Fla., and Inter Medical Co., Ltd., Nagoya, Japan).

Kilinc E, et al (J Pharm Biomed Anal. 2002 Apr. 15; 28(2):345–54) describe the use of an electrochemical sensor, similar to a glucose electrode, in that it consists of a amperometric, bi-polymer modified, platinum-iridium microelectrode. Most common biological interferences such as ascorbic acid, uric acid and glucose were eliminated via bi-polymer coatings of four layers of Nafion and a layer of 50 mM o-phenylenediamine (OPD).

The electrochemical reaction occurs at a working electrode at an applied voltage of 900 mV vs. Ag/AgCl electrode. The reaction is described below:

NO-e⁻ NO⁺

NO⁺+OH⁻ HNO₂

The redox current flowing between the working and reference electrodes is proportional to the concentration of NO, and is measured amperometrically (Zhang, X, et al., "Amperometric Detection of Nitric Oxide", Mod. Asp. Immunobiol. 1(4), 160–65, 2000).

An alternative system for measuring NO, involves the use of a microchip sensor (Zhang, X, et al., "A Novel Microchip Nitric Oxide Sensor with sub-nM Detection Limit", Electroanalysis 2002; 14(10):697–703. This system is also commercially available and may be employed in the current invention.

The sensor may be factory-calibrated using a nitric-oxide donor compound, such as SNAP (Zhang, Mod Asp Immunobiol 2000). Additionally, if deemed appropriate for the patient, calibration may be performed following implantation by local administration of a NO-releasing agent, such as nitroglycerin. The system may not require a high degree of accuracy, because there is a large burst of NO during ischemic stroke, and as long as such a burst was detected, the exact concentration level may not be critical.

In a preferred embodiment, an outer coating of heparin is applied to a layer of poly(ethylene glycol) (PEG), poly (vinylpyrrilidone) (PVP), or other hydrogel, in order to minimize thrombosis or fouling. The hydrogel is applied to a bioprotective layer of ePTFE, which prevents attack by macrophages. A polymer such as poly(dimethylsiloxane) or a polyester membrane such as Sympatex (Azko Nobel, Wuppertal, Germany) which is permeable to NO is employed. (Wang C, Deen, W M, "Nitric oxide delivery system for cell culture studies", Ann Biomed Eng. 2003 January; 31(1):65–79.) The ePTFE surrounds the NO-permeable membrane, and the NO-permeable membrane surrounds the electrode. A porphyrinic sensor may be constructed by coating a carbon-fiber electrode with a solution of nickel (II) tetrakis (3-methoxy-4-hydroxyphenyl) porphyrin (Tschudi, M R et al, "Direct In Situ Measurement of Nitric Oxide in Mesenteric Resistance Arteries", Hypertension 1996; 27:32–35), and then applying the outer membranes, excluding the NO-permeable membrane. Additionally, a layer of drug-releasing polymer, as described below, may be placed between the ePTFE membrane and the NO-permeable membrane, or may be placed only in certain areas between the ePTFE and NO-permeable membranes, such that there is direct contact between these two membranes. The coating or layer chosen to minimize thrombosis or fouling should have a porosity large enough to allow the analyte of interest to reach the sensing surface. In certain applications, radial inward displacement of the sensing surface may be reduced and longevity of the sensor still exist.

In addition to monitoring NO levels, it is also possible to measure nitrite or nitrate concentrations, using ion-selective electrodes, as previously described (Johnson, R D, et al, Anal Bioanal Chem (2003) 376: 328–341 and Bakker, E, Chem. Rev. 1997, 97, 3083–3132). Ion selective electrodes for monitoring nitrate and nitrite ions are commercially available (Vernier Software & Technology 13979 S. W. Millikan Way, Beaverton, Oreg. 97005 or Techne® Inc., 3 Terri Lane, Suite 10, Burlington, N.J. 08016). In addition, it is possible to measure nitrite ion concentrations by electrochemical oxidation of nitrite to nitrate, which occurs at a similar potential to the oxidation of nitric oxide to nitrite. Therefore, in another preferred embodiment, measurement of nitric oxide and nitrite and nitrate ions are performed simultaneously, by the use of nitric oxide and nitrite electrodes and nitrite and nitrate ion-selective electrodes.

Itoh Y, et al (Anal Biochem. Dec. 15 2000; 287(2):203–9), describe a fluorescent measurement for nitric oxide (NO) using diaminofluorescein DAF-FM and its diacetate (DAF-FM T). DAF-FM is converted via an NO-specific mechanism to an intensely fluorescent triazole derivative (DAF-FM T). They showed that in the presence of 1 μM DAF-FM, the concentrations of NOR-1, an NO donor, in the range of 2–200 nM was linearly related to the fluorescence intensity. However, this reaction is somewhat slower than the use of an NO electrode, having a maximal response at about 30 minutes.

This fluorescence reaction for monitoring NO can be monitored by the use of optodes, as described above for arterial blood gas monitoring, and for the immunosensor, described herein. An excitation light source at a wavelength of 500 nm is passed through the fiberoptic and reacts with the DAF-FM. The emission wavelength is at 515 nm. A photodiode detects the fluorescence intensity, and sends a signal via the radiotransmitter to an external alarm device worn by the patient. Alternatively, the alarm system can be set to contact someone besides the patient via telephony, such as a relative or physician, to notify them that immediate action needs to be taken.

While it is anticipated that hemodynamic effects will significantly reduce biological fouling, in the case of NO detection, it may additionally be desirable to further insure the prevention of endothelial growth by the elution of certain pharmacologic agents to prevent endothelial coverage of the sensor surface. Such anti-angiogenic agents include: paclitaxel (Belotti D, et al., "The microtubule-affecting drug paclitaxel has antiangiogenic activity", Clin Cancer Res. 1996 November; 2(11):1843–9.), rapamycin (Novak, K., "Swinging the vote for rapamycin" Nature Reviews Cancer 2002 2:75.) docetaxel (Guo, X L, et al., "Inhibitory effects of docetaxel on expression of VEGF, bFGF and MMPs of LS174T cell" World J Gastroenterol 2003; 9 (9): 1995–1998.) TNP-470 (Yeh, J R J, et al, "The antiangiogenic agent TNP-470 requires p53 and p21CIPyWAF for endothelial cell growth arrest", PNAS, 2000 97(23):12782–12787), carboxyamido-triazole (CAI), thalidomide, or interleukin-12 (Masiero, L, et al. "New anti-angiogenesis agents: review of clinical experience with carboxyamido-triazole (CAI), thalidomide, TNP-470, and interleukin-12" Angiogenesis 1997; 1(1):23–35.).

These may be released from a degradable matrix, such as PLGA, or from a non-degradable matrix, such as a ethylene vinyl acetate (EVA). This drug-releasing layer may be incorporated within the sensor housing inside the outer bioprotective layers.

In an alternative embodiment, it may be desirable to incorporate an enzyme in an enzyme-gel layer, as discussed previously with regard to glucose sensors. However, in this case, the enzyme is nitrate reductase, which converts nitrate into nitrite. The nitrite is then electrochemically oxidized back to nitrate, and provides an electrical current that is measured amperometrically.

Figure 18:
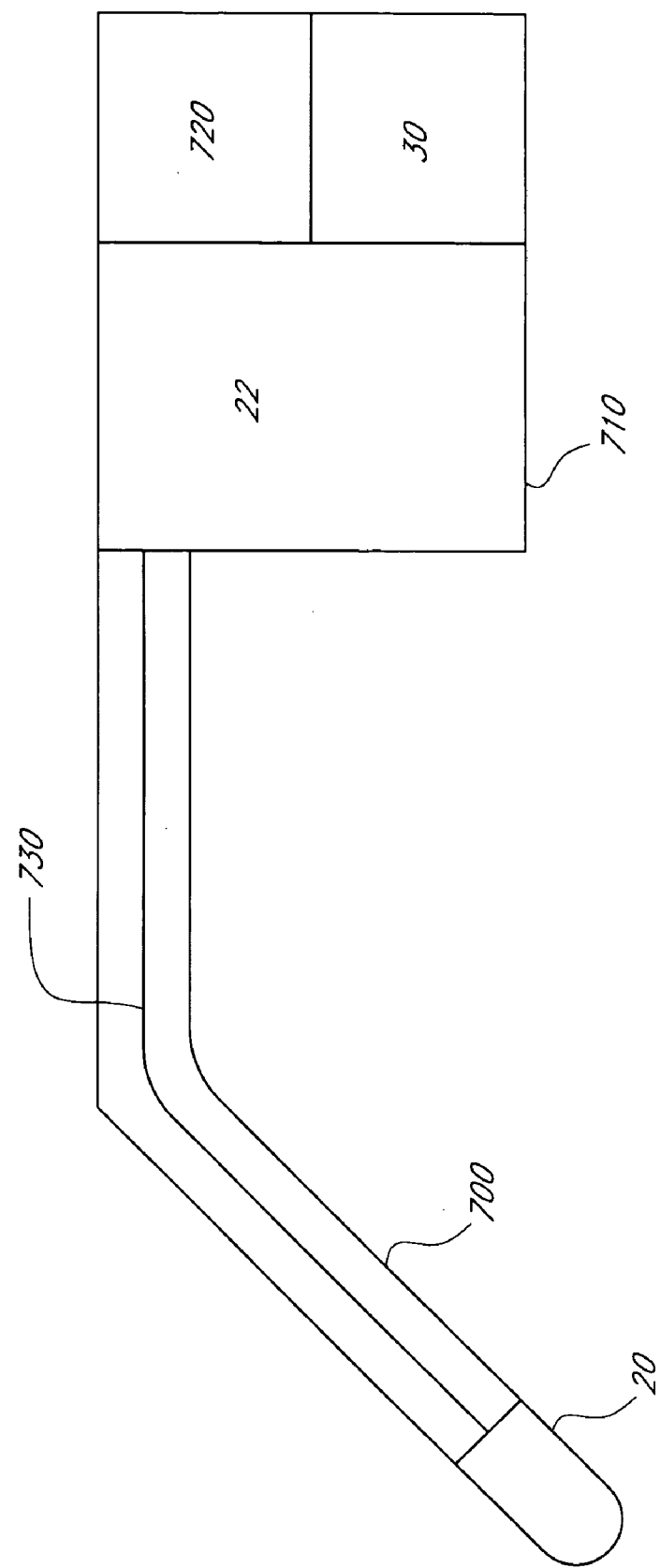
FIG. 18 shows a side view of a catheter containing a nitric oxide sensor.

In an alternative embodiment, as shown in FIG. 18, the nitric oxide or nitrite or nitrate sensor 20 may be incorporated into the distal end of a catheter-like tube 700. The proximal end of the catheter-like tube is attached to a hermetically sealed enclosure 710 which contains the antenna 30 and/or battery 720, and the electronic circuitry. Wire leads 730 are then used to connect the sensor 20 with the electronic circuitry. The device is implanted in a patient in a manner similar to transvenous pacemaker insertion which is well known to those of skill in the art. The physician makes a small incision in the skin, and then creates a hole in the vein to insert the distal tip of the catheter containing the sensor using techniques known to those of skill in the art. The hole is preferably smaller than the diameter of the distal tip of the catheter so that the distal tip is forced to stay in place. The distal tip containing the sensor is then advanced into the vein either blind or using ultrasound guidance. The enclosure containing the electronics is then placed subdermally, and the insertion site is closed using standard surgical techniques known to those of skill in the art. The signal indicative of the nitric oxide or nitrite or nitrate present is transmitted to a device worn externally by the patient, as described previously, and can communicate to the patient by an alarm which is either auditory or vibratory, or in the event of a stroke, can transmit information by telephony to either a physician, relative, caregiver, or emergent care provider.

In an alternative embodiment, it is possible to retrieve the sensor without the presence of a hook on the sensor or anchoring platform. Preferably, this is done using a sensor housing that is bonded to the anchoring platform using a degradable material, and this procedure is performed after the bonds have degraded. Also, this procedure is preferably performed using a distal protection device, such as the Angioguard (Cordis Corp.). Because the sensor is not covered by a layer of neointimal tissue, it is possible to remove the sensor using the retrieval system shown in FIGS. 17A and 17B. A catheter 600 with a set of clips 640 is shown, and a pair of balloons 620, 630 is placed on the side of the catheter tip opposite the clips. The catheter is maneuvered into position under fluoroscopic guidance, so that the clips 640 are adjacent to the sensor. Next, balloons 620 and 630 are inflated either sequentially or simultaneously, as appropriate for the individual case, so that the clips are forced around the sensor housing. Next, balloons 620 and 630 are deflated. Finally, the sensor that is being removed, and the catheter tip are separated from the wall of the vessel by inflating balloon 610. Balloon 610 is then deflated, and the entire system is removed from the patient, along with the sensor.

Although the present invention has been described in connection with certain preferred embodiments, persons of ordinary skill in the art will understand that many modifications can be made thereto within the scope of the claims which follow. Accordingly, the scope of the invention is not intended to be limited by the above description but instead is to be determined entirely by reference to the following claims.

What is claimed is:

1. A sensor for implantation within a blood vessel comprising:
   a support structure;
   a sensor housing carried by the support structure; and
   a sensing surface exposed to the exterior of the housing;
   wherein the sensor is configured to detect nitric oxide or a metabolic of nitric oxide, and wherein the sensor has streamlined configuration with respect to the support, and wherein the sensing surface includes a layer that minimizes the formation of thrombus.

2. An implantable sensor as in claim 1, wherein the support structure comprises a stent.

3. An implantable sensor as in claim 1, wherein the support structure comprises a catheter.

4. An implantable sensor as in claim 1, wherein the support structure comprises an expandable metal mesh.

5. An implantable sensor as in claim 1, wherein the sensor housing is positioned on the luminal side of the support structure.

6. An implantable sensor as in claim 1, wherein the sensor housing is positioned within an opening on the side wall of the support structure.

7. An implantable sensor as in claim 1, further comprising a tubular sleeve surrounding the support structure.

8. An implantable sensor as in claim 7, wherein the tubular sleeve is on the radially outwardly facing surface of the support structure.

9. An implantable sensor as in claim 7, wherein the tubular sleeve comprises ePTFE.

10. An implantable sensor as in claim 1, wherein the sensor comprises an ion-selective electrode.

11. An implantable sensor as in claim 1, wherein the sensor is selected from the group consisting of amperometric electrodes, porphyrinic electrodes, and microchip electrodes.

12. An implantable sensor as in claim 1, further containing an analyte permeable membrane and an enzyme gel layer.

13. An implantable sensor as in claim 12, wherein the enzyme gel layer comprises nitrate reductase.

14. A sensor for implantation within a blood vessel comprising:
   a support structure;
   a sensor housing carried by the support structure; and
   a sensing surface exposed to the exterior of the housing and wherein the sensing surface includes a layer that minimizes the formation of thrombus;
   wherein the sensor is configured to detect a metabolic product of nitric oxide.

15. An implantable sensor as in claim 14, wherein the support structure comprises a stent.

16. An implantable sensor as in claim 14, wherein the support structure comprises a catheter.

17. An implantable sensor as in claim 14, wherein the support structure comprises an expandable metal mesh.

18. An implantable sensor as in claim 14, wherein the sensor housing is positioned on the luminal side of the support structure.

19. An implantable sensor as in claim 14, wherein the sensor housing is positioned within an opening on the side wall of the support structure.

20. An implantable sensor as in claim 14, further comprising a tubular sleeve surrounding the support structure.

21. An implantable sensor as in claim 20, wherein the tubular sleeve is on the radially outwardly facing surface of the support structure.

22. An implantable sensor as in claim 20, wherein the tubular sleeve comprises ePTFE.

23. An implantable sensor as in claim 14, wherein the sensor comprises an ion-selective electrode.

24. An implantable sensor as in claim 14, wherein the sensor is selected from the group consisting of amperometric electrodes, porphyrinic electrodes, and microchip electrodes.

25. An implantable sensor as in claim 14, further containing an analyte permeable membrane and an enzyme gel layer.

26. An implantable sensor as in claim 25, wherein the enzyme gel layer comprises nitrate reductase.

* * * * *

UNITED STATES PATENT AND TRADEMARK OFFICE
CERTIFICATE OF CORRECTION

PATENT NO. : 7,181,261 B2
APPLICATION NO. : 10/758495
DATED : February 20, 2007
INVENTOR(S) : Silver et al.

It is certified that error appears in the above-identified patent and that said Letters Patent is hereby corrected as shown below:

At column 2, line 9, please delete "(19916)." And insert -- (1996). --, therefore.

At column 2, line 46, please delete "sweat;" and insert --sweat, --, therefore.

At column 6, line 2, please delete "LABG" and insert -- IABG --, therefore.

At column 12, line 61, please delete "sterits" and insert -- stents --, therefore.

At column 17, line 29, please delete "amplifer/filter" and insert -- amplifier/filter --, therefore.

At column 19, line 17(Approx), after "an" please delete "with".

At column 21, line 3(Equation), please delete "$H_2O_2 \rightarrow O_2+2H++2e^-$" and insert -- $H_2O_2 \rightarrow O_2+2H^++2e^-$ --, therefore.

At column 25, lines 13-14, please delete "polytetrofluroethylene," and insert -- polytetrafluoroethylene --, therefore.

At column 27, line 58(Approx), please delete "graft;" and insert -- graft, --, therefore.

At column 29, line 6, after "profile is" insert -- almost flat, e.g., --.

At column 31, line 4(under ANALYTE), please delete "1-methionine" and insert -- 1-methionine --, therefore.

At column 31, line 4(under ENZYME), please delete "1-amino acid oxidase" and insert -- 1-amino acid oxidase --, therefore.

At column 31, line 5(under ANALYTE), please delete "1-pheylalanine" and insert -- 1-pheylalanine --, therefore.

At column 31, line 5(under ENZYME), please delete "1-amino acid oxidase" and insert -- 1-amino acid oxidase --, therefore.

UNITED STATES PATENT AND TRADEMARK OFFICE
CERTIFICATE OF CORRECTION

| | |
|---|---|
| PATENT NO. | : 7,181,261 B2 |
| APPLICATION NO. | : 10/758495 |
| DATED | : February 20, 2007 |
| INVENTOR(S) | : Silver et al. |

It is certified that error appears in the above-identified patent and that said Letters Patent is hereby corrected as shown below:

At column 33, line 7, please delete "2000;" and insert -- 2001 --, therefore.

At column 33, line 21, please delete "Innunosensor" and insert -- Immunosensor --, therefore.

At column 40, line 42(Approx), please delete "times" and insert -- times, --, therefore.

At column 42, line 14, please delete "O2," and insert -- $O_2$, --, therefore.

At column 42, line 14, please delete "CO2," and insert -- $CO_2$, --therefore.

At column 42, line 38 after "41.)" insert -- . --

At column 45, line 12(Approx)(Equation), please delete "(VO2)" and insert -- $(VO_2)$ --, therefore.

At column 48, line 44(Approx), In claim 1, after "metabolic" insert -- product --.

Signed and Sealed this

Thirty-first Day of July, 2007

JON W. DUDAS
*Director of the United States Patent and Trademark Office*

UNITED STATES PATENT AND TRADEMARK OFFICE
CERTIFICATE OF CORRECTION

PATENT NO. : 7,181,261 B2
APPLICATION NO. : 10/758495
DATED : February 20, 2007
INVENTOR(S) : Silver et al.

It is certified that error appears in the above-identified patent and that said Letters Patent is hereby corrected as shown below:

At page 2, column 1, please delete "Nioelectronics," and insert -- Bioelectronics, --, therefore.
At page 2, column 2, line 9, please delete "*Sylindrical*" and insert -- *Cylindrical* --, therefore.
At page 2, column 2, line 35, please delete "16;" and insert -- 16: --, therefore.
At page 2, column 2, line 36, please delete "((1991)." And insert -- (1991). --, therefore.
At page 2, column 2, line 40, please delete "1992" and insert -- (1992) --, therefore.
At page 2, column 2, line 61, please delete "Plamaz-Schartz" and insert -- Palmaz-Schatz --, therefore.
At column 15, line 26, please delete "tubul" and insert -- tubular --, therefore.

Signed and Sealed this

Fourth Day of September, 2007

JON W. DUDAS
*Director of the United States Patent and Trademark Office*